United States Patent
Song et al.

(10) Patent No.: US 10,651,396 B2
(45) Date of Patent: May 12, 2020

(54) ORGANIC COMPOUND, AND ORGANIC LIGHT EMITTING DIODE AND ORGANIC LIGHT EMITTING DISPLAY DEVICE INCLUDING THE SAME

(71) Applicant: LG Display Co., Ltd., Seoul (KR)

(72) Inventors: In-Bum Song, Seoul (KR); Chun-Ki Kim, Seoul (KR)

(73) Assignee: LG DISPLAY CO., LTD., Seoul (KR)

( * ) Notice: Subject to any disclaimer, the term of this patent is extended or adjusted under 35 U.S.C. 154(b) by 236 days.

(21) Appl. No.: 15/794,632

(22) Filed: Oct. 26, 2017

(65) Prior Publication Data

US 2018/0130953 A1 May 10, 2018

(30) Foreign Application Priority Data

Oct. 31, 2016 (KR) .................. 10-2016-0143282

(51) Int. Cl.
| | |
|---|---|
| *H01L 51/50* | (2006.01) |
| *H01L 51/00* | (2006.01) |
| *C07D 403/10* | (2006.01) |
| *C07D 487/04* | (2006.01) |
| *C07D 491/048* | (2006.01) |

(Continued)

(52) U.S. Cl.
CPC ........ *H01L 51/0071* (2013.01); *C07D 403/10* (2013.01); *C07D 487/04* (2013.01); *C07D 491/048* (2013.01); *C07D 495/04* (2013.01); *H01L 51/0067* (2013.01); *H01L 51/0072* (2013.01); *H01L 27/3244* (2013.01); *H01L 51/001* (2013.01); *H01L 51/0085* (2013.01); *H01L 51/5016* (2013.01); *H01L 51/5056* (2013.01); *H01L 51/5072* (2013.01); *H01L 51/5088* (2013.01); *H01L 51/5092* (2013.01);

(Continued)

(58) Field of Classification Search
None
See application file for complete search history.

(56) References Cited

U.S. PATENT DOCUMENTS 8,062,769 B2 † 11/2011 Kai
8,962,158 B2 † 2/2015 Komori
(Continued)

FOREIGN PATENT DOCUMENTS

| | | |
|---|---|---|
| CN | 104271700 A | 1/2015 |
| CN | 104583184 A | 4/2015 |

(Continued)

*Primary Examiner* — Gregory D Clark
(74) *Attorney, Agent, or Firm* — Birch, Stewart, Kolasch & Birch, LLP

(57) ABSTRACT

The present invention provides an organic compound for an organic light emitting diode. An example of the organic compound is represented by:

$$\begin{array}{c} R_1 \\ | \\ (L_1)_m \\ | \\ N \end{array}$$

with structure showing $X_1$, $X_2$, $X_3$ substituents on a carbazole ring connected to $-(L_2)_n-R_2$.

13 Claims, 2 Drawing Sheets

(51) Int. Cl.
*C07D 495/04* (2006.01)
*H01L 27/32* (2006.01)
*H01L 51/56* (2006.01)

(52) U.S. Cl.
CPC ...... *H01L 51/56* (2013.01); *H01L 2251/5384* (2013.01); *H01L 2251/558* (2013.01)

(56) References Cited

U.S. PATENT DOCUMENTS 9,156,843 B2 † 10/2015 Kai
2004/0164292 A1* 8/2004 Tung ................ G02F 1/133603
257/40
2016/0351826 A1* 12/2016 Kim .................... C07D 495/04

FOREIGN PATENT DOCUMENTS

| | | | |
|---|---|---|---|
| CN | 104603232 A | 5/2015 | |
| KR | 2016-0060572 * | 5/2015 | ............. C09K 11/06 |
| WO | WO 2013/151297 A1 | 10/2013 | |
| WO | WO 2014/038867 A1 | 3/2014 | |
| WO | WO 2014/042405 A1 | 3/2014 | |
| WO | WO 2015/105315 A1 | 7/2015 | |
| WO | WO 2015/160224 A1 | 10/2015 | |
| WO | WO 2015/076629 A1 | 5/2016 | |
| WO | WO 2016/080791 A1 * | 5/2016 | ......... C07D 4034/14 |

\* cited by examiner
† cited by third party

400

ORGANIC COMPOUND, AND ORGANIC LIGHT EMITTING DIODE AND ORGANIC LIGHT EMITTING DISPLAY DEVICE INCLUDING THE SAME

CROSS-REFERENCE TO RELATED APPLICATION

The present application claims priority to and the benefit of Korean Patent Application No. 10-2016-0143282 filed in the Republic of Korea on Oct. 31, 2016, which is hereby incorporated by reference in its entirety.

BACKGROUND OF THE INVENTION

Field of the Invention

Embodiments of the invention relate to an organic compound, and more particularly, to an organic compound being capable of improving an emitting efficiency, a durability and a lifetime of an organic light emitting diode and an organic light emitting display device.

Discussion of the Related Art

Recently, as requirements of a flat panel display device having a small occupied area have increased, an organic light emitting display (OLED) device including an organic light emitting diode have been technically developed. The OLED device may be referred to as an organic electroluminescent device (OELD).

The organic light emitting diode emits light by injecting electrons from a cathode as an electron injection electrode and holes from an anode as a hole injection electrode into an emitting material layer (EML), combining the electrons with the holes, generating an exciton, and transforming the exciton from an excited state to a ground state. A flexible substrate, for example, a plastic substrate, can be used as a base substrate where elements are formed. The OLED device can be operated at a voltage (e.g., 10V or below) lower than a voltage required to operate other display devices. Moreover, the OLED device has an excellent color purity. In addition, the OLED device has advantages in the viewing angle and the contrast ratio in comparison to the LCD device, and the organic light emitting diode may be formed on a flexible substrate, such as a plastic substrate.

An organic emitting layer of the OLED device may have a single-layered structure of an emitting material layer (EML). Alternatively, to improve an emitting efficiency, the organic emitting layer may have a multi-layered structure. For example, the organic emitting layer may include a hole injection layer (HIL), a hole transporting layer (HTL), the EML, an electron transporting layer (ETL) and an electron injection layer (EIL).

To further improve the property or characteristic of the organic light emitting diode, a white emitting diode including at least two stacks is introduced. It may be referred to as a tandem structure organic light emitting diode. The tandem structure organic light emitting diode includes a charge generation layer (CGL) between adjacent stacks.

The process for fabrication of the related art OLED device is briefly described.

(1) A transparent conductive material, e.g., indium-tin-oxide (ITO) is deposited on a substrate to an anode.

(2) An organic material, e.g., dipyrazino[2,3-f:2',3'-h]quinoxaline-2,3,6,7,10,11-hexacarbonitrile (HATCN) is deposited on the anode to form a hole injection layer (HIL) having a thickness of about 10 nm to 60 nm.

(3) An organic material, e.g., 4,4'-bis[N-(1-naphthyl)-N-phenylamino]-biphenyl (NPB) is deposited on the HIL to form a hole transporting layer (HTL) having a thickness of about 20 nm to 60 nm. In the phosphorescent organic light emitting diode, an exciton blocking layer such as an electron blocking layer (EBL) may be further formed on the HTL to efficiently trap the triplet exciton in an emitting material layer (EML).

(4) The EML including a host and a dopant is formed on the HTL (or the EBL). In the blue emission, 9,10-Bis(1-naphtyl)anthracene($\alpha$-ADN) may be used as the host, and 4,4'-bis[2-(4-(N,N-diphenylamino)phenyl)vinyl]biphenyl (DPAVBi) or diphenyl-[4-(2-[1,1;4,1]terphenyl-4-yl-vinyl)-phenyl]-amine(BD-1) may be used as the dopant. The dopant may have a weight % of 1 to 50, preferably 1 to 10. The EML may have a thickness of about 20 nm to 60 nm.

(5) An electron transporting layer (ETL) and an electron injection layer (EIL) are sequentially formed on the EML. Ttris-(8-hydroxyquinoline aluminum (Alq3) may be used for the ETL, and LiF may be used for the ETL. In the phosphorescent organic light emitting diode, a hole blocking layer (HBL) may be further formed between the EML and the ETL to efficiently trap the triplet exciton in an emitting material layer (EML).

(6) A cathode is formed on the EIL.

As mentioned above, the organic light emitting diode emits light by injecting electrons from the cathode and holes from the anode into the EML, combining the electrons with the holes and generating an exciton. Since a single emitting material is used in the EML, the color purity, the emitting efficiency and the lifetime may be decreased. To improve the emitting efficiency and the lifetime, a host and a dopant are used for the EML. In the host-dopant system, the host generates an exciton and provide an energy into the dopant such that the light is efficiently emitted from the dopant. Namely, the energy, which is generated when the exciton is transited from an excited state to the ground state, is provided into the dopant via the host. As a result, in the host-dopant system, the energy is efficiently transferred into the dopant such that the exciton generation probability in the dopant is increased. Accordingly, the emitting efficiency of the organic light emitting diode is increased.

The emitting material is an important factor determining the emitting efficiency of the organic light emitting diode. In the host-dopant system, the host has strong effect on the emitting efficiency and the lifetime of the organic light emitting diode. Korean Patent No. 10-1404346 disclosed vinyl type norbornene polymer as a green phosphorescent host.

On the other hand, the emitting material in the organic light emitting diode should have good quantum efficiency, a high electron mobility and a high hole mobility. Since the related art host material has a wide band gap, the hole injection into the EML is delayed such that the driving voltage of the organic light emitting diode is increased. In addition, since the hole and the electron injected into the EML is unbalanced, the emission may be generated at an interface of the EML and adjacent layer such that the emitting efficiency and the lifetime are decreased.

Recently, a large-size organic light emitting display device having a high efficiency and a long lifetime is further required. Accordingly, a new emitting material having a high thermal stability and a high hole-electron balance to provide high emitting efficiency and lifetime is required.

SUMMARY OF THE INVENTION

Accordingly, embodiments of the present invention are directed to an organic compound, an organic light emitting diode and an organic light emitting display (OLED) device including the same that substantially obviates one or more of the problems due to limitations and disadvantages of the related art.

An object of the present invention is to provide an organic compound having a high hole mobility, a high electron mobility and a high thermal stability.

An object of the present invention is to provide an organic compound being capable of improving the emitting efficiency and the color purity of the organic light emitting diode and the OLED device.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described herein, an organic compound is represented by following Formula:

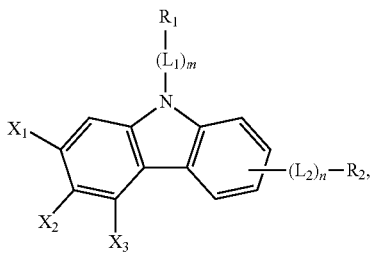

wherein $R_1$ is independently selected from the group consisting of substituted or non-substituted $C_5$ to $C_{30}$ aryl group, substituted or non-substituted $C_5$ to $C_{30}$ heteroaryl group, substituted or non-substituted $C_6$ to $C_{30}$ arylalkyl group, substituted or non-substituted $C_6$ to $C_{30}$ hetero-arylalkyl group, non-substituted $C_6$ to $C_{30}$ aryloxyl group and substituted or non-substituted $C_6$ to $C_{30}$ hetero-aryloxyl group, and $R_2$ is independently selected from the group consisting of hydrogen, deuterium, tritium, substituted or non-substituted $C_5$ to $C_{30}$ aryl group, substituted or non-substituted $C_5$ to $C_{30}$ heteroaryl group, substituted or non-substituted $C_6$ to $C_{30}$ arylalkyl group, substituted or non-substituted $C_6$ to $C_{30}$ hetero-arylalkyl group, non-substituted $C_6$ to $C_{30}$ aryloxyl group and substituted or non-substituted $C_6$ to $C_{30}$ hetero-aryloxyl group, wherein each of $L_1$ and $L_2$ is independently selected from the group consisting of substituted or non-substituted $C_1$ to $C_{30}$ alkylene group, substituted or non-substituted $C_3$ to $C_{30}$ cyclo-alkylene group, substituted or non-substituted $C_5$ to $C_{30}$ arylene group, substituted or non-substituted $C_4$ to $C_{30}$ heteroarylene group, substituted or non-substituted $C_6$ to $C_{30}$ arylalkylene group, substituted or non-substituted $C_6$ to $C_{30}$ hetero-arylalkylene group, substituted or non-substituted $C_6$ to $C_{30}$ aryloxylene group and substituted or non-substituted $C_6$ to $C_{30}$ hetero-aryloxylene group, and each of m and n is 0 or 1, and wherein $X_2$ with one of $X_1$ and $X_3$ forms a $C_4$ to $C_{30}$ homo fused-ring or a $C_4$ to $C_{30}$ hetero fused-ring, and the other one of $X_1$ and $X_3$ is selected from the group consisting of hydrogen, deuterium, tritium, substituted or non-substituted $C_1$ to $C_{20}$ alkyl group, substituted or non-substituted $C_1$ to $C_{20}$ alkoxy group, substituted or non-substituted $C_5$ to $C_{30}$ aryl group and substituted or non-substituted $C_5$ to $C_{30}$ heteroaryl group.

In another aspect, an organic light emitting diode comprises a first electrode; a second electrode facing the first electrode; and an organic layer between the first and second electrodes and including the above organic compound.

In another aspect, an organic light emitting diode comprises a first electrode; a second electrode facing the first electrode; and an organic layer between the first and second electrodes and including the above organic compounds and a dopant.

In another aspect, an organic light emitting display device comprises a substrate; the above organic light emitting diode: and a thin film transistor between the substrate and the organic light emitting diode and connected to the organic light emitting diode.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE EMBODIMENTS

Figure 1:
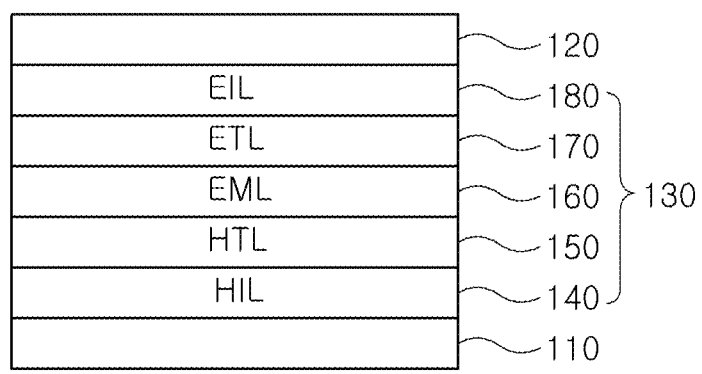
FIG. 1 is a schematic cross-sectional view of an organic light emitting diode according to a first embodiment of the present invention.

Reference will now be made in detail to the preferred embodiments, examples of which are illustrated in the accompanying drawings. The term 'may' fully encompasses all the meanings of the term 'can'. All the components of an organic light emitting diode as well as display device including the organic light emitting diodes according to all embodiments of the present invention are operatively coupled and configured.

An emitting material used in an organic light emitting diode is required to have excellent properties, including a high quantum efficiency (emitting efficiency), a high hole mobility and a high electron mobility. In addition, the emitting material is required to be uniformly arranged (or dispersed) in an EML and stably induce emission. Moreover, the host in the host-dopant system is required to have a molecular weight to be formed by a vacuum deposition. Further, the host is required to have high glass transition temperature and thermal decomposition temperature for thermal stability. The host is further required to have a high electrochemical stability for the lifetime and a good interface adhesive property with an adjacent layer.

An organic compound of the present invention capable of meeting the above requirements is represented in Formula 1.

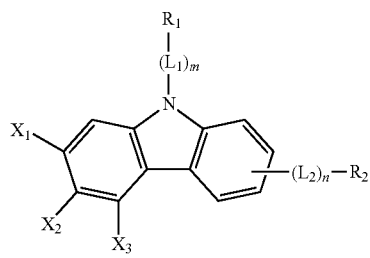

[Formula 1]

In Formula 1, R1 is independently selected from the group consisting of substituted or non-substituted C5 to C30 aryl group, substituted or non-substituted C5 to C30 heteroaryl group, substituted or non-substituted C6 to C30 arylalkyl group, substituted or non-substituted C6 to C30 hetero-arylalkyl group, non-substituted C6 to C30 aryloxyl group and substituted or non-substituted $C_6$ to $C_{30}$ hetero-aryloxyl group, and $R_2$ is independently selected from the group consisting of hydrogen, deuterium, tritium, substituted or non-substituted $C_5$ to $C_{30}$ aryl group, substituted or non-substituted $C_5$ to $C_{30}$ heteroaryl group, substituted or non-substituted $C_6$ to $C_{30}$ arylalkyl group, substituted or non-substituted $C_6$ to $C_{30}$ hetero-arylalkyl group, non-substituted $C_6$ to $C_{30}$ aryloxyl group and substituted or non-substituted $C_6$ to $C_{30}$ hetero-aryloxyl group.

Each of $L_1$ and $L_2$ is independently selected from the group consisting of substituted or non-substituted $C_1$ to $C_{30}$ alkylene group, substituted or non-substituted $C_3$ to $C_{30}$ cyclo-alkylene group, substituted or non-substituted $C_5$ to $C_{30}$ arylene group, substituted or non-substituted $C_4$ to $C_{30}$ heteroarylene group, substituted or non-substituted $C_6$ to $C_{30}$ arylalkylene group, substituted or non-substituted $C_6$ to $C_{30}$ hetero-arylalkylene group, substituted or non-substituted $C_6$ to $C_{30}$ aryloxylene group and substituted or non-substituted $C_6$ to $C_{30}$ hetero-aryloxylene group, and each of "m" and "n" is 0 (zero) or 1.

$X_2$ with one of $X_1$ and $X_3$ forms a $C_4$ to $C_{30}$ homo fused-ring or a $C_4$ to $C_{30}$ hetero fused-ring. In this instance, the other one of $X_1$ and $X_3$ is selected from the group consisting of hydrogen, deuterium, tritium, substituted or non-substituted $C_1$ to $C_{20}$ alkyl group, substituted or non-substituted $C_1$ to $C_{20}$ alkoxy group, substituted or non-substituted $C_5$ to $C_{30}$ aryl group and substituted or non-substituted $C_5$ to $C_{30}$ heteroaryl group.

The term "substituted" encompasses embodiments in which the substituent may include halogen-substituted or non-substituted alkyl group, halogen-substituted or non-substituted alkoxy group, halogen, cyano group, carboxyl group, carbonyl group, amino group, alkylamino group, nitro group, hydrozyl group, sulfonate group, alkyl silyl group, alkoxy silyl group, cycloakyl silyl group, aryl silyl group, substituted or non-substituted aryl group or heteroaryl group, but it is not limited thereto.

The term "hetero", which is used in heteroaryl, heteroarylene, and so on, means that at least one carbon atom in the aromatic ring or alicyclic ring is substituted by a heteroatom being selected from the group consisting of nitrogen atom (N), oxygen atom (O) and sulfur atom (S).

For example, $R_1$ may be independently selected from the group consisting of fused or non-fused homo-aromatic ring, such as phenyl, biphenyl, terphenyl, tetraphenyl, naphtyl, anthracenyl, indenyl, phenalenyl, phenanthrenyl, azulenyl, pyrenyl, fluorenyl, tetracenyl, indacenyl or spiro-fluorenyl, or fused or non-fused hetero-aromatic ring, such as pyrrolyl, pyridyl (or pyridinyl), pyrimidyl (pyrimidinyl), pyrazinyl, pyridazinyl, triazinyl, tetrazinyl, imidazolyl, pyrazolyl, indolyl, carbazolyl, benzocarbazolyl, dibenzocarbazolyl, indolocarbazolyl, indenocarbazolyl, quinolinyl, iso-quinolinyl, phthalazinyl, quinoxalinyl, cinnolinyl, quinazolinyl, phthalazinyl, benzoquinolinyl, benzoiso-quinolinyl, benzoquinazolinyl, benzoquinoxalinyl, acrydinyl, phenanthrolinyl, furanyl, pyranyl, oxazinyl, oxazolyl, oxadiazolyl, triazolyl, dioxynyl, benzofuranyl, dibenzofuranyl, thio-pyranyl, thiazinyl, thiophenyl or N-substituted spiro-fluorenyl, and $R_2$ may be independently selected from the group consisting of hydrogen, fused or non-fused homo-aromatic ring, such as phenyl, biphenyl, terphenyl, tetraphenyl, naphtyl, anthracenyl, indenyl, phenalenyl, phenanthrenyl, azulenyl, pyrenyl, fluorenyl, tetracenyl, indacenyl or spiro-fluorenyl, or fused or non-fused hetero-aromatic ring, such as pyrrolyl, pyridyl (or pyridinyl), pyrimidyl (pyrimidinyl), pyrazinyl, pyridazinyl, triazinyl, tetrazinyl, imidazolyl, pyrazolyl, indolyl, carbazolyl, benzocarbazolyl, dibenzocarbazolyl, indolocarbazolyl, indenocarbazolyl, quinolinyl, iso-quinolinyl, phthalazinyl, quinoxalinyl, cinnolinyl, quinazolinyl, phthalazinyl, benzoquinolinyl, benzo iso-quinolinyl, benzoquinazolinyl, benzoquinoxalinyl, acrydinyl, phenanthrolinyl, furanyl, pyranyl, oxazinyl, oxazolyl, oxadiazolyl, triazolyl, dioxynyl, benzofuranyl, dibenzofuranyl, thio-pyranyl, thiazinyl, thiophenyl or N-substituted spiro-fluorenyl.

For example, $R_1$ may be independently selected from the group consisting of phenyl, biphenyl, terphenyl, where each benzene ring is connected in a meta-position or a para-position, fluorenyl, spiro-fluorenyl, benzothiophenyl, dibenzothiophenyl, benzofuranyl, dibenzofuranyl, pyrrolyl, pyridinyl, pyrimidinyl, pyrazinyl, pyridazinyl, triazinyl, tetrazinyl, imidazolyl, pyrazolyl, indolyl, carbazolyl, benzocarbazolyl, dibenzocarbazolyl, indolocarbazolyl, indenocarbazolyl, benzofurano-carbazolyl, benzothieno-carbazolyl, quinolinyl, iso-quinolinyl, phthalazinyl, quinoxalinyl, cinnolinyl, quinazolinyl, benzoquinolinyl, benzo iso-quinolinyl, benzoquinazolinyl, spiro-carbazolyl and benzoquinoxalinyl, and $R_2$ may be independently selected from the group consisting of phenyl, biphenyl, terphenyl, where each benzene ring is connected in a meta-position or a para-position, fluorenyl, benzothiophenyl, dibenzothiophenyl, benzofuranyl, dibenzofuranyl, pyrrolyl, pyridinyl, pyrimidinyl, pyrazinyl, pyridazinyl, triazinyl, tetrazinyl, imidazolyl, pyrazolyl, indolyl, carbazolyl, benzocarbazolyl, dibenzocarbazolyl, indolocarbazolyl, indenocarbazolyl, benzofurano-carbazolyl, benzothieno-carbazolyl, quinolinyl, iso-quinolinyl, phthalazinyl, quinoxalinyl, cinnolinyl, quinazolinyl, benzoquinolinyl, benzo iso-quinolinyl, benzoquinazolinyl, spiro-carbazolyl and benzoquinoxalinyl.

$R_1$ may be selected from the group consisting of spiro-fluorenyl, phenyl, biphenyl, and $R_2$ may be selected from the group consisting of hydrogen, carbazole and fused carbazole. In this instance, the carbazole or the fused carbazole may be substituted by phenyl or biphenyl, and the fused ring of the fused carbazole may include oxygen atom or sulfur atom.

Each of L1 and L2 may be an aromatic linker. For example, each of L1 and L2 may be independently selected from the group consisting of substituted or non-substituted C5 to C30 arylene group, substituted or non-substituted C4 to C30 heteroarylene group, substituted or non-substituted C6 to C30 arylalkylene group, substituted or non-substituted C6 to C30 hetero-arylalkylene group, substituted or non-substituted C6 to C30 aryloxylene group and substituted or non-substituted C6 to C30 hetero-aryloxylene group.

Each of L1 and L2 may be independently selected from the group consisting of phenylene, biphenylene, terphenylene, tetraphenylene, indenylene, naphthylene, azulenylene, indacenylene, acenaphthylene, fluorenylene, spirofluorenylene, phenalenylene, phenanthrenylene, anthracenylene, fluoranthrenylene, triphenylenylene, pyrenylene, chrysenylene, naphthacenylene, picenylene, perylenylene, pentaphenylene, hexacenylene, pyrrolylene, imidazolylene, pyrazolylene, pyridinylene, pyrazinylene, pyrimidinylene, pyridazinylene, isoindolylene, indolylene, indazolylene, purinylene, quinolinylene, isoquinolinylene, benzoquinolinylene, phthalazinylene, naphthyridinylene, quinoxalinylene, quinazolinylene, benzo-isoquinolinylene, benzoquinazolinylene, benzoquinoxalinylene, cinnolinylene, phenanthridinylene, acridinylene, phenanthrolinylene, phenazinylene, benzoxazolylene, benzimidazolylene, furanylene, benzofuranylene, thiophenylene, benzothiophenylene, thiazolylene, isothiazolylene, benzothiazolylene, isoxazolylene, oxazolylene, triazolylene, tetrazolylene, oxadiazolylene, triazinylene, dibenzofuranylene, dibenzothiophenylene, carbazolylene, benzocarbazolylene, dibenzocarbazolylene, indolocarbazolylene, indenocarbazolylene, imidazopyrimidinylene and imidazopyridinylene.

X1 and X2 or X2 and X3 may form a fused-ring, e.g., a C4 to C30 homo fused-ring or a C4 to C30 hetero fused-ring, connected to the carbazole core. In this instance, when a number of the fused-ring by X1 and X2 or X2 and X3 is increased, the conjugation length of the organic compound is increased such that the energy band gap of the organic compound is decreased. Accordingly, the number of fused-ring may be 1 or 2.

The fused-ring by X1 and X2 or X2 and X3 may be one of a homo fused-ring, such as benzene ring, naphthalene ring, pentalene ring, indene ring, azulene ring or heptalene ring, and a hetero fused ring, such as pyrrole ring, furane ring, thiophene ring, imidazole ring, pyrazole ring, pyridine ring, (dihydro) oxazole ring, thiazole ring, oxadiazole ring, diazole ring, triazine ring, azepine ring, pyrazine ring, pyrimidine ring, pyridazine ring, quinoline ring, isoquinoline ring, indole ring, indolizine ring, pteridine ring, cinnoline ring, quinazoline ring, quinoxaline ring, quinazoline ring, quinolizine ring, naphthrydine ring, indazole ring, furine ring, pyrrolizine ring, phthalazine ring, pyran ring, benzofurane ring, chromene ring, isochromene ring or benzothiophene ring.

Since the organic compound of the invention includes a carbazole moiety, on which a side ring is fused, the thermal stability of the organic compound is increased. In addition, an aromatic ring is directly or indirectly connected to the ring-fused carbazole moiety, and the hole transporting property and/or the electron transporting property of the organic compound are improved by the aromatic ring. Accordingly, the organic light emitting diode including the organic compound has advantages in the emitting efficiency and the color purity, and the charge injection property is improved such that the driving voltage is reduced. Moreover, in the organic light emitting diode including the organic compound, the charge balance in an organic layer is improved or optimized. As a result, the emission at the interface between the EML and adjacent layer is prevented such that the emitting efficiency and the lifetime are improved.

The organic compound may have excellent hole injection property or transporting property and good thermal stability. This organic compound is referred to as a first organic compound. The first organic compound may be used as a P-type host in an organic layer of the organic light emitting diode. The first organic compound is represented by Formula 2.

[Formula 2]

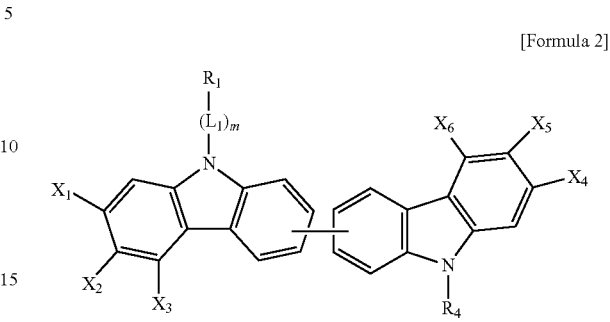

In Formula 2, each of R3 and R4 may be independently selected from the group consisting of hydrogen, deuterium, tritium, C5 to C30 aryl group, substituted or non-substituted C5 to C30 heteroaryl group, substituted or non-substituted C6 to C30 arylalkyl group, substituted or non-substituted C6 to C30 hetero-arylalkyl group, non-substituted C6 to C30 aryloxyl group and substituted or non-substituted C6 to C30 hetero-aryloxyl group, and X5 with one of X4 and X6 forms a C4 to C30 homo fused-ring or a C4 to C30 hetero fused-ring. Alternatively, each of X4 to X6 is independently connected to the carbon atom of the carbazole core without forming the fused-ring. In this instance, each of X4 to X6 may be hydrogen, deuterium, tritium, substituted or non-substituted C1 to C20 alkyl group, substituted or non-substituted C1 to C20 alkoxy group, substituted or non-substituted C5 to C30 aryl group or substituted or non-substituted C5 to C30 heteroaryl group. Each of L1, m, X1, X2 and X3 are same as defined in Formula 1.

In Formula 2, each of R3 and R4 is homo aryl group or heteroaryl group each having excellent hole transporting property. For example, each of R3 and R4 may be selected from the group consisting of phenyl, biphenyl, terphenyl, where each benzene ring is connected in a meta-position or a para-position, fluorenyl, spiro-fluorenyl, carbazolyl, benzocarbazolyl, dibenzocarbazolyl, indolocarbazolyl, indenocarbazolyl, benzofurano-carbazolyl, benzothieno-carbazolyl and spiro-carbazolyl.

X4 and X5 or X5 and X6 may form a fused-ring, e.g., a C4 to C30 homo fused-ring or a C4 to C30 hetero fused-ring, connected to the carbazole core. In this instance, when a number of the fused-ring by X4 and X5 or X5 and X6 is increased, the conjugation length of the organic compound is increased such that the energy band gap of the organic compound is decreased. Accordingly, the number of fused-ring may be 1 or 2.

The fused-ring by X4 and X5 or X5 and X6 may be one of a homo fused-ring, such as benzene ring, naphthalene ring, pentalene ring, indene ring, azulene ring or heptalene ring, and a hetero fused ring, such as pyrrole ring, furane ring, thiophene ring, imidazole ring, pyrazole ring, pyridine ring, (dihydro) oxazole ring, thiazole ring, oxadiazole ring, diazole ring, triazine ring, azepine ring, pyrazine ring, pyrimidine ring, pyridazine ring, quinoline ring, isoquinoline ring, indole ring, indolizine ring, pteridine ring, cinnoline ring, quinazoline ring, quinoxaline ring, quinazoline ring, quinolizine ring, naphthrydine ring, indazole ring, furine ring, pyrrolizine ring, phthalazine ring, pyran ring, benzofurane ring, chromene ring, isochromene ring or benzothiophene ring.

Since the first organic compound of the invention has an excellent hole transporting property, the first organic compound may be used as the P-type host in the EML. For example, the first organic compound of Formula 2, may be included in at least one of the EIL, the ETL, the EML and the EBL. Due to the first organic compound in the above organic layer, the hole injection and/or hole transporting property are improved, and the charge balance is improved. In addition, due to the first organic compound in the EBL, the exciton is trapped in the EML. As a result, the organic light emitting diode including the first organic compound has advantages in the driving voltage, the emitting efficiency, the lifetime, the thermal stability and the color purity.

The first organic compound of the present invention may be one of the compounds in Formula 3.

[Formula 3]

PPH1

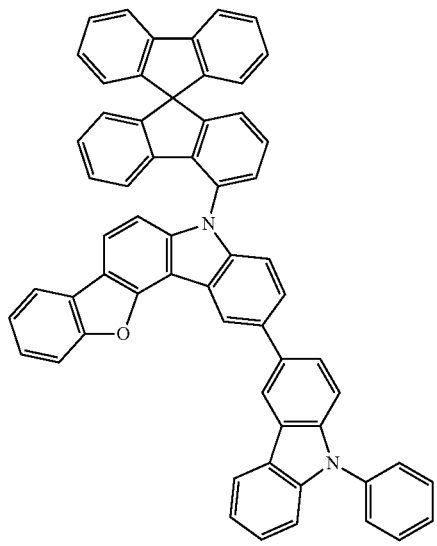

PPH2

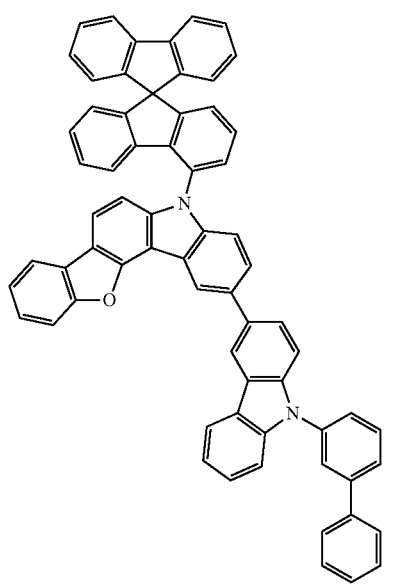

PPH3

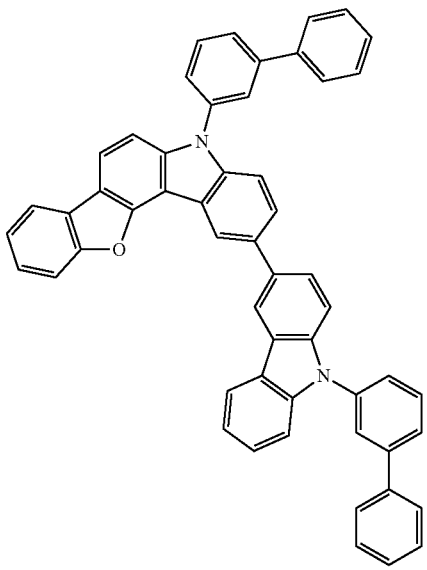

PPH4

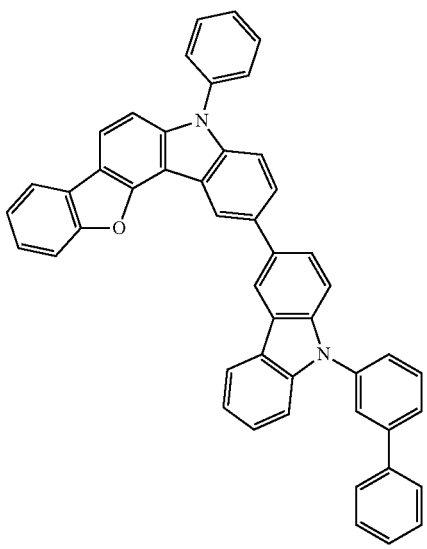

PPH5
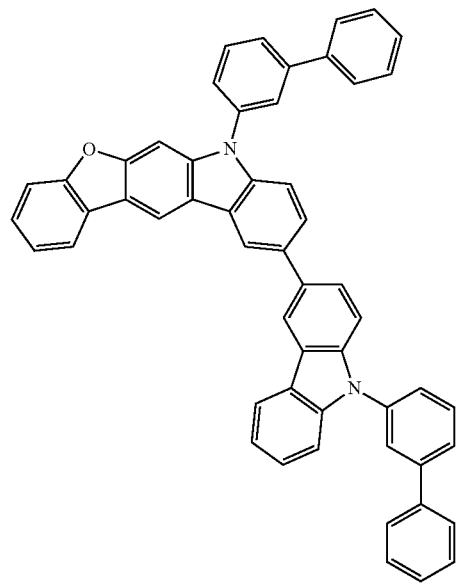
PPH6
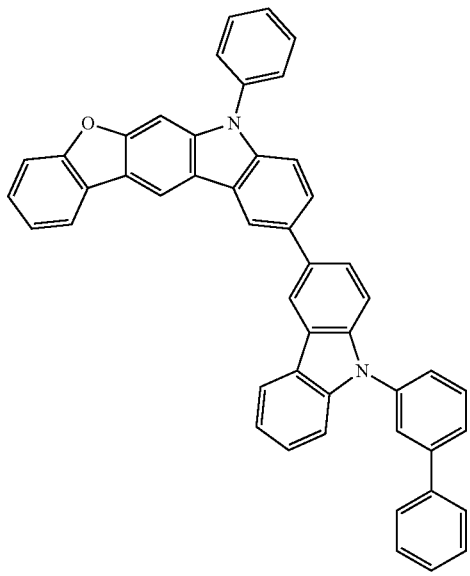
PPH7
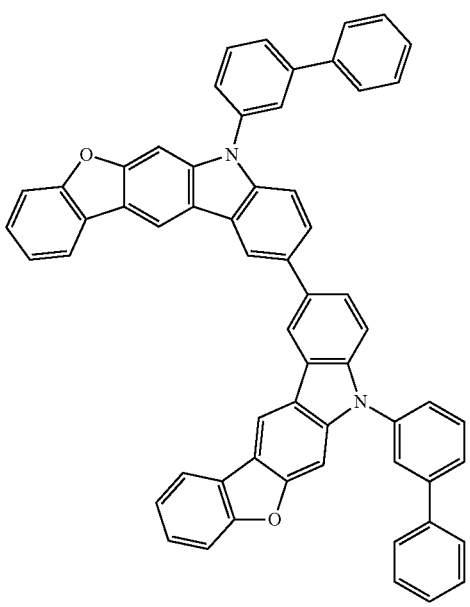
PPH8
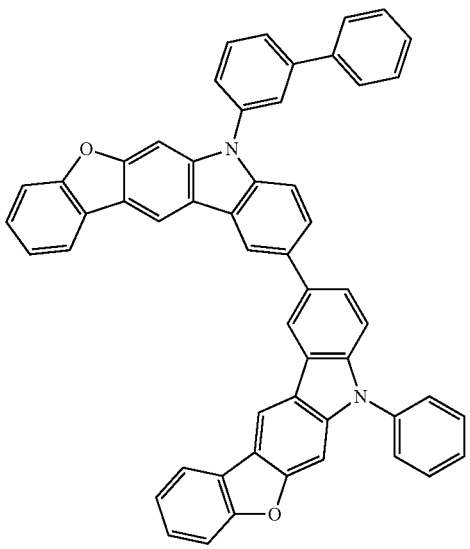

PPH9
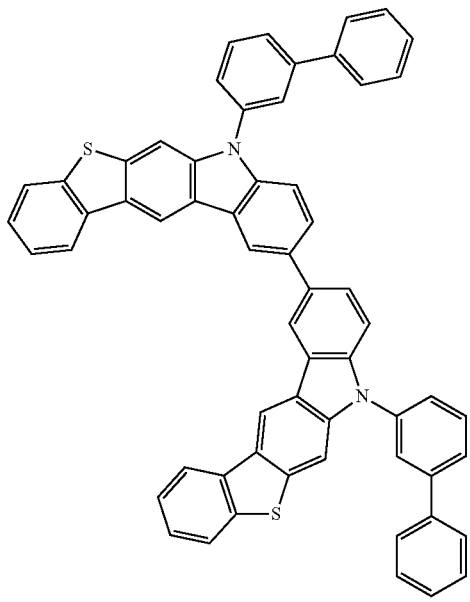
PPH10
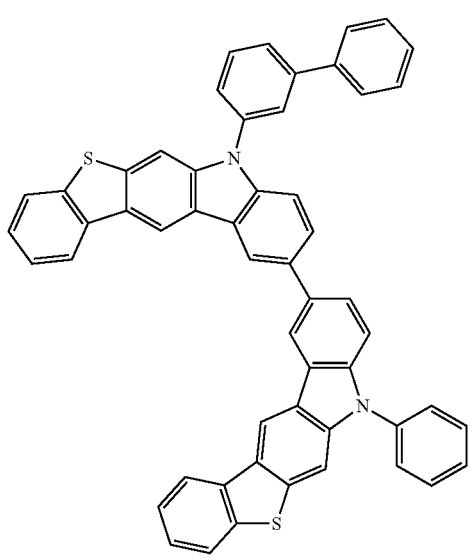
PPH11
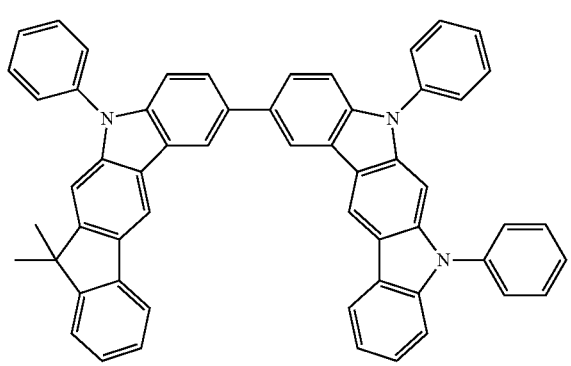
PPH12
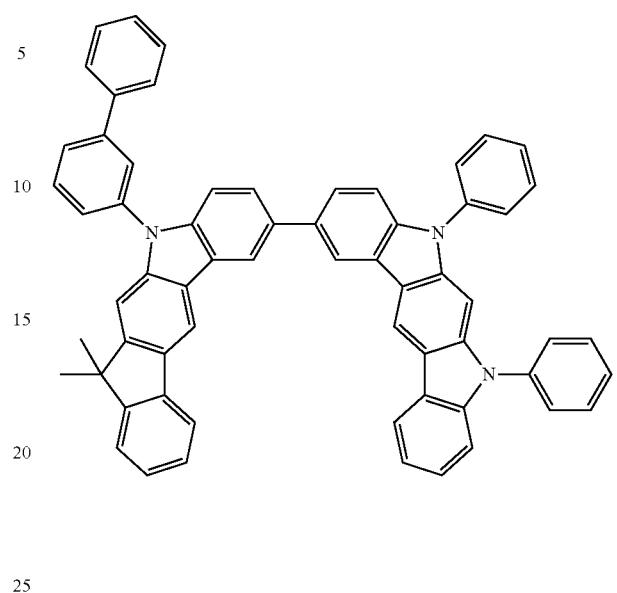
PPH13
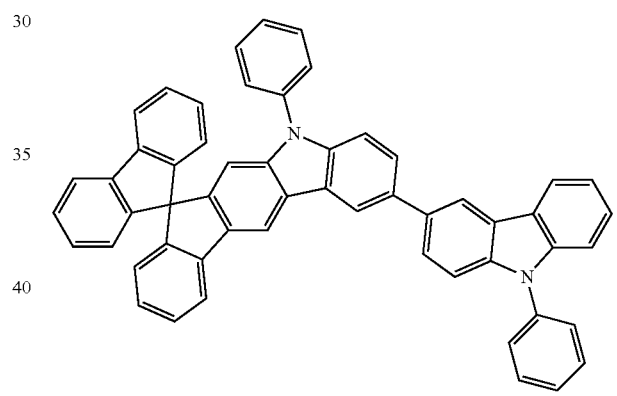
PPH14
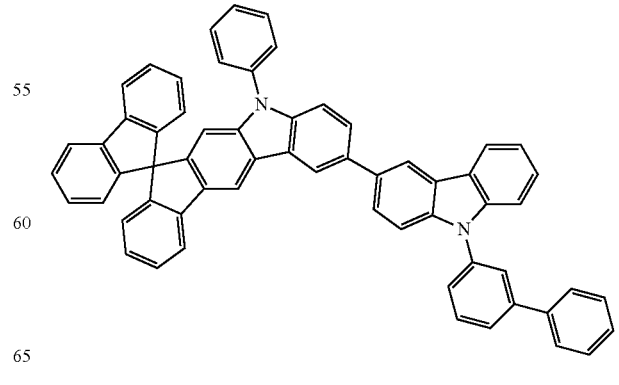

PPH15

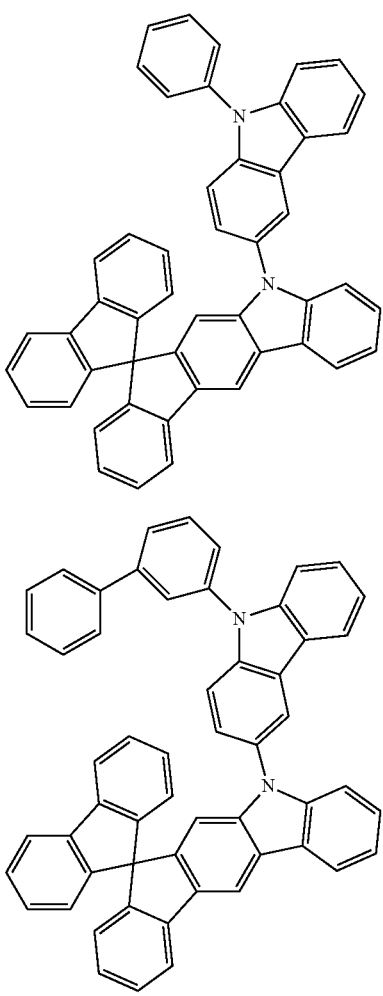

PPH16

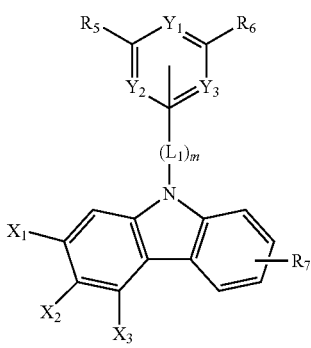
[Formula 4a]

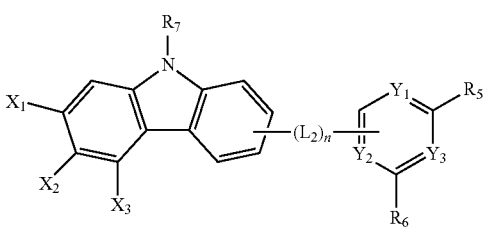
[Formula 4b]

In Formulas 4a and 4b, each of $R_5$ to $R_7$ may be independently selected from the group consisting of hydrogen, deuterium, tritium, $C_5$ to $C_{30}$ aryl group, substituted or non-substituted $C_5$ to $C_{30}$ heteroaryl group, substituted or non-substituted $C_6$ to $C_{30}$ arylalkyl group, substituted or non-substituted $C_6$ to $C_{30}$ hetero-arylalkyl group, non-substituted $C_6$ to $C_{30}$ aryloxyl group and substituted or non-substituted $C_6$ to $C_{30}$ hetero-aryloxyl group. Each of $Y_1$ to $Y_3$ is independently N or $CR_8$, and at least one of $Y_1$ to $Y_3$ is N. $R_8$ is selected from the group consisting of hydrogen, deuterium, tritium, $C_5$ to $C_{30}$ aryl group, substituted or non-substituted $C_5$ to $C_{30}$ heteroaryl group, substituted or non-substituted $C_6$ to $C_{30}$ arylalkyl group, substituted or non-substituted $C_6$ to $C_{30}$ hetero-arylalkyl group, non-substituted $C_6$ to $C_{30}$ aryloxyl group and substituted or non-substituted $C_6$ to $C_{30}$ hetero-aryloxyl group. $X_1$ to $X_3$ in Formulas 4a and 4B, $L_1$ and m in Formula 4a and $L_2$ and n in Formula 4b are the same as defined in Formula 1.

When a number of the ring in each of R5 to R7 is increased, the conjugation length of the organic compound is increased such that the energy band gap of the organic compound is decreased. Accordingly, the number of the ring in each of R5 to R7 may be 1 or 2, and beneficially the number of the ring in each of R6 and R7 may be 1.

For example, each of R5 to R7 may be 5-numbered atom ring to 7-numbered atom ring, and beneficially 6-numbered atom ring. Each of R5 to R7 may be independently selected from the group consisting of phenyl, pyrrolyl, imidazolyl, pyrazolyl, pyridinyl, pyrazinyl, pyrimidinyl, pyridazinyl, furanyl and thiophenyl.

A number of the ring in L1 of Formula 4a and L2 of Formula 4b is increased, the conjugation length of the organic compound is increased such that the energy band gap of the organic compound is decreased. Accordingly, the number of the ring in in L1 of Formula 4a and L2 of Formula 4b may be 1 or 2, and beneficially 1. In addition, to improve the charge (i.e., hole or electron) injection and/or transporting property of the second organic compound, each of L1 and L2 may be 5-numbered atom ring to 7-numbered atom ring, and beneficially 6-numbered atom ring. Each of L1 and L2 may be independently selected from the group consisting The first organic compound in Formula 2 or Formula 3 includes a first carbazole moiety, on which a side ring is fused, and a second carbazole moiety, on which one or two side ring may be fused, connected to the first carbazole moiety such that the hole transporting property is improved. The lowest unoccupied molecular orbital (LUMO) of the first organic compound is closer to the vacuum degree (0 ev) than a dopant, or the first organic compound has a wide energy bad gap, i.e., a gap (difference) between the LUMO and the highest occupied molecular orbital (HOMO). In addition, the first organic compound has the triplet energy being greater than the dopant. Accordingly, when the first organic compound is used in the organic layer of the organic light emitting diode, the reverse-transition of the energy, which is transited from the host into the dopant, into the host is prevented such that the emitting efficiency is improved. The first organic compound may be included in at least one of the EIL, the ETL, the EML and the EBL of the organic light emitting diode.

The organic compound may have excellent properties in both hole injection (or transporting) and electron injection (transporting). In addition, the organic compound may have good thermal stability. This organic compound is referred to as a second organic compound. The second organic compound may be used as a N-type host or a bipolar host in an organic layer of the organic light emitting diode. The first organic compound is represented by Formulas 4a or 4b.

of phenyl, pyrrolyl, imidazolyl, pyrazolyl, pyridinyl, pyrazinyl, pyrimidinyl, pyridazinyl, furanyl and thiophenyl.

As shown in Formulas 4a or 4b, in the second organic compound, the 6-atom hetero ring moiety, which has at least one nitrogen atom in the ring, is directly or indirectly connected to the fused carbazole moiety. For example, the 6-atom hetero ring moiety may be pyridine, pyrimidine or triazine, beneficially pyrimidine or triazine to further improve the electron injection property.

Since the second organic compound in Formulas 4a or 4b has excellent hole and electron injection/transporting properties, the second organic compound is used as the N-type host or the bipolar host in the organic layer. For example, the second organic compound may be included in at least one of the EIL, the ETL, the HBL, the HIL, the HTL, the EML and the EBL. Due to the second organic compound in the above organic layer, the hole injection/transporting property and electron injection/transporting property are improved, and the charge balance is improved. As a result, the organic light emitting diode including the second organic compound has advantages in the driving voltage, the emitting efficiency, the lifetime, the thermal stability and the color purity.

The second organic compound of the present invention may be one of the compounds in Formula 5.

[Formula 5]

PNH1

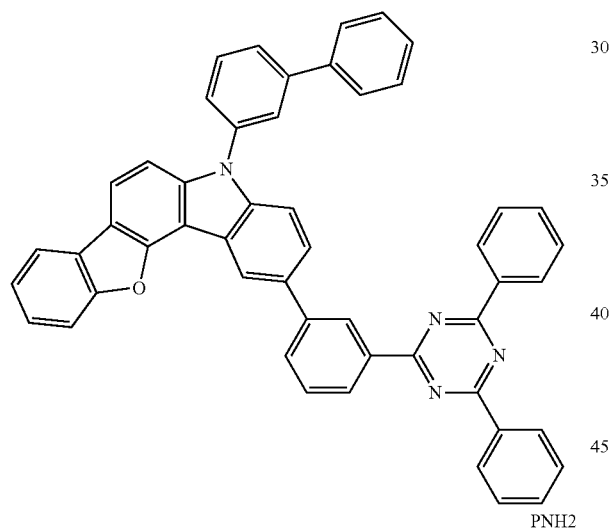

PNH2

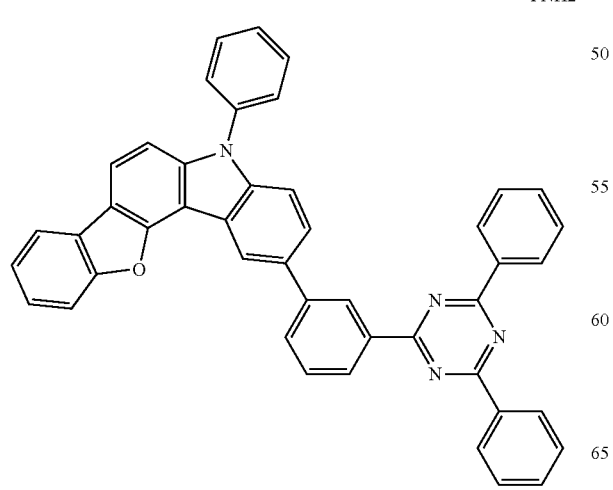

PNH3

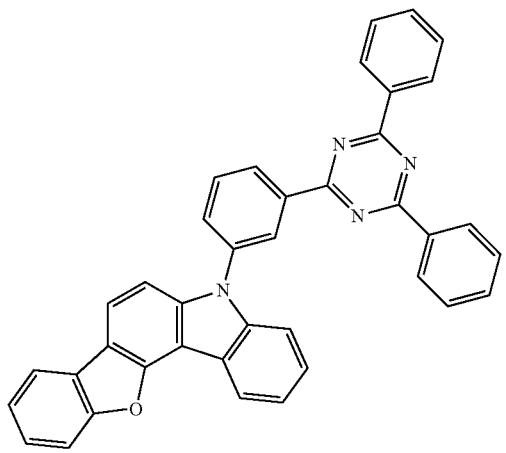

PNH4

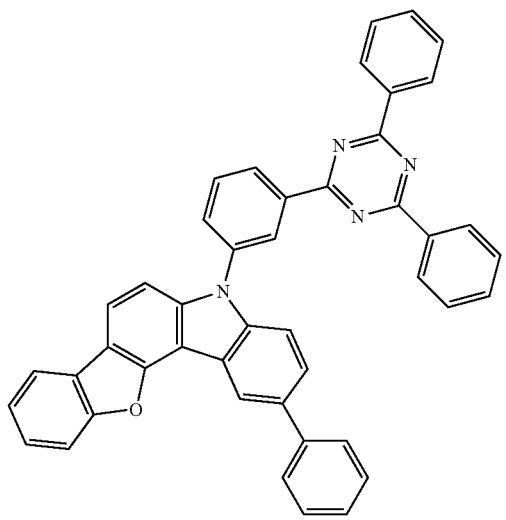

PNH5

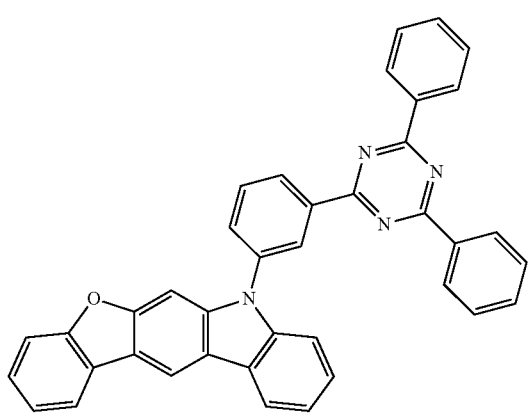

PNH6
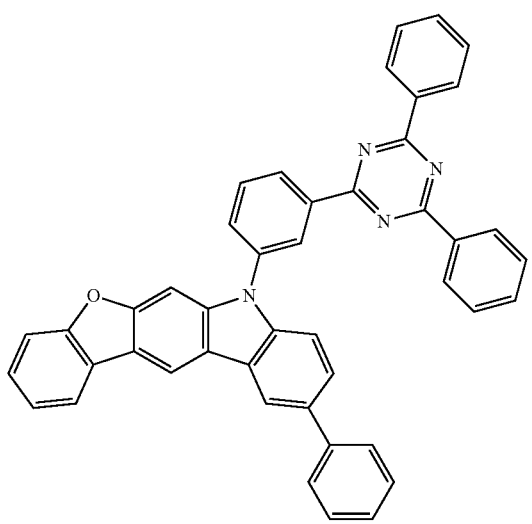
PNH7
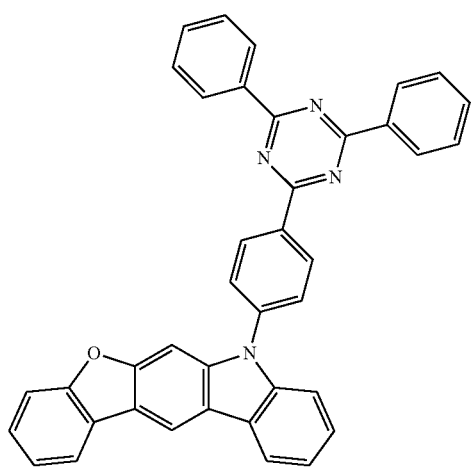
PNH8
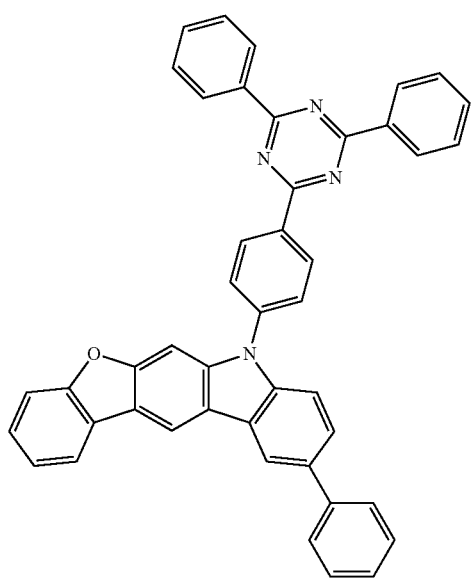
PNH9
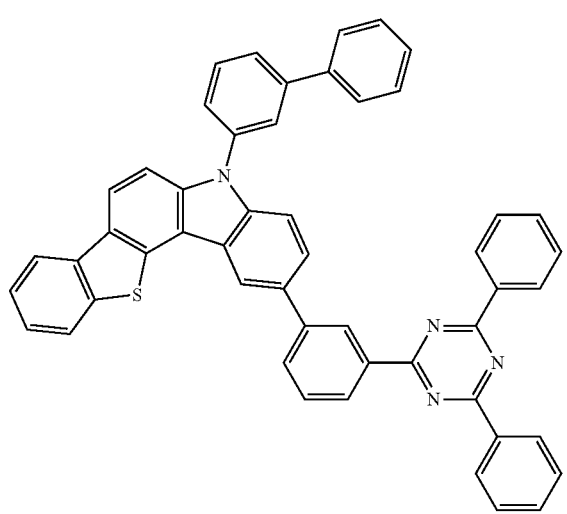
PNH10
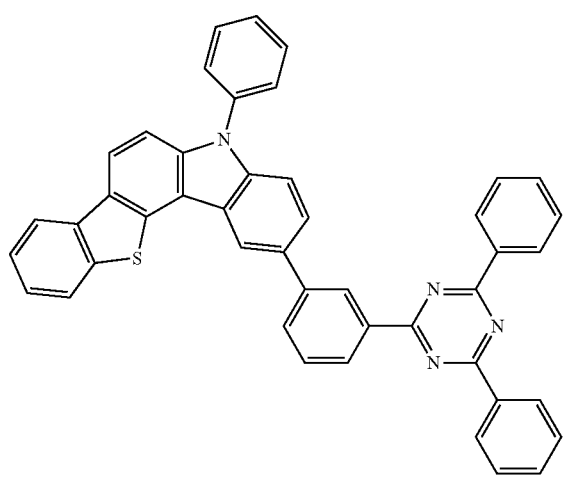
PNH11
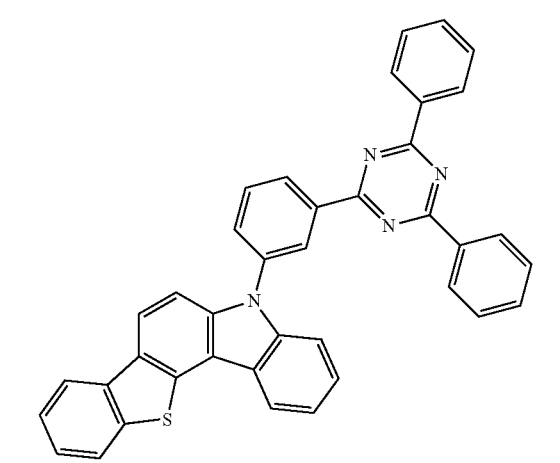

PNH12

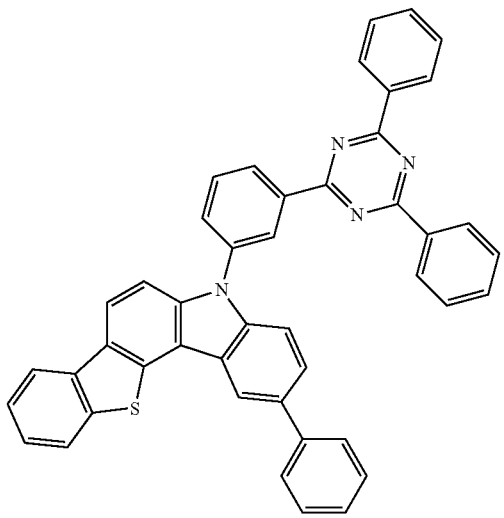

PNH13

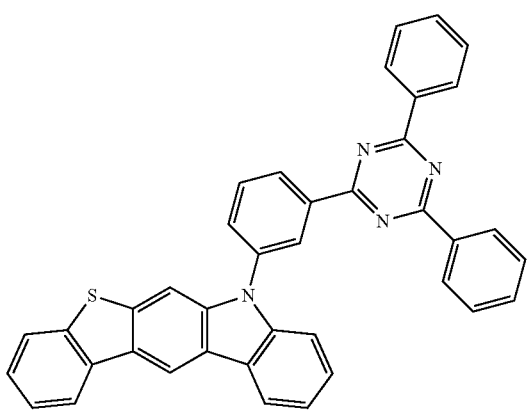

PNH14

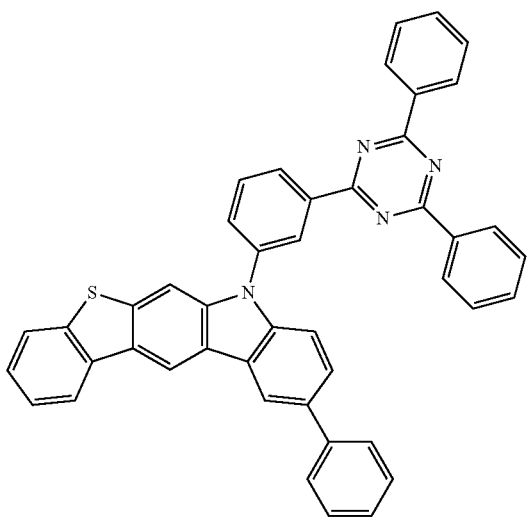

PNH15

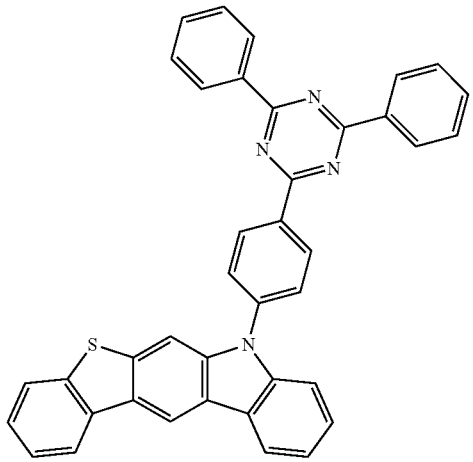

PNH16

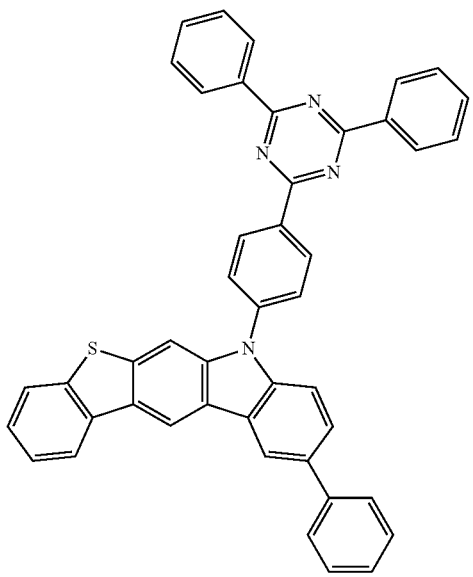

The second organic compound in Formulas 4a, 4b or 5 includes the fused carbazole moiety and the hetero aromatic moiety, which includes at least one atom having rich electron property and is directly or indirectly connected to the fused carbazole moiety, such that the second organic compound has excellent hole injection/transporting property and excellent electron injection/transporting property. The second organic compound in Formulas 4a or 4b may include at least one triazine moiety The LUMO of the second organic compound is smaller (lower) than that of the dopant, and the second organic compound has a wide energy bad gap, i.e., a gap (difference) between the LUMO and the HOMO. In addition, the second organic compound has the triplet energy being greater than the dopant. Accordingly, the second organic compound may be included in at least one of the EIL, the ETL and the HBL as well as at least one of the HIL, the HTL, the EBL and the EML.

Since the organic compound of the present invention has excellent properties in the thermal stability, the durability, the hole injection/transporting property and/or the electron injection/transporting property, the organic compound is used in various organic layer of the organic light emitting diode.

FIG. 1 is a schematic cross-sectional view of an organic light emitting diode according to a first embodiment of the present invention.

As shown in FIG. 1, the organic light emitting diode 100 includes a first electrode 110, a second electrode 120 facing the first electrode 110, an emitting part 130 between the first and second electrodes 110 and 120. The emitting part 130 includes a hole auxiliary layer, which includes an HIL 140 and an HTL 150, an EML 160 and an electron auxiliary layer, which includes an ETL 170 and EIL 180, sequentially stacked on the first electrode 110.

The first electrode 110 as an anode includes a high work function conductive material, e.g., indium-tin-oxide (ITO) or indium-zinc-oxide (IZO).

The second electrode 120 as a cathode includes a low work function conductive material, e.g., aluminum (Al), magnesium (Mg), calcium (Ca), silver (Ag) or their alloy.

The HIL 140 is positioned between the first electrode 110 and the HTL 150. An interface property between the first electrode 110 of an inorganic material and the HTL 150 of an organic material is improved by the HIL 140. For example, the HIL 140 may include one of 4,4',4''-tris(3-methylphenylphenylamino)triphenylamine (MTDATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4''-diamine (NPB or NPD), 1,4,5,8,9,11-hexaazatriphenylenehexacarbonitrile (HATCN), 1,3,5-tris[4-(diphenylamino)phenyl]benzene (TDAPB), poly(3,4-ethylenedioxythiphene)polystyrene sulfonate (PEDOT/PSS), 2,3,5,6-tetrafluoro-7,7,8,8-tetracyanoquinodimethane (F4TCNQ), N-(biphenyl-4-yl)-9,9-dimethyl-N-(4-(9-phenyl-9H-carbazol-3-yl)phenyl)-9H-fluoren-2-amine, a compound of following Formula 6.

[Formula 6]

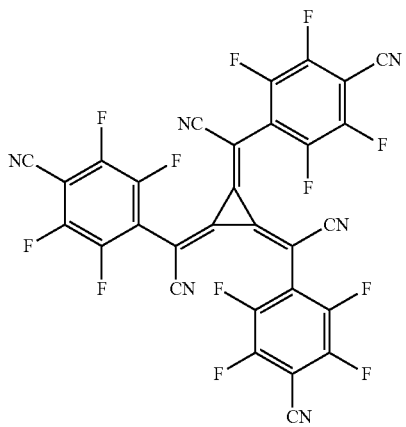

Alternatively, the HIL 140 may include the organic compound of the present invention in Formulas 1 to 5, e.g., the organic compound in above Formulas 2 and 3 or the organic compound in above Formulas 4a to 5.

The HTL 150 is positioned between the first electrode 110 and the EML 160 to be adjacent to the EML 160. Namely, the HTL 150 is positioned between the HIL 140 and the EML 160. For example, the HTL 150 may include aromatic amine compound such as N,N-diphenyl-N,N'-bis(3-methylphenyl)-1,1'-biphenyl-4,4'-diamine (TPD), NPD, 4,4'-bis(N-carbazolyl)-1,1'-biphenyl (CBP), N-(biphenyl-4-yl)-9,9-dimethyl-N-(4-(9-phenyl-9H-carbazol-3-yl)phenyl)-9H-fluoren-2-amine or N-(biphenyl-4-yl)-N-(4-(9-phenyl-9H-carbazol-3-yl)phenyl)biphenyl-4-amine.

Alternatively, the HTL 150 may include the organic compound of the present invention in Formulas 1 to 5, e.g., the organic compound in above Formulas 2 and 3 or the organic compound in above Formulas 4a to 5.

To improve the emitting efficiency of the organic light emitting diode 100, the EML 160 may include a host and a dopant. The EML 160 may include the organic compound of the present invention in Formulas 1 to 5. For example, the first organic compound in Formulas 2 or 3 and/or the second organic compound in formulas 4a to 5 may be used as a host in the EML 160.

Namely, one of the first organic compound and the second organic compound may be used in the EML 160. Alternatively, both of the first and second organic compounds may be used in the EML 160. It may be referred to as a two host system or a dual host system. When the first organic compound having excellent hole transporting property and the second organic compound having excellent hole and electron transporting property are used for the EML 150, the charge transporting property is further improved.

In addition, in the two host system, the driving voltage of the organic light emitting diode 100 is lowered. Moreover, the emission is generated in entire region of the EML 160, the emitting efficiency and the lifetime of the organic light emitting diode 100 are improved. Furthermore, by using the dopant having the triplet energy being smaller than the first and second organic compounds, the reverse-transition of the energy, which is transited from the host into the dopant, into the host is prevented such that the emitting efficiency is improved. Namely, the charge is efficiently transferred from the host into the dopant.

In the two host system, the first host may have a weight % of about 20 to 80 with respect to a total of the first and second host, beneficially 30 to 70, and more beneficially 40 to 60. By controlling the ratio of the first host to the second host, the charge balance in the EML 160 is also controlled or improved such that the emitting efficiency and the lifetime of the organic light emitting diode 100 are increased.

The EML 160 may further include a dopant. For example, the EML 160 may include a phosphorescent dopant. The phosphorescent dopant may be a metal complex, e.g., iridium (Ir), osmium (Os), copper (Cu) or platinum (Pt), but it is not limited thereto. The phosphorescent may be an Ir complex or a Pt complex, and preferably Ir complex. To efficiently transfer the charge from the host into the dopant and prevent the reverse-transition of the energy from the dopant into the host, the dopant may have an energy band gap between that of the first host (first organic compound) and that of the second host (second organic compound) and a triplet energy being smaller than that of each of the first and second hosts.

For example, the dopant in the EML 160 may be a material represented by Formulas 7 or 8, but it is not limited thereto.

[Formula 7]

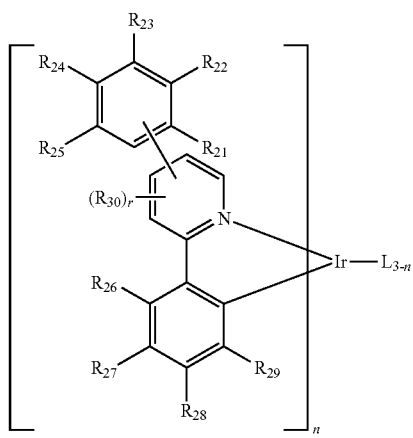

[Formula 8]

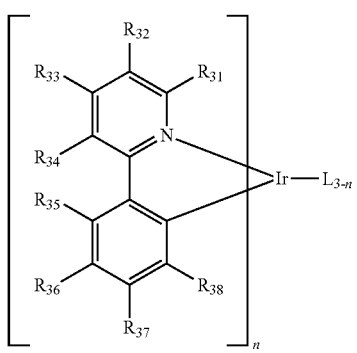

[Formula 9]

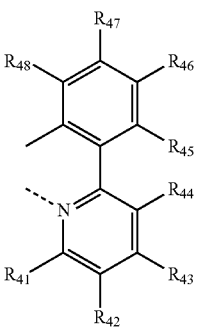

In Formula 9, each of $R_{41}$ to $R_{48}$ may be independently selected from the group consisting of hydrogen, deuterium, tritium, halogen, substituted or non-substituted $C_1$ to $C_{30}$ alkyl group, cyano group, substituted or non-substituted $C_3$ to $C_{30}$ cyclo-alkyl group, substituted or non-substituted $C_3$ to $C_{30}$ hetero cyclo-alkyl group, substituted or non-substituted $C_5$ to $C_{30}$ aryl group, substituted or non-substituted $C_5$ to $C_{30}$ heteroaryl group, substituted or non-substituted $C_6$ to $C_{30}$ arylalkyl group, substituted or non-substituted $C_6$ to $C_{30}$ hetero-arylalkyl group, substituted or non-substituted $C_6$ to $C_{30}$ aryloxyl group and substituted or non-substituted $C_6$ to $C_{30}$ hetero-aryloxyl group, or adjacent two of $R_{41}$ to $R_{48}$ may form a fused aromatic ring of $C_5$ to $C_{30}$.

The dopant in the EML 160 may be one of the compounds in Formula 10.

In Formula 7, each of R21 to R29 may be independently selected from the group consisting of hydrogen, deuterium, tritium, halogen, substituted or non-substituted C1 to C30 alkyl group, cyano group, substituted or non-substituted C3 to C30 cyclo-alkyl group, substituted or non-substituted C3 to C30 hetero cyclo-alkyl group, substituted or non-substituted C5 to C30 aryl group, substituted or non-substituted C5 to C30 heteroaryl group, substituted or non-substituted C6 to C30 arylalkyl group, substituted or non-substituted C6 to C30 hetero-arylalkyl group, substituted or non-substituted C6 to C30 aryloxyl group and substituted or non-substituted C6 to C30 hetero-aryloxyl group, R 30 may be selected from the group consisting of hydrogen, deuterium, tritium and substituted or non-substituted C1 to C30 alkyl group, and "r" is an integer of 1 to 4.

In Formula 8, each of R31 to R38 may be independently selected from the group consisting of hydrogen, deuterium, tritium, halogen, substituted or non-substituted C1 to C30 alkyl group, cyano group, substituted or non-substituted C3 to C30 cyclo-alkyl group, substituted or non-substituted C3 to C30 hetero cyclo-alkyl group, substituted or non-substituted C5 to C30 aryl group, substituted or non-substituted C5 to C30 heteroaryl group, substituted or non-substituted C6 to C30 arylalkyl group, substituted or non-substituted C6 to C30 hetero-arylalkyl group, substituted or non-substituted C6 to C30 aryloxyl group and substituted or non-substituted C6 to C30 hetero-aryloxyl group, or adjacent two of R31 to R38 may form fused aromatic ring of C5 to C30. In Formulas 7 and 8, "n" is an integer of 1 to 3, and L is represented by Formula 9.

[Formula 10]

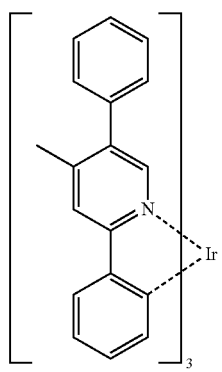

D1

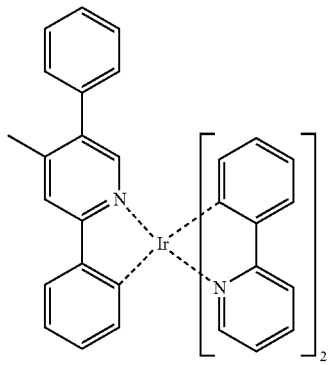

D2

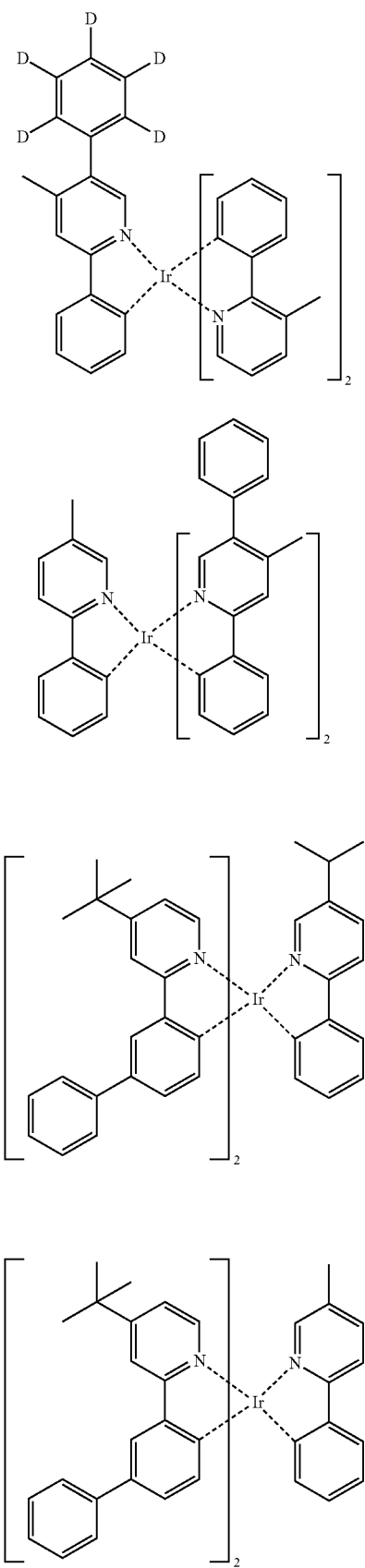
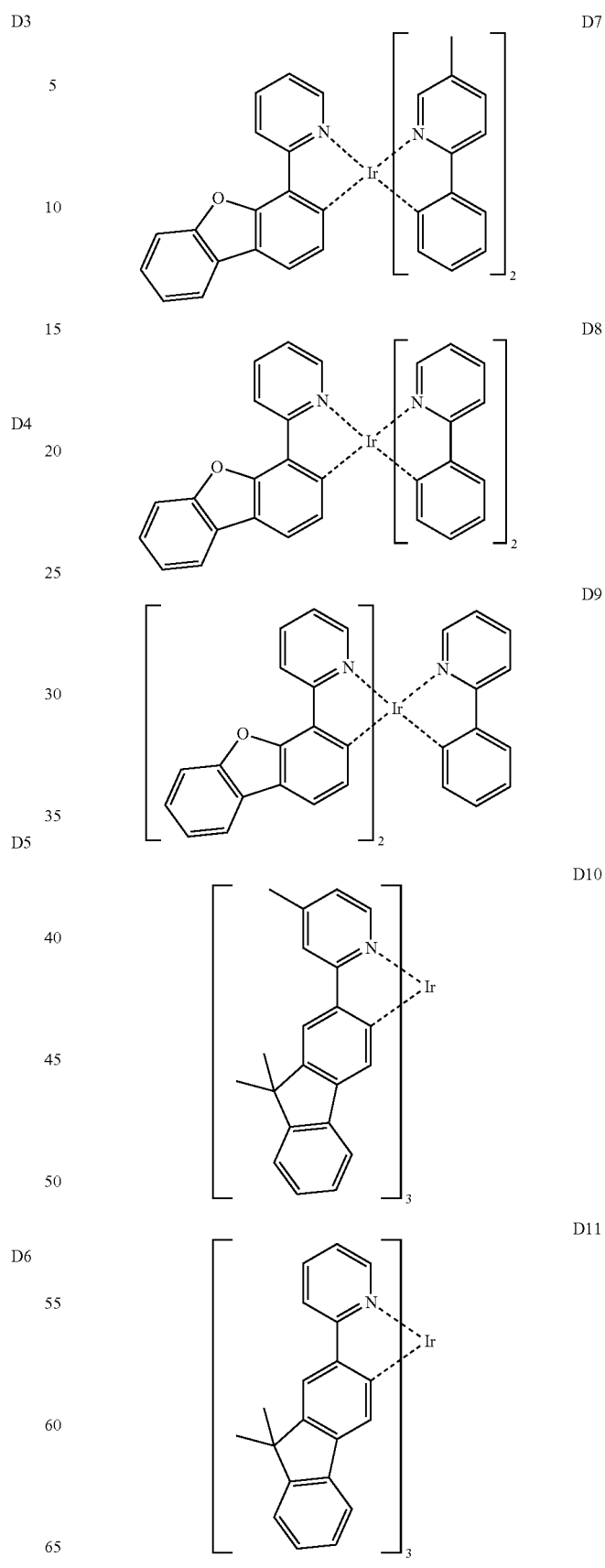

-continued

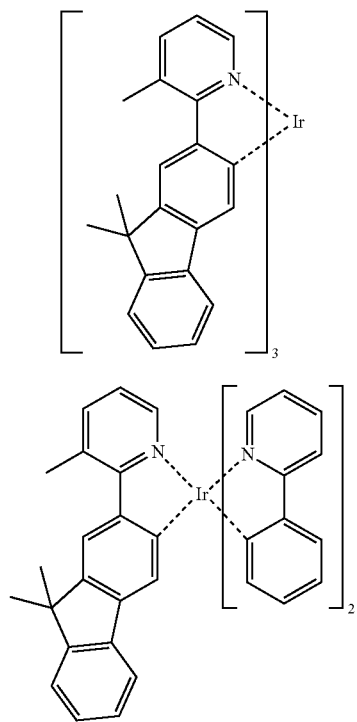

D12

D13

The dopant may have a weight % of 0.1 to 50 with respect to a total of the first and second organic compounds in the EML 160, and preferably about 1 to 20 weight %.

The ETL 170 and the EIL 180 may be sequentially stacked on the EML 160. The ETL 170 includes a material having high electron mobility such that the electron is provided into the EML 160.

For example, the ETL 170 may include one of tris-(8-hydroxyquinoline aluminum (Alq3), 2-biphenyl-4-yl-5-(4-t-butylphenyl)-1,3,4-oxadiazole (PBD), spiro-PBD, Liq, 2-[4-(9,10-Di-2-naphthalenyl-2-anthracenyl)phenyl]-1-phenyl-1H-benzimidazol, 3-(biphenyl-4-yl)-5-(4-tertbutylphenyl)-4-phenyl-4H-1,2,4-triazole (TAZ), 4,7-diphenyl-1,10-phenanthroline (Bphen), tris(phenylquinoxaline (TPQ), 1,3,5-tris(N-phenylbenzimiazole-2-yl)benzene (TPBI), or a material of Formula 11, but it is not limited thereto.

[Formula 11]

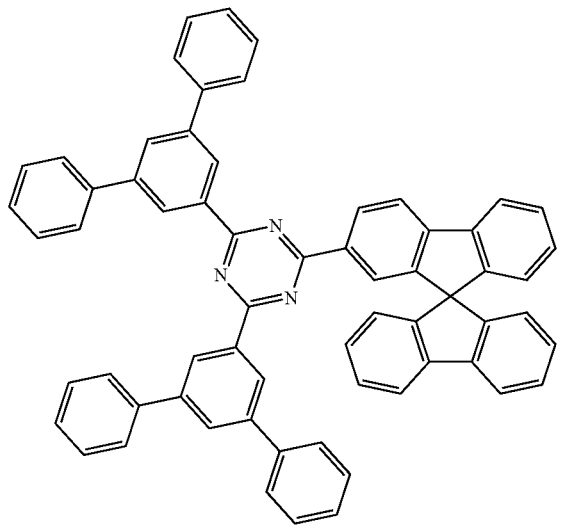

The ETL 170 may include the second organic compound in Formulas 4a to 5.

The EIL 180 is positioned between the ETL 170 and the second electrode 120, and the property of the second electrode 120 is enhanced by the EIL 180 such that the lifetime of the organic light emitting diode 100 is further improved. For example, the EIL 180 may include an alkali halide compound, e.g., LiF, CsF, NaF or BaF2, or an organometallic compound, e.g., lithium quinolate (Liq), lithium benzoate or sodium stearate, but it is not limited thereto. The EIL 180 may include the second organic compound in Formulas 4a to 5.

When each of the ETL 170 and the EIL 180 include the organic compound of the present invention, i.e., the second organic compound, alkali metal or alkali earth metal as a dopant may be doped into ETL 170 and/or the EIL 180 such that the electron transporting and/or injection property is further improved. The alkali metal or the alkali earth metal may have a doping ration of about 1 to 20 weight % with respect to the second organic compound, but it is not limited thereto. For example, the dopant may be one of Li, Na, K, Cs, Mg, Sr, Ba and Ra, but it is not limited thereto.

The organic light emitting diode 100 includes the HIL 140, the HTL 150, the EML 160, the ETL 170 and the EIL 180 between the first and second electrodes 110 and 120, and the organic compound of the present invention may be used in at least one of the above layers with or without a dopant.

As mentioned above, since the organic compound of the invention includes the carbazole moiety, on which a side ring is fused, the thermal stability of the organic compound is increased. In the first organic compound, two fused carbazole moieties are connected to each other such that the first organic compound has excellent hole transporting property. On the other hand, in the second organic compound, a hetero aromatic ring, which includes a nitrogen atom, is directly or indirectly connected to a fused carbazole moiety such that the organic compound has excellent electron transporting property as well as excellent hole transporting property. Accordingly, when the organic compound of the present invention is included in at least one organic layer of the organic light emitting diode 100, the charge is efficiently transferred such that the driving voltage of the organic light emitting diode 100 is reduced. For example, when the first and second organic compounds are included in the EML 160, the balance of the charges is improved such that the emission is generated in an entire region of the EML 160. As a result, the emission efficiency and the lifetime are improved.

Figure 2:
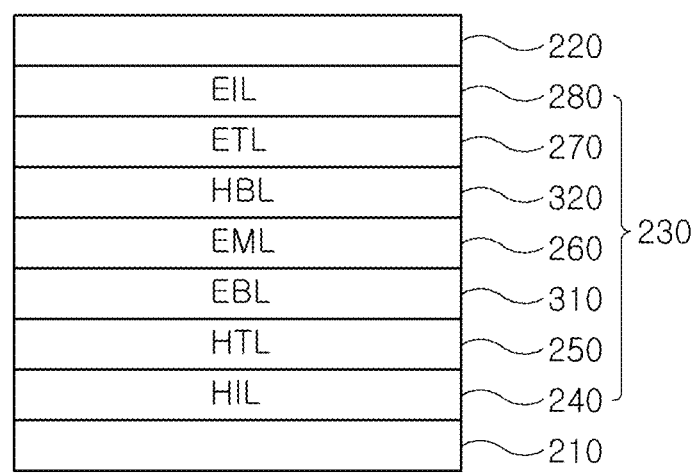
FIG. 2 is a schematic cross-sectional view of an organic light emitting diode according to a second embodiment of the present invention.

FIG. 2 is a schematic cross-sectional view of an organic light emitting diode according to a second embodiment of the present invention.

As shown in FIG. 2, the organic light emitting diode 200 includes a first electrode 210, a second electrode 220 facing the first electrode 210, an emitting part 230 between the first and second electrodes 210 and 220. The emitting part 230 includes a hole auxiliary layer, which includes an HIL 240 and an HTL 250, an electron blocking layer (EBL) 310, an EML 260, a hole blocking layer (HBL) 320 and an electron auxiliary layer, which includes an ETL 270 and EIL 280, sequentially stacked on the first electrode 210.

The first electrode 210 as an anode includes a high work function conductive material, e.g., indium-tin-oxide (ITO) or indium-zinc-oxide (IZO).

The second electrode 220 as a cathode includes a low work function conductive material, e.g., aluminum (Al), magnesium (Mg), calcium (Ca), silver (Ag) or their alloy.

The HIL 240 is positioned between the first electrode 210 and the HTL 250. An interface property between the first electrode 210 of an inorganic material and the HTL 250 of an organic material is improved by the HIL 240. For example, the HIL 240 may include one of MTDATA, CuPc, TCTA, NPB, HATCN, TDAPB, PEDOT/PSS and the compound of above Formula 6.

Alternatively, the HIL 240 may include the organic compound of the present invention in Formulas 1 to 5, e.g., the organic compound in above Formulas 2 and 3 or the organic compound in above Formulas 4a to 5.

The HTL 250 is positioned between the first electrode 210 and the EML 260 to be adjacent to the EML 260. Namely, the HTL 250 is positioned between the HIL 240 and the EML 260. For example, the HTL 250 may include aromatic amine compound such as TPD, NPD, CBP, N-(biphenyl-4-yl)-9,9-dimethyl-N-(4-(9-phenyl-9H-carbazol-3-yl)phenyl)-9H-fluoren-2-amine or N-(biphenyl-4-yl)-N-(4-(9-phenyl-9H-carbazol-3-yl)phenyl)biphenyl-4-amine.

Alternatively, the HTL 250 may include the organic compound of the present invention in Formulas 1 to 5, e.g., the organic compound in above Formulas 2 and 3 or the organic compound in above Formulas 4a to 5.

When the hole is migrated toward the second electrode 220 or the electron is migrated toward the first electrode 210 beyond the EML 260, the lifetime and the emitting efficiency of the organic light emitting diode may be decreased. To prevent this problem, the organic light emitting diode of the present invention may include an exciton blocking layer at an upper side or a lower side of the EML 260.

For example, the EBL 310 is formed between the HTL 250 and the EML 260 to control or block the migration of the electron. The EML 310 may include one of 4,4′,4″-Tris (carbazol-9-yl)-triphenylamine (TCTA) or N-(biphenyl-2-yl)-N-(9,9-dimethyl-9H-fluoren-2-yl)-9,9′-spirobi[fluoren]-2-amine. Alternatively, the EBL 310 may include the organic compound of the present invention in Formulas 1 to 3, e.g., the organic compound in above Formulas 2 and 3.

To improve the emitting efficiency of the organic light emitting diode 200, the EML 260 may include a host and a dopant. The EML 260 may include the organic compound of the present invention in Formulas 1 to 5. For example, the first organic compound in Formulas 2 or 3 and/or the second organic compound in formulas 4a to 5 may be used as a host in the EML 260.

The dopant in the EML 260 may be a phosphorescent dopant and may have a triplet energy being smaller than that of each of the first and second organic compounds. For example, the dopant in the EML 260 may be a material represented by above Formulas 7 to 9. In this instance, the dopant may have a weight % of 0.1 to 50 with respect to a total of the first and second organic compounds in the EML 260, and preferably about 1 to 20 weight %.

The HBL 320 is positioned between the EML 260 and the ETL 270 to block the migration of the hole between the EML 260 and the ETL 270. The HBL 320 may include a derivative compound of oxadiazole, triazole, phenanthroline, benzoxazole, benzothiazole, benzimidazole or triazine. For example, the HBL 320 may include a material having a relatively low highest occupied molecular orbital (HOMO), such as 2,9-dimethyl-4,7-diphenyl-1,10-phenanthroline (BCP), bis(2-methyl-8-quinolinolato)(4-phenylphenolato) aluminum (III) (BAlq), Alq3, 2-biphenyl-4-yl-5-(4-t-butyl-phenyl)-1,3,4-oxadiazole (PBD), spiro-PBD, lithium quinolate(Liq) or the material in above Formula 11, but it is not limited thereto.

Alternatively, the HBL 320 may include the second organic compound in above Formulas 4a to 5.

The ETL 270 and the EIL 280 may be sequentially stacked on the EML 260. The ETL 270 includes a material having high electron mobility such that the electron is provided into the EML 260.

For example, the ETL 270 may include a derivative compound of oxadiazole, triazole, phenanthroline, benzoxazole, benzothiazole, benzimidazole or triazine. For example, the HBL 320 may include BAlq, Alq3, PBD, spiro-PBD, Liq, 2-[4-(9,10-Di-2-naphthalenyl-2-anthracenyl)phenyl]-1-phenyl-1H-benzimidazol), TAZ, Bphen, TPQ, TPBI or the material in above Formula 11, but it is not limited thereto.

Alternatively, the ETL 270 may include the second organic compound in above Formulas 4a to 5.

The EIL 280 is positioned between the ETL 270 and the second electrode 220, and the property of the second electrode 220 is enhanced by the EIL 280 such that the lifetime of the organic light emitting diode 200 is further improved. For example, the EIL 280 may include an alkali halide compound, e.g., LiF, CsF, NaF or BaF2, or an organometallic compound, e.g., lithium quinolate (Liq), lithium benzoate or sodium stearate, but it is not limited thereto. The EIL 280 may include the second organic compound in Formulas 4a to 5.

When each of the ETL 270 and the EIL 280 include the organic compound of the present invention, i.e., the second organic compound, alkali metal or alkali earth metal as a dopant may be doped into ETL 270 and/or the EIL 280 such that the electron transporting and/or injection property is further improved.

In comparison to the organic light emitting diode 100, the organic light emitting diode 200 further includes at least one of the EBL 310 under the EML 260 and the HBL 320 on the EML 260.

As mentioned above, since the organic compound of the invention includes the carbazole moiety, on which a side ring is fused, the thermal stability of the organic compound is increased. In the first organic compound, two fused carbazole moieties are connected to each other such that the first organic compound has excellent hole transporting property. On the other hand, in the second organic compound, a hetero aromatic ring, which includes a nitrogen atom, is directly or indirectly connected to a fused carbazole moiety such that the organic compound has excellent electron transporting property as well as excellent hole transporting property.

Accordingly, when the organic compound of the present invention is included in at least one organic layer of the organic light emitting diode 200, the charge is efficiently transferred such that the driving voltage of the organic light emitting diode 200 is reduced. For example, when the first and second organic compounds are included in the EML 260, the balance of the charges is improved such that the emission is generated in an entire region of the EML 260. As a result, the emission efficiency and the lifetime are improved. In addition, since the EBL 310 and the HBL 320 as the exciton blocking layer are included in the organic light emitting diode 200, the organic light emitting diode 200 is driven by low voltage and the emitting efficiency and the lifetime are improved.

Figure 3:
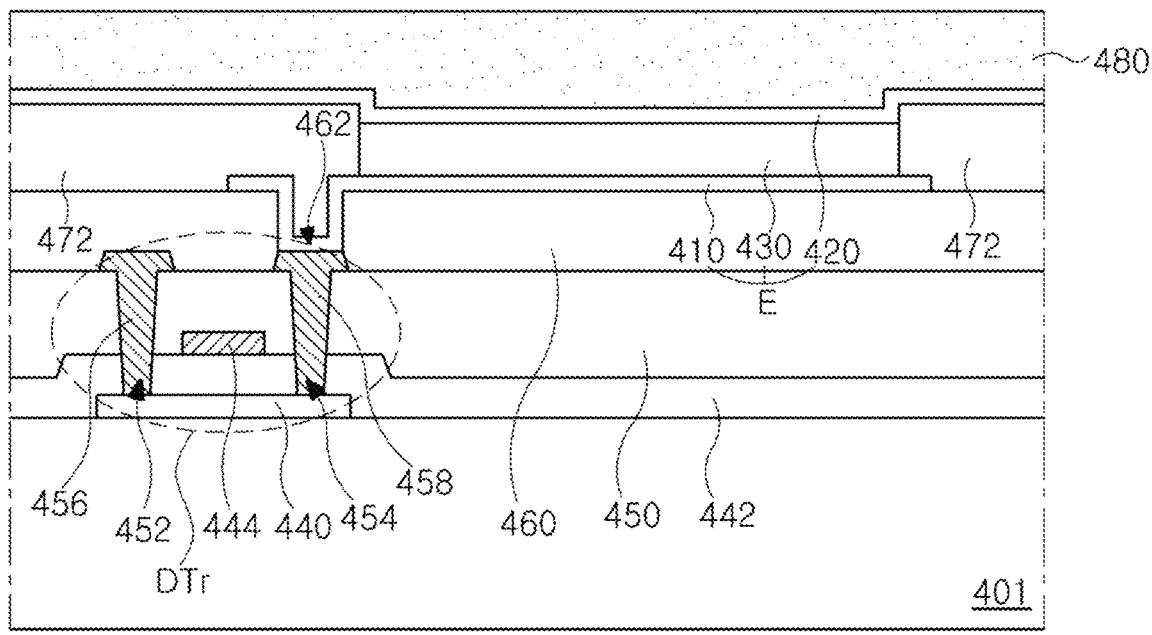
FIG. 3 is a schematic cross-sectional view of an OLED device according to an embodiment of the present invention.

FIG. 3 is a schematic cross-sectional view of an OLED device according to the present invention.

As shown in FIG. 3, the OLED device 400 includes a driving thin film transistor (TFT) Td, a planarization layer 460 covering the driving TFT Td, an organic light emitting diode E on the planarization layer 460 and connected to the driving TFT Td.

The driving TFT Td includes a semiconductor layer 440, a gate electrode 444, a source electrode 456 and a drain electrode 458. The driving TFT Td in FIG. 3 has a coplanar structure.

A substrate 401 may be a glass substrate or a plastic substrate and may serve as a base substrate. The semiconductor layer 440 is formed on the substrate 401. The semiconductor layer 440 may be formed of an oxide semiconductor material. When the semiconductor layer 440 includes the oxide semiconductor material, a light-shielding pattern (not shown) may be formed under the semiconductor layer 440. The light to the semiconductor layer 440 is shielded or blocked by the light-shielding pattern such that thermal degradation of the semiconductor layer 440 can be prevented. On the other hand, when the semiconductor layer 440 includes polycrystalline silicon, impurities may be doped into both sides of the semiconductor layer 440.

A gate insulating layer 442 is formed on the semiconductor layer 440 and over an entire surface of the substrate 401. The gate insulating layer 442 may be formed of an inorganic insulating material such as silicon oxide or silicon nitride.

The gate electrode 444, which is formed of a conductive material, e.g., metal, is formed on the gate insulating layer 442 to correspond to a center of the semiconductor layer 440. For example, the gate electrode 444 may be formed of a low resistance metal such as Al, Al alloy (e.g., AlNd), W, Cu, Cu alloy, Mo, Ag, Ag alloy, Au, Au alloy, Cr, Ti, Ti alloy, MoW, MoTi or Cu—Mo—Ti.

In addition, a gate line (not shown) and a first capacitor electrode (not shown) may be formed on the gate insulating layer 442. The gate line may extends along a first direction, and the first capacitor electrode may be connected to the gate electrode 444. The gate insulating layer 442 in FIG. 3 covers an entire surface of the substrate 401. Alternatively, the gate insulating layer 442 may be patterned to have the same shape as the gate electrode 444.

An interlayer insulating layer 450, which is formed of an insulating material, is formed on an entire surface of the substrate 401 including the gate electrode 444. The interlayer insulating layer 450 may be formed of an inorganic insulating material, e.g., silicon oxide or silicon nitride, or an organic insulating material, e.g., benzocyclobutene or photo-acryl.

The interlayer insulating layer 450 includes first and second semiconductor contact holes 452 and 454 exposing both sides of the semiconductor layer 440. The first and second semiconductor contact holes 452 and 454 are positioned at both sides of the gate electrode 444 to be spaced apart from the gate electrode 444. In FIG. 3, the first and second semiconductor contact holes 452 and 454 are formed through the gate insulating layer 442 as well as the interlayer insulating layer 450. Alternatively, when the gate insulating layer 442 has the same shape as the gate electrode 444, the first and second semiconductor contact holes 452 and 454 may be formed in the interlayer insulating layer 450 except the gate insulating layer 442.

The source electrode 456 and the drain electrode 458, which are formed of a conductive material, e.g., metal, are formed on the interlayer insulating layer 450. The source and drain electrodes 456 and 458 may be formed of the same material as the gate electrode 444. In addition, a data line (not shown) extending along a second direction, a power line (not shown) and a second capacitor electrode (not shown) may be formed on the interlayer insulating layer 450. The data line crosses the gate line to define a pixel region, and the power line is spaced apart from and parallel to the data line. The second capacitor electrode is connected to the drain electrode 458 and overlaps the first capacitor electrode to form a storage capacitor with the interlayer insulating layer 450.

The source electrode 456 and the drain electrode 458 are spaced apart from each other with respect to the gate electrode 444 and respectively contact both sides of the semiconductor layer 440 through the first and second semiconductor contact holes 452 and 454.

In the driving TFT Td, the gate electrode 444, the source electrode 456 and the drain electrode 458 are positioned over the semiconductor layer 440. Namely, the driving TFT Td has a coplanar structure.

Alternatively, in the driving TFT Td, the gate electrode may be positioned under the semiconductor layer, and the source and drain electrodes may be positioned over the semiconductor layer such that the driving TFT Td may have an inverted staggered structure. In this instance, the semiconductor layer may include amorphous silicon.

A switching TFT (not shown) is formed on the substrate 401. The switching TFT may have substantially the same structure as the driving TFT Td. The gate electrode 444 is connected to a drain electrode of the switching TFT, and the source electrode 456 is connected to the power line. A gate electrode and a source electrode of the switching TFT are connected to the gate line and the data line, respectively.

A planarization layer 460, which provides a flat top surface and includes a drain contact hole 462 exposing the drain electrode 458 of the driving TFT Td, is formed to cover the driving TFT Td. The drain contact hole 462 may be spaced apart from the second semiconductor contact hole 454 in a plane.

The organic light emitting diode E is disposed on the planarization layer 460 and includes a first electrode 410, an organic emitting layer 430 and a second electrode 420. The first electrode 410 is connected to the drain electrode 458 of the driving TFT Td, and the organic emitting layer 430 and the second electrode 420 are sequentially stacked on the first electrode 410. A bank 472 as a pixel definition layer is formed to cover an edge of the first electrode 410.

As mentioned above, the first electrode 410 as an anode includes a high work function conductive material, and the second electrode 420 as a cathode includes a low work function conductive material.

As explained above, the organic layer 430 includes at least one of the first and second organic compounds of the present invention with or without a dopant.

An encapsulation film 480 for preventing the penetration of moisture and/or oxygen into the organic light emitting diode E is formed on or over the second electrode 420. Although not shown, the encapsulation film 480 may has a triple-layered structure of a first inorganic layer, an organic layer and a second inorganic layer, which are sequentially stacked on or over the second electrode 420, but it is not limited thereto.

As mentioned above, since the organic compound of the invention includes the carbazole moiety, on which a side ring is fused, the thermal stability of the organic compound is increased. In the first organic compound, two fused carbazole moieties are connected to each other such that the first organic compound has excellent hole transporting property. On the other hand, in the second organic compound, a hetero aromatic ring, which includes a nitrogen atom, is directly or indirectly connected to a fused carbazole moiety such that the organic compound has excellent electron transporting property as well as excellent hole transporting property. Accordingly, when the organic compound of the present invention is included in at least one organic layer of the organic light emitting diode E, the charge is efficiently transferred such that the driving voltage of the OLED device 400 is reduced. For example, when the first and second organic compounds are included in the EML (160 in FIG. 1 or 260 in FIG. 2), the balance of the charges is improved such that the emission is generated in an entire region of the EML (160 in FIG. 1 or 260 in FIG. 2). As a result, the emission efficiency and the lifetime of the OLED device 400 are improved.

Synthesis

1. Synthesis of the Compound PPH1

(1) 2,4-dibromo-1-nitrobenzene

[Reaction Formula 1a]

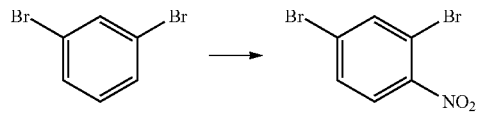 [SMILES: Brc1cccc(Br)c1 ; O=[N+]([O-])c1ccc(Br)cc1Br]

Sulfuric acid (744 mL) and nitric acid (144 mL) were mixed. In the temperature of 0° C., 1,3-dibromobenzene (300 g, 1,270 mmol) were slowly dropped and stirred for 30 minutes. After completion of the reaction, ice water was slowly dropped into the mixture, and the solid was filtered and extracted using ethylacetate in several times. The organic solvent was removed, and the silica-gel column process was performed to obtain 2,4-dibromo-1-nitrobenzene (261 g, yield: 73%).

(2) 4-(5-bromo-2-nitrophenyl)dibenzo[b,d]furan

[Reaction Formula 1b]

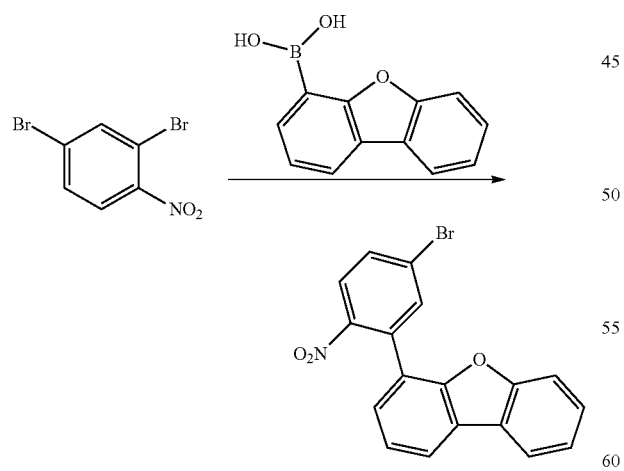

2,4-dibromo-1-nitrobenzene (100 g, 356 mmol), dibenzofuran boronic acid 75 g (356 mmol), Pd(pph3)4 12.3 g (10.6 mmol) and K2CO3 98.4 g (712 mmol) were dissolved in a mixture of ethyl alcohol (336 mL), distilled water (336 mL) and toluene (1680 mL) and stirred for 2 hours. After completion of the reaction, the mixture was distilled under the reduced pressure. The silica-gel column process was performed to obtain 4-(5-bromo-2-nitrophenyl)dibenzo[b,d]furan (60 g, yield: 45%).

(3) 2-bromo-5H-benzofuro[3,2-c]carbazole

[Reaction Formula 1c]

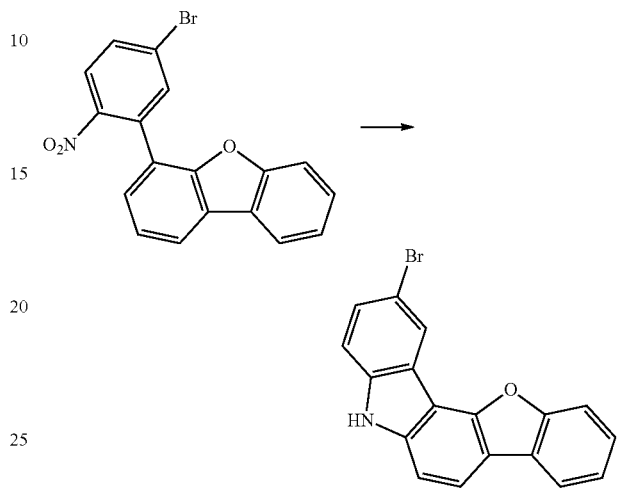

4-(5-bromo-2-nitrophenyl)dibenzo[b,d]furan (140 g, 380 mmol) and triphenylphosphine (299 g, 1,149 mmol) were dissolved in 1,2-dichlorobenzene (980 mL) and stirred for 12 hours. The solvent was removed by concentration under the reduced pressure, and the silica-gel column process was performed to obtain 2-bromo-5H-benzofuro[3,2-c]carbazole (25 g, yield: 20%).

(4) 2-(9-phenyl-9H-carbazol-3-yl)-5H-benzofuro[3,2-c]carbazole

[Reaction Formula 1d]

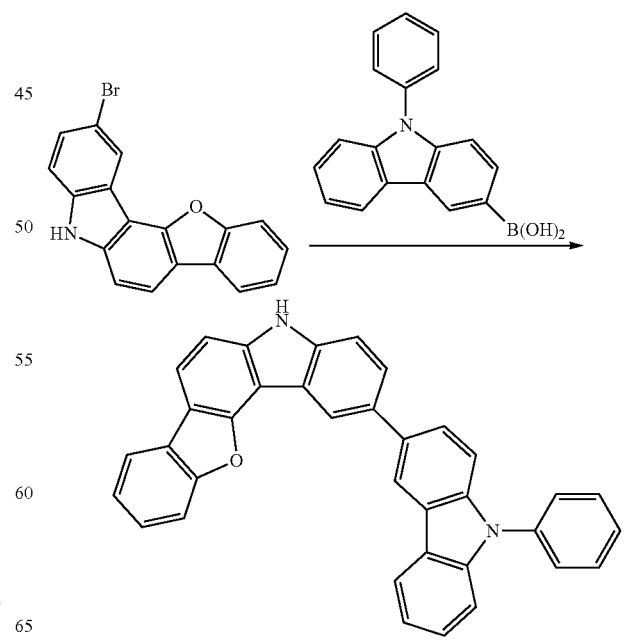

2-bromo-5H-benzofuro[3,2-c]carbazole (6.5 g, 19 mmol), 9-phenyl-9H-carbazol-3-yl-boronic acid (6.6 g, 23 mmol), Pd(pph3)Cl4 (0.9 g, 0.8 mmol) and K2CO3 (7.1 g, 51 mmol) were dissolved in a mixture of ethyl alcohol (33 mL), distilled water (26 mL) and toluene (65 mL). The mixture was refluxed and stirred for 12 hours. The resultant was cooled into the room temperature, and the extracted solid was filtered. The solid was washed using methyl alcohol in several times to obtain 2-(9-phenyl-9H-carbazol-3-yl)-5H-benzofuro[3,2-c]carbazole (7 g, yield: 74%).

(5) 2,2'-dibromobiphenyl

[Reaction Formula 1e]

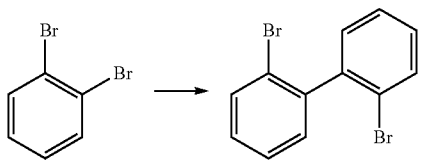 [SMILES: Brc1ccccc1Br ; Brc1ccccc1-c1ccccc1Br]

1,2-Dibromobenzene (51 mL, 424 mmol) was dissolved in THF and cooled into the temperature of −78° C. n-BuLi (90 mL, 2.5M, 225 mmol) was slowly dropped into the solution for 1 hour and stirred under the room temperature for 12 hours. The mixture was quenched by water and extracted by ether. After the solvent was removed, the resultant was re-precipitated using hexane such that 2,2'-dibromobiphenyl was obtained. (29.4 g, yield: 22%)

(6) 9-(2'-bromobiphenyl-2-yl)-9H-fluoren-9-ol

[Reaction Formula 1f]

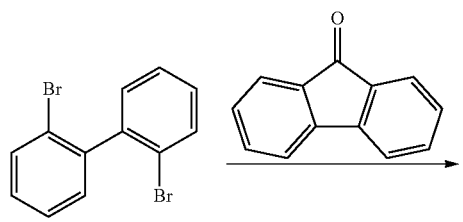

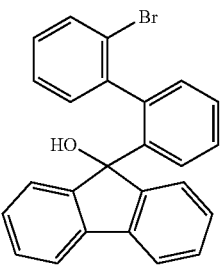

2,2'-dibromobiphenyl (29.4 g, 94.2 mmol) was dissolved in THF and cooled into the temperature of −78° C. n-BuLi (37 mL, 2.5M, 94 mmol) was slowly dropped into the solution, and fluorene (20.4 g, 113 mmol), which is dissolved in THF, was slowly dropped. The solution was slowly heated up to the room temperature and stirred for 12 hours. The mixture was quenched by distilled water and extracted by ether such that the yellow solid (9-(2'-bromobiphenyl-2-yl)-9H-fluoren-9-ol) was obtained. (36 g)

(7) 4-bromo-9,9'-spirobi[fluorene]

[Reaction Formula 1g]

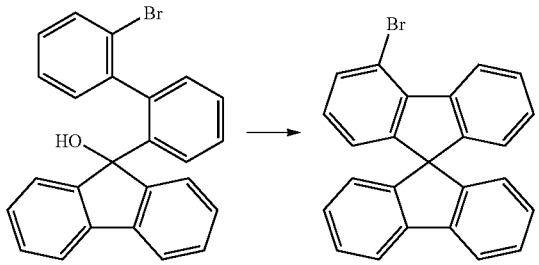 [SMILES: OC1(c2ccccc2-c2ccccc2Br)c2ccccc2-c2ccccc21 ; Brc1cccc2c1-c1ccccc1C21c2ccccc2-c2ccccc21]

9-(2'-bromobiphenyl-2-yl)-9H-fluoren-9-ol (36 g, 94 mmol) was dissolved in a mixture of acetic acid (360 mL) and hydrochloric acid (36 mL, 36%). The mixture was refluxed and stirred for 12 hours. After removing the solvent, the silica-gel column was performed such that 4-bromo-9,9'-spirobi[fluorene] was obtained. (32 g, yield: 86%)

(8) the compound PPH1

[Reaction Formula 1h]

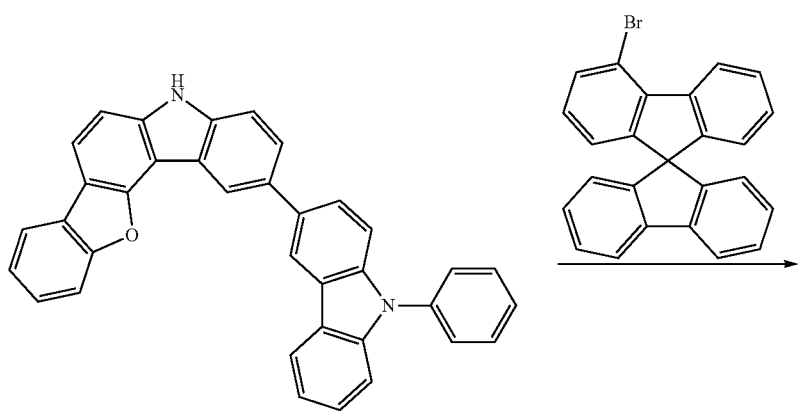

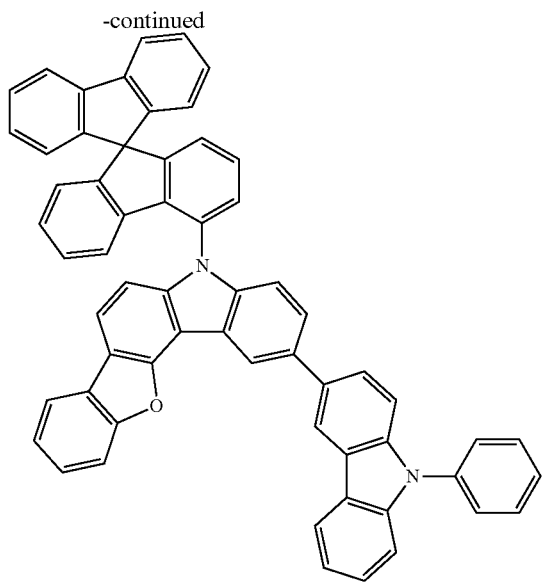

2-(9-phenyl-9H-carbazol-3-yl)-5H-benzofuro[3,2-c]carbazole (7 g, 14 mmol), 4-bromo-9,9'-spirobi[fluorene] (6.7 g, 17 mmol), Pd2(dba)3 (0.64 g, 0.7 mmol), tert-tributylphosphine (0.17 g, 0.84 mmol) and tert-sodiumbutoxide (3.56 g, 37 mmol) were dissolved in toluene (280 mL). The mixture was refluxed and stirred for 48 hours, and the resultant was extracted 3 times by methylenechloride. The resultant was concentrated under the reduced pressure, washed and columned in the silica-gel such that the compound PPH1 was obtained. (2.5 g, yield: 22%)

2. Synthesis of the Compound PPH3

(1) 9-(biphenyl-3-yl)-9H-carbazole

[Reaction Formula 2a]

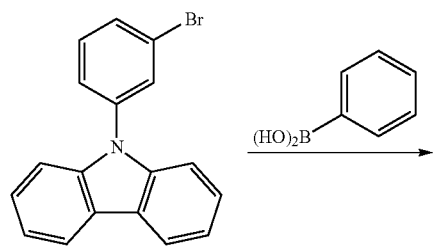

3-bromo-phenylcarbazole (20 g, 62 mmol), phenyl boronic acid (9.08 g, 74 mmol), Pd(pph3)Cl4 (0.7 g, 0.621 mmol) and K2CO3 (17.2 g, 124 mmol) were dissolved in a mixture of ethyl alcohol (200 mL) and toluene (800 mL). The mixture was refluxed and stirred for 12 hours. The resultant was re-precipitated to obtain 9-(biphenyl-3-yl)-9H-carbazole (16.2 g, yield: 82%).

(2) 9-(biphenyl-3-yl)-3-bromo-9H-carbazole

[Reaction Formula 2b]

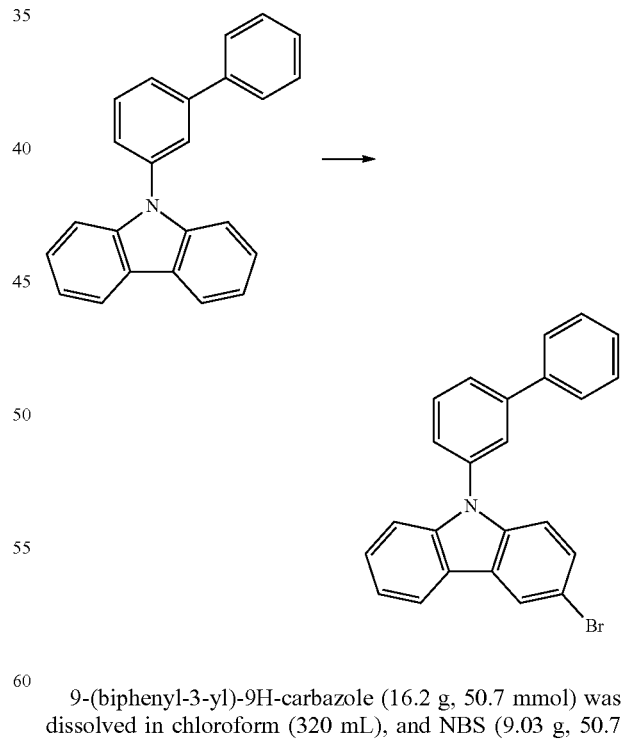

9-(biphenyl-3-yl)-9H-carbazole (16.2 g, 50.7 mmol) was dissolved in chloroform (320 mL), and NBS (9.03 g, 50.7 mmol) was slowly dropped. The mixture was refluxed and stirred for 5 hours. After completion of the reaction, distilled water was added and extracted. The resultant was columned in the silica-gel such that crude-state 9-(biphenyl-3-yl)-3-bromo-9H-carbazole (17.2 g) was obtained.

(3) 9-(biphenyl-3-yl)-9H-carbazol-3-ylboronic acid

[Reaction Formula 2c]

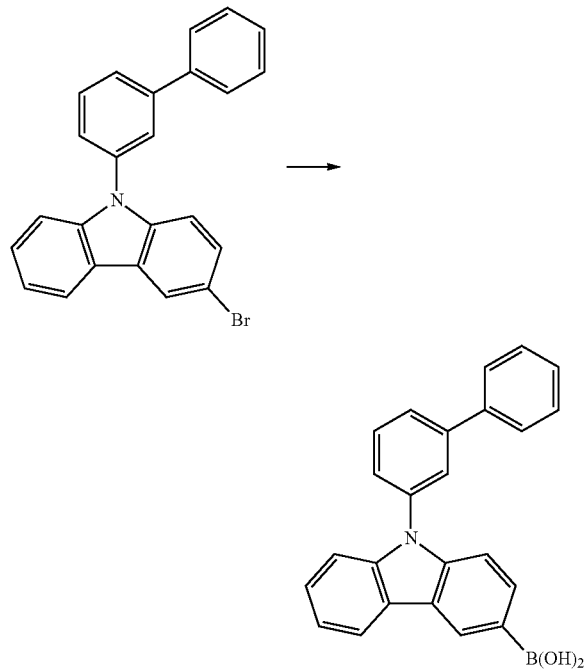

9-(biphenyl-3-yl)-3-bromo-9H-carbazole (17.2 g, 43.1 mmol) was dissolved in THF (172 mL) and cooled into the temperature of −78° C. n-BuLi (20.7 mL, 2.5M, 51.7 mmol) was slowly dropped into the solution and stirred for 1 hour. Triethylborate (8.8 mL, 51.7 mmol) was added, and the solution was stirred under the room temperature for 12 hours. After completion of the reaction, the resultant was re-precipitated using TFH and hexane such that 9-(biphenyl-3-yl)-9H-carbazol-3-ylboronic acid (12 g, yield: 76%) was obtained.

(4) 2-(9-(biphenyl-3-yl)-9H-carbazol-3-yl)-5H-benzofuro[3,2-c]carbazole

[Reaction Formula 2d]

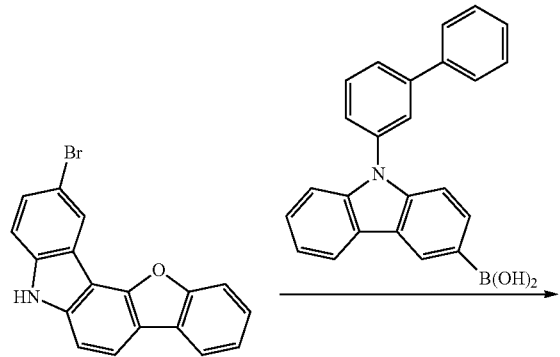

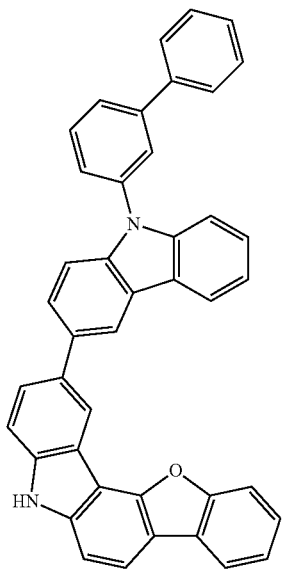

2-bromo-5H-benzofuro[3,2-c]carbazole (5.4 g, 16.06 mmol), 9-(biphenyl-3-yl)-9H-carbazol-3-ylboronic acid (7 g, 19.27 mmol), Pd(pph3)4 (0.9 g, 0.8 mmol) and K2CO3 (6.66 g, 48 mmol) were dissolved in a mixture of ethyl alcohol (30 mL), distilled water (30 mL) and toluene (50 mL). The mixture was refluxed and stirred for 12 hours. After extracting by ethylacetate, the resultant was columned in the silica-gel such that 2-(9-(biphenyl-3-yl)-9H-carbazol-3-yl)-5H-benzofuro[3,2-c]carbazole (4.5 g, yield: 49%) was obtained.

(5) The Compound PPH3

[Reaction Formula 2e]

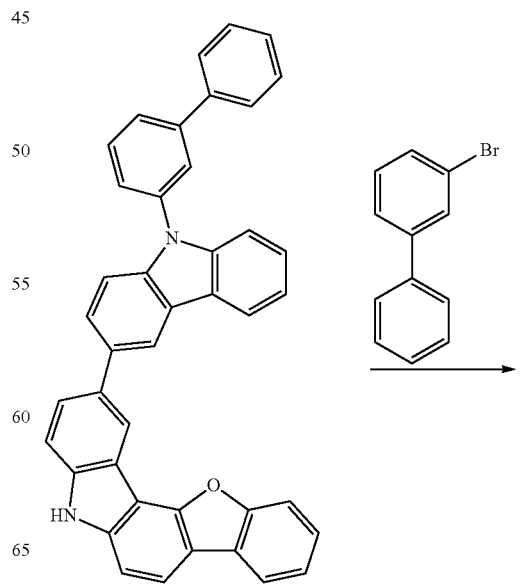

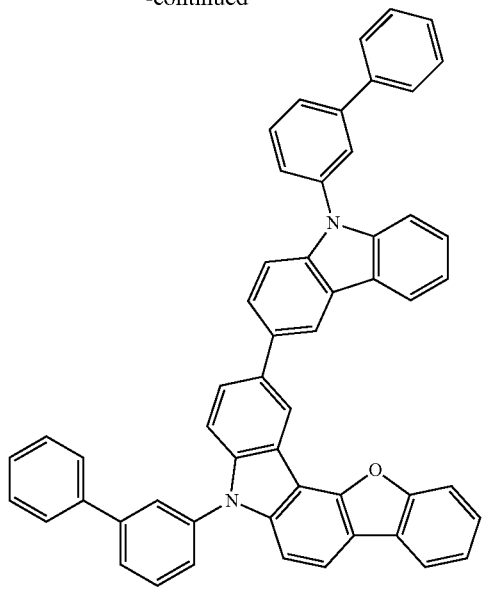

2-(9-(biphenyl-3-yl)-9H-carbazol-3-yl)-5H-benzofuro[3,2-c]carbazole (4.5 g, 7.83 mmol), 3-bromobiphenyl (5.48 g, 23.5 mmol), Pd2(dba)3 (0.28 g), tert-butylphosphine (0.95 mg, 0.470 mmol) and tert-sodiumbutoxide (1.66 g, 17.2 mmol) were dissolved in toluene (100 mL). The mixture was refluxed and stirred for 12 hours. The resultant was columned in the silica-gel such that the compound PPH3 was obtained. (2 g, yield: 56%)

3. Synthesis of the Compound PPH5

(1) 3-(biphenyl-3-yl)-3H-benzofuro[2,3-b]carbazole

[Reaction Formula 3a]

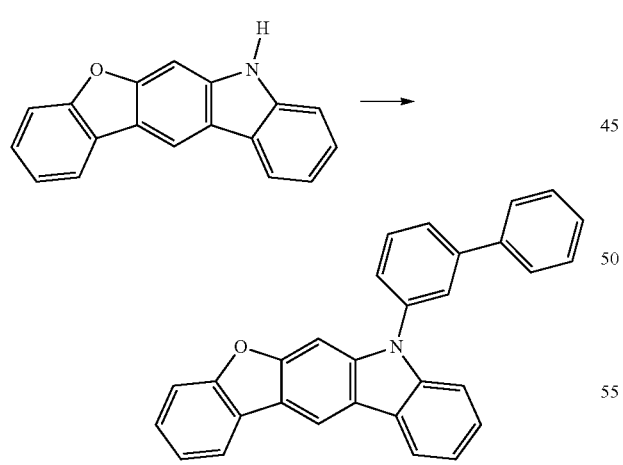

Dibenzofurocarbazole (77 g, 299 mmol), 3-meta-bromo-biphenyl (60 g, 359 mmol), sodium-tert-butoxide (86 g, 897 mmol), Pd2(dba)3 (14 g, 359 mmol) and tri-tert-butylphosphine (15 mL, 30 mmol) were suspended in xylene (1000 mL). The solution was refluxed and stirred for 12 hours. The resultant was extracted by dichloromethane and distilled water, and the organic layer was filled in the silica-gel. After removing the organic solvent, the resultant was columned in the silica-gel such that 3-(biphenyl-3-yl)-3H-benzofuro[2,3-b]carbazole (80 g, yield: 65%) was obtained.

(2) 3-(biphenyl-3-yl)-6-bromo-3H-benzofuro[2,3-b]carbazole

[Reaction Formula 3b]

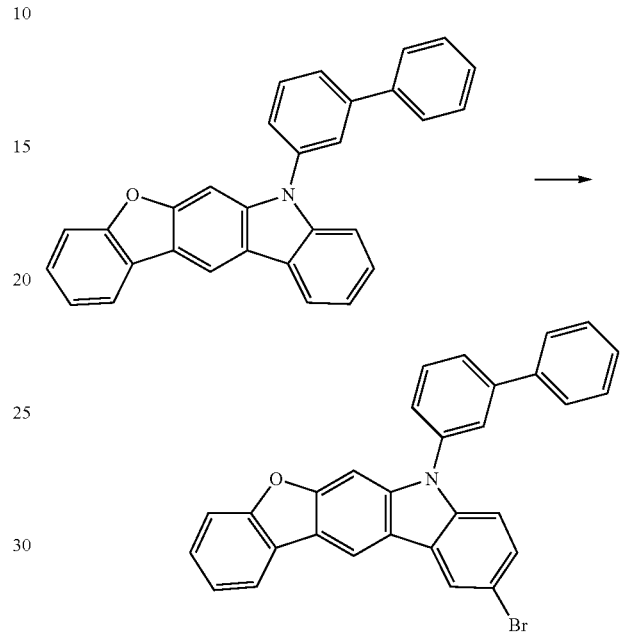

3-(biphenyl-3-yl)-3H-benzofuro[2,3-b]carbazole (47 g, 114 mmol) and NBS (22 g, 126 mmol) were suspended in dimethylformamide (600 mL) and stirred under the room temperature for 12 hours. After distilled water was added, the mixture was stirred under the room temperature for 6 hours. After filtering under the reduced pressure, the solid was added in methyl alcohol and stirred under the room temperature. The resultant was filtered under the reduced pressure such that 3-(biphenyl-3-yl)-6-bromo-3H-benzofuro[2,3-b]carbazole (50 g, yield: 71%) was obtained.

(3) 3-(biphenyl-3-yl)-6-(4,4,5,5-tetramethyl-1,3,2-dioxaborolan-2-yl)-3H-benzofuro[2,3-b]carbazole

[Reaction Formula 3c]

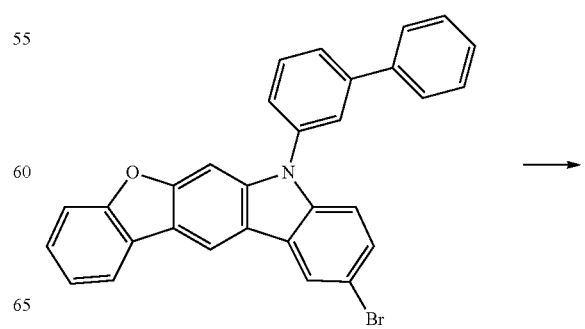

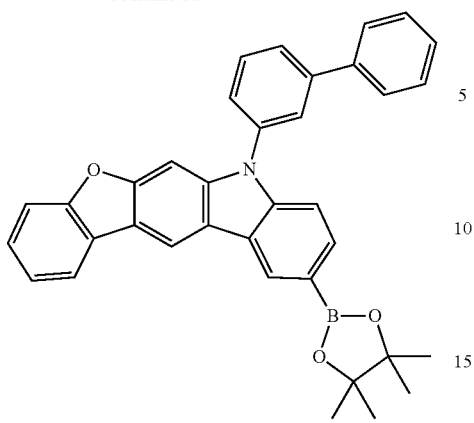

3-(biphenyl-3-yl)-6-bromo-3H-benzofuro[2,3-b]carbazole (49 g, 100 mmol), bis(pinacolato)diboron (38 g, 151 mmol), Pd(dppf)Cl2 (4 g, 5 mmol) and potassium acetate (20 g, 201 mmol) were suspended in 1,4-dioxane (600 mL) and refluxed/stirred for 12 hours. The mixture was extracted by dichloromethane and distilled water, and the organic layer is filled in the silica-gel. After removing the organic solvent, the solid was re-crystallized such that 3-(biphenyl-3-yl)-6-(4,4,5,5-tetramethyl-1,3,2-dioxaborolan-2-yl)-3H-benzofuro[2,3-b]carbazole (40 g, yield: 75%) was obtained.

(4) the Compound PPH5

[Reaction Formula 3d]

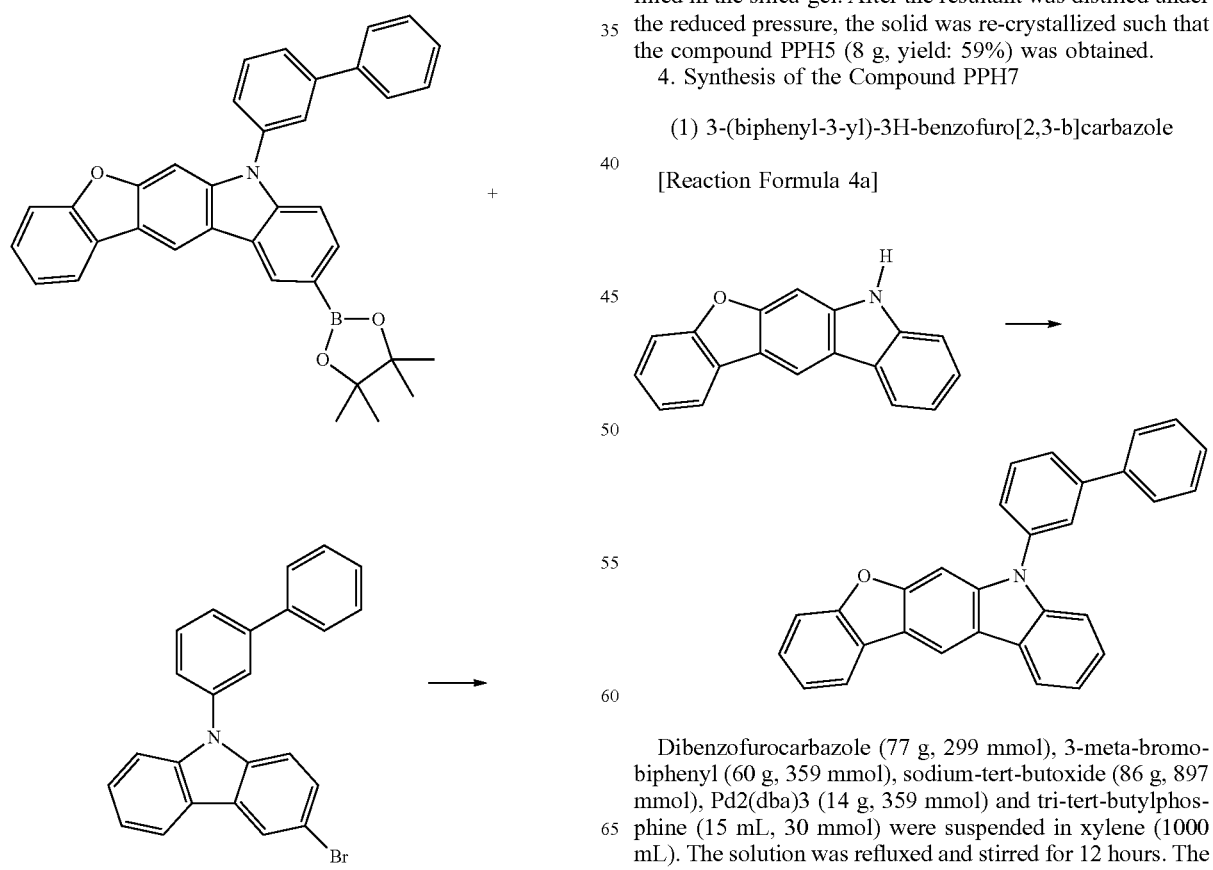

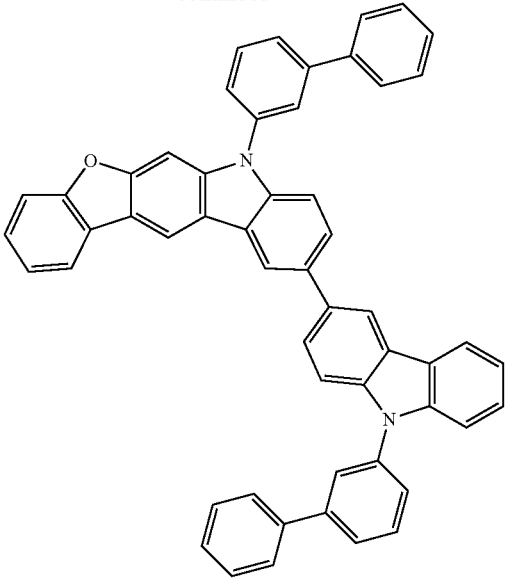

3-(biphenyl-3-yl)-6-(4,4,5,5-tetramethyl-1,3,2-dioxaborolan-2-yl)-3H-benzofuro [2,3-b]carbazole (10 g, 19 mmol), 9-meta-biphenyl-3-bromocarbazole (7 g, 19 mmol), Pd(PPh3)4 (0.2 g, 0.2 mmol) and potassium carbonate (5 g, 37 mmol) were suspended in a mixture of toluene (150 mL), ethylalcohol (50 mL) and distilled water (50 mL) and refluxed/stirred for 12 hours. The mixture was extracted by dichloromethane and distilled water, and the organic layer is filled in the silica-gel. After the resultant was distilled under the reduced pressure, the solid was re-crystallized such that the compound PPH5 (8 g, yield: 59%) was obtained.

4. Synthesis of the Compound PPH7

(1) 3-(biphenyl-3-yl)-3H-benzofuro[2,3-b]carbazole

[Reaction Formula 4a]

Dibenzofurocarbazole (77 g, 299 mmol), 3-meta-bromobiphenyl (60 g, 359 mmol), sodium-tert-butoxide (86 g, 897 mmol), Pd2(dba)3 (14 g, 359 mmol) and tri-tert-butylphosphine (15 mL, 30 mmol) were suspended in xylene (1000 mL). The solution was refluxed and stirred for 12 hours. The resultant was extracted by dichloromethane and distilled water, and the organic layer was filled in the silica-gel. After removing the organic solvent, the resultant was columned in the silica-gel such that 3-(biphenyl-3-yl)-3H-benzofuro[2,3-b]carbazole (80 g, yield: 65%) was obtained.

(2) 3-(biphenyl-3-yl)-6-bromo-3H-benzofuro[2,3-b]carbazole

[Reaction Formula 4b]

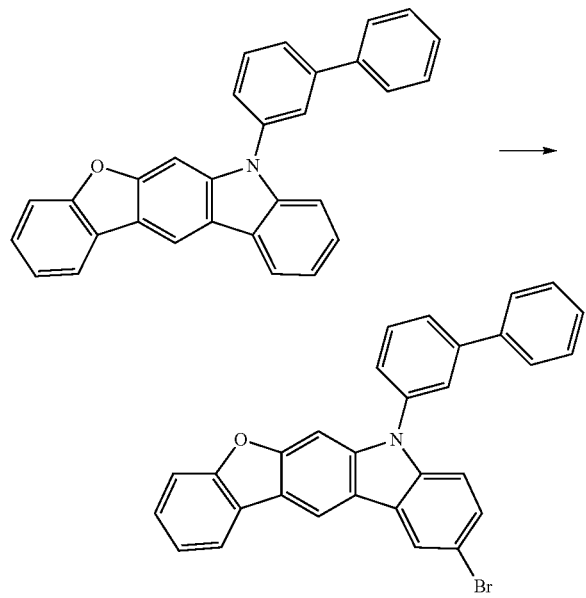

3-(biphenyl-3-yl)-3H-benzofuro[2,3-b]carbazole (47 g, 114 mmol) and NBS (22 g, 126 mmol) were suspended in dimethylformamide (600 mL) and stirred under the room temperature for 12 hours. After distilled water was added, the mixture was stirred under the room temperature for 6 hours. After filtering under the reduced pressure, the solid was added in methyl alcohol and stirred under the room temperature. The resultant was filtered under the reduced pressure such that 3-(biphenyl-3-yl)-6-bromo-3H-benzofuro[2,3-b]carbazole (50 g, yield: 71%) was obtained.

(3) 3-(biphenyl-3-yl)-6-(4,4,5,5-tetramethyl-1,3,2-dioxaborolan-2-yl)-3H-benzofuro[2,3-b]carbazole

[Reaction Formula 4c]

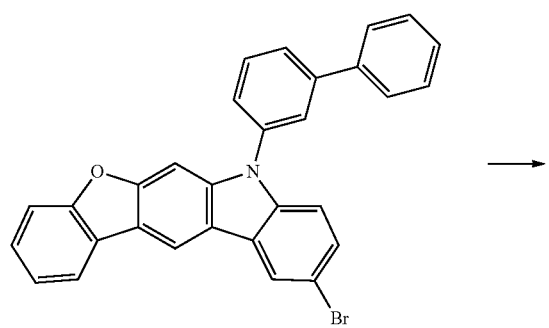

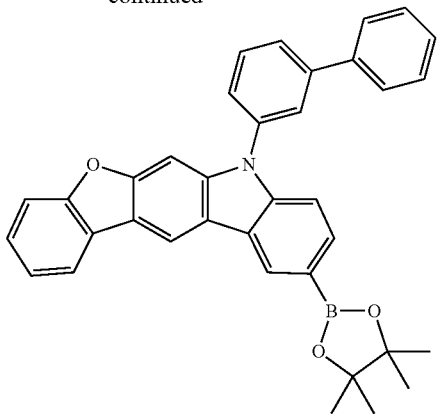

3-(biphenyl-3-yl)-6-bromo-3H-benzofuro[2,3-b]carbazole (49 g, 100 mmol), bis(pinacolato)diboron (38 g, 151 mmol), Pd(dppf)Cl2 (4 g, 5 mmol) and potassium acetate (20 g, 201 mmol) were suspended in 1,4-dioxane (600 mL) and refluxed/stirred for 12 hours. The mixture was extracted by dichloromethane and distilled water, and the organic layer is filled in the silica-gel. After removing the organic solvent, the solid was re-crystallized such that 3-(biphenyl-3-yl)-6-(4,4,5,5-tetramethyl-1,3,2-dioxaborolan-2-yl)-3H-benzofuro[2,3-b]carbazole (40 g, yield: 75%) was obtained.

(4) the Compound PPH7

[Reaction Formula 4d]

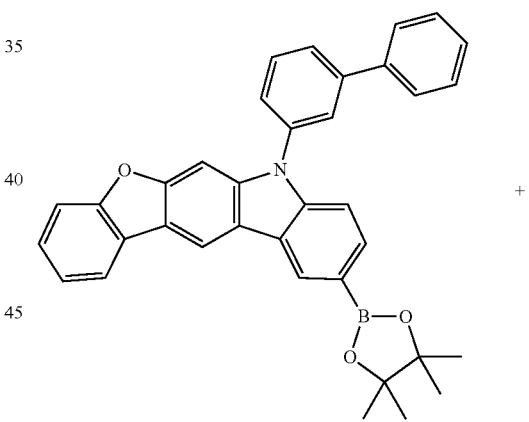

+

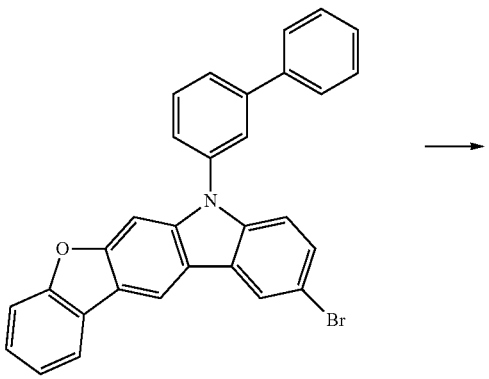

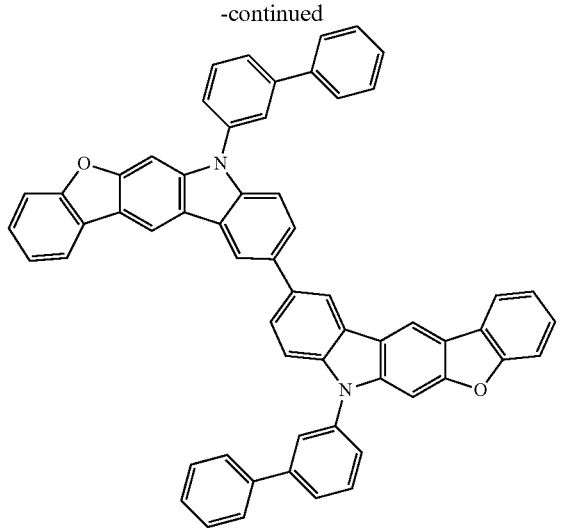

3-(biphenyl-3-yl)-6-(4,4,5,5-tetramethyl-1,3,2-dioxaborolan-2-yl)-3H-benzofuro [2,3-b]carbazole (10 g, 19 mmol), 3-(biphenyl-3-yl)-6-bromo-3H-benzofuro[2,3-b]carbazole (9 g, 19 mmol), Pd(PPh3)4 (0.2 g, 0.2 mmol) and potassium carbonate (5 g, 37 mmol) were suspended in a mixture of toluene (150 mL), ethylalcohol (50 mL) and distilled water (50 mL) and refluxed/stirred for 12 hours. The mixture was extracted by dichloromethane and distilled water, and the organic layer is filled in the silica-gel. After the resultant was distilled under the reduced pressure, the solid was re-crystallized such that the compound PPH7 (8 g, yield: 59%) was obtained.

5. Synthesis of the Compound PPH9

(1) Benzothieno Carbazole Derivative

[Reaction Formula 5a]

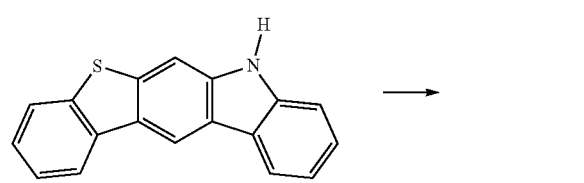

Benzothieno carbazole (77 g, 302 mmol), 3-meta-bromobiphenyl (60 g, 359 mmol), sodium-tert-butoxide (86 g, 897 mmol), Pd2(dba)3 (14 g, 359 mmol) and tri-tert-butylphosphine (15 mL, 30 mmol) were suspended in xylene (1000 mL). The solution was refluxed and stirred for 12 hours. The resultant was extracted by dichloromethane and distilled water, and the organic layer was filled in the silica-gel. After removing the organic solvent, the resultant was columned in the silica-gel such that benzothieno carbazole derivative (80 g, yield: 65%) was obtained.

(2) Bromo-Benzothieno Carbazole Derivative

[Reaction Formula 5b]

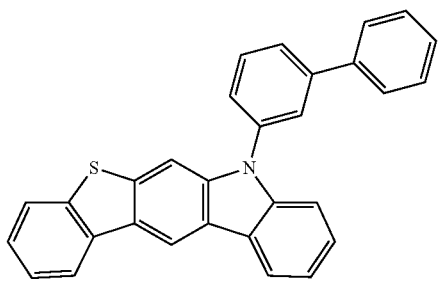 

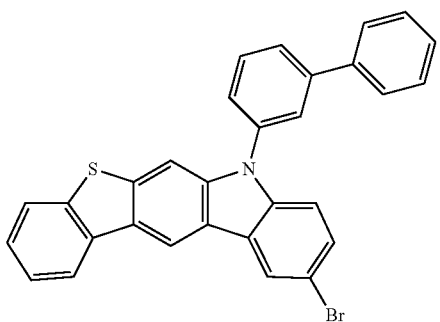

Benzothieno carbazole derivative (47 g, 120 mmol) and NBS (22 g, 126 mmol) were suspended in dimethylformamide (600 mL) and stirred under the room temperature for 12 hours. After distilled water was added, the mixture was stirred under the room temperature for 6 hours. After filtering under the reduced pressure, the solid was added in methyl alcohol and stirred under the room temperature. The resultant was filtered under the reduced pressure such that bromo-benzothieno carbazole derivative (50 g, yield: 71%) was obtained.

(3) Pinacol-Benzothieno Carbazole Derivative

[Reaction Formula 5c]

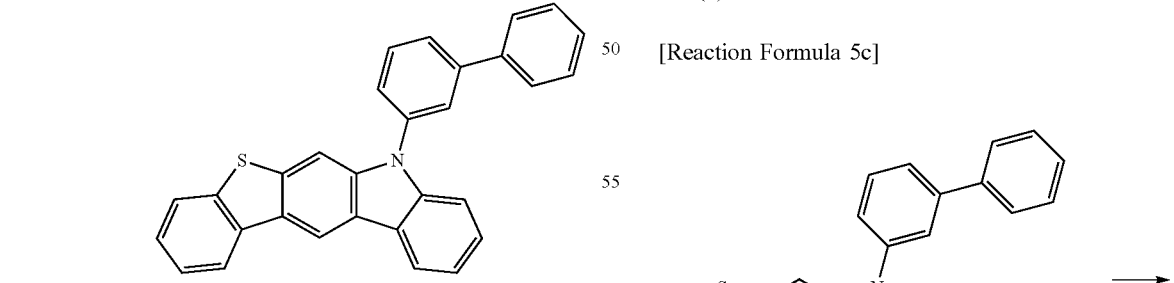

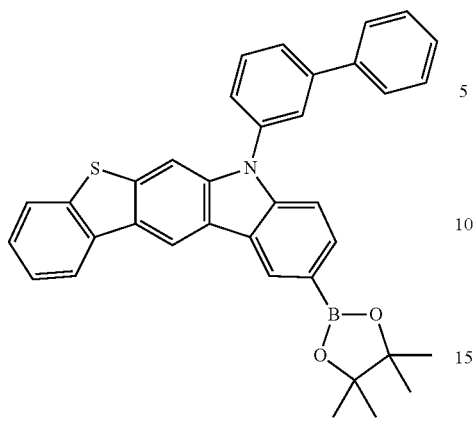

Bromo-benzothieno carbazole derivative (49 g, 105 mmol), bis(pinacolato)diboron (38 g, 151 mmol), Pd(dppf)Cl2 (4 g, 5 mmol) and potassium acetate (20 g, 201 mmol) were suspended in 1,4-dioxane (600 mL) and refluxed/stirred for 12 hours. The mixture was extracted by dichloromethane and distilled water, and the organic layer is filled in the silica-gel. After removing the organic solvent, the solid was re-crystallized such that pinacol-benzothieno carbazole derivative (40 g, yield: 75%) was obtained.

(4) The Compound PPH9

[Reaction Formula 5d]

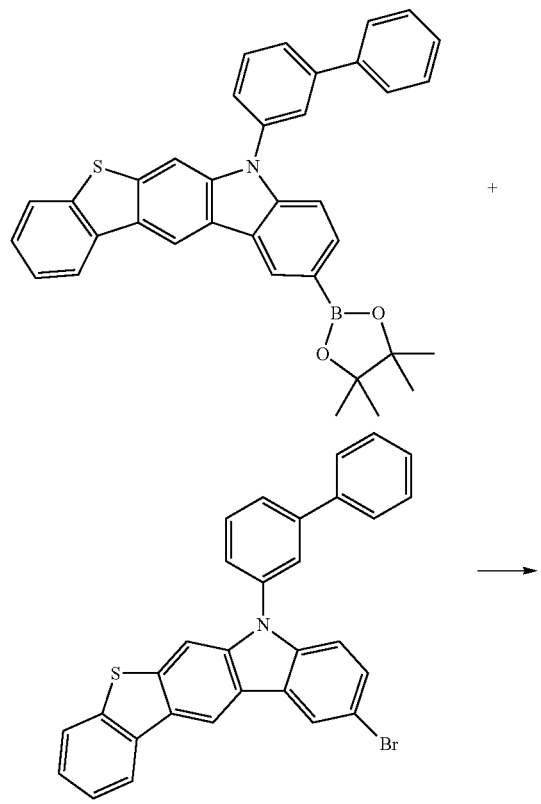

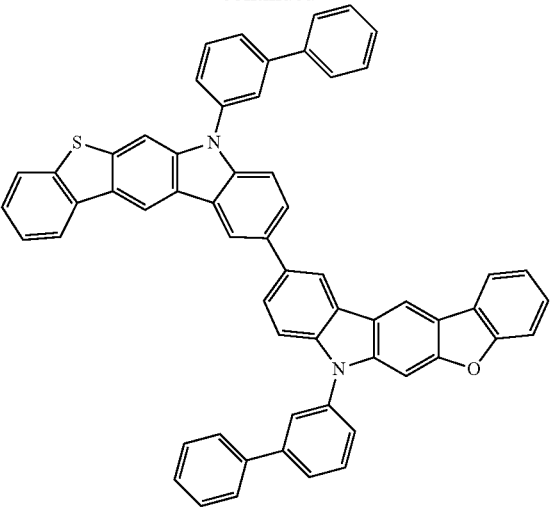

Pinacol-benzothieno carbazole derivative (10 g, 19 mmol), bromo-benzothieno carbazole derivative (9 g, 19 mmol), Pd(PPh3)4 (0.2 g, 0.2 mmol) and potassium carbonate (5 g, 37 mmol) were suspended in a mixture of toluene (150 mL), ethylalcohol (50 mL) and distilled water (50 mL) and refluxed/stirred for 12 hours. The mixture was extracted by dichloromethane and distilled water, and the organic layer is filled in the silica-gel. After the resultant was distilled under the reduced pressure, the solid was re-crystallized such that the compound PPH9 (7 g, yield: 49%) was obtained.

6. Synthesis of the compound PPH11

(1) 6-bromo-1,1-dimethyl-3-phenyl-1,3-dihydroindeno[2,1-b]carbazole

[Reaction Formula 6a]

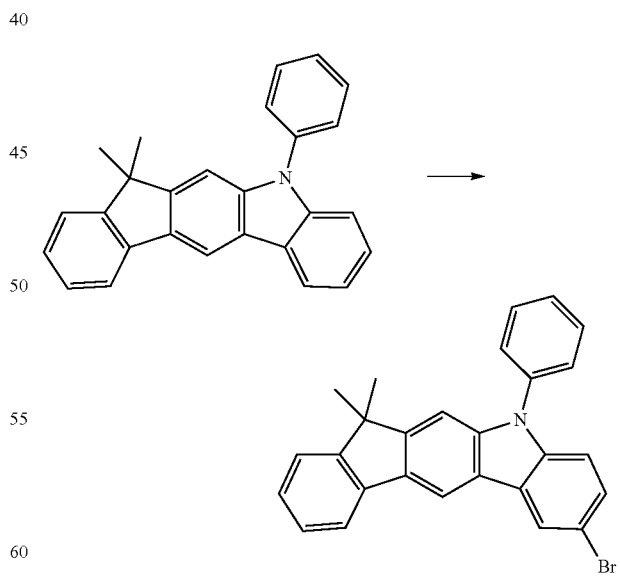

5-phenyl-indenocarbazole (43 g, 120 mmol), and NBS (22 g, 126 mmol) were suspended in dimethylformamide (600 mL) and stirred under the room temperature for 12 hours. After distilled water was added, the mixture was stirred under the room temperature for 6 hours. After filtering under the reduced pressure, the solid was added in methyl alcohol and stirred under the room temperature. The resultant was filtered under the reduced pressure such that 6-bromo-1,1-dimethyl-3-phenyl-1,3-dihydroindeno[2,1-b] carbazole (45 g, yield: 86%) was obtained.

(2) 1,1-dimethyl-3-phenyl-6-(4,4,5,5-tetramethyl-1,3,2-dioxaborolan-2-yl)-1,3-dihydroindeno[2,1-b] carbazole

[Reaction Formula 6b]

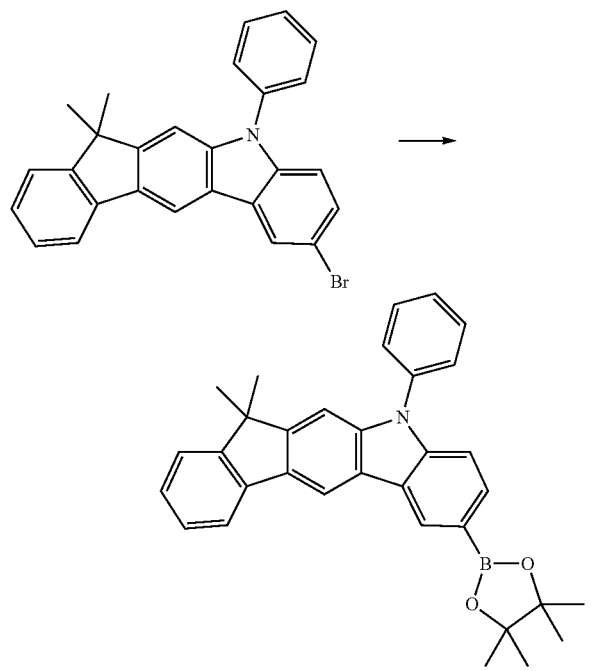

6-bromo-1,1-dimethyl-3-phenyl-1,3-dihydroindeno[2,1-b]carbazole (46 g, 105 mmol), bis(pinacolato)diboron (38 g, 156 mmol), Pd(dppf)Cl2 (4 g, 5 mmol) and potassium acetate (20 g, 201 mmol) were suspended in 1,4-dioxane (600 mL) and refluxed/stirred for 12 hours. The mixture was extracted by dichloromethane and distilled water, and the organic layer is filled in the silica-gel. After removing the organic solvent, the solid was re-crystallized such that 1,1-dimethyl-3-phenyl-6-(4,4,5,5-tetramethyl-1,3,2-dioxaborolan-2-yl)-1,3-dihydroindeno[2,1-b] carbazole (40 g, yield: 78%) was obtained.

(3) The Compound PPH11

[Reaction Formula 6c]

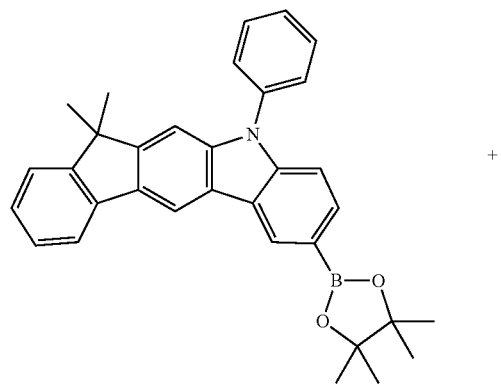

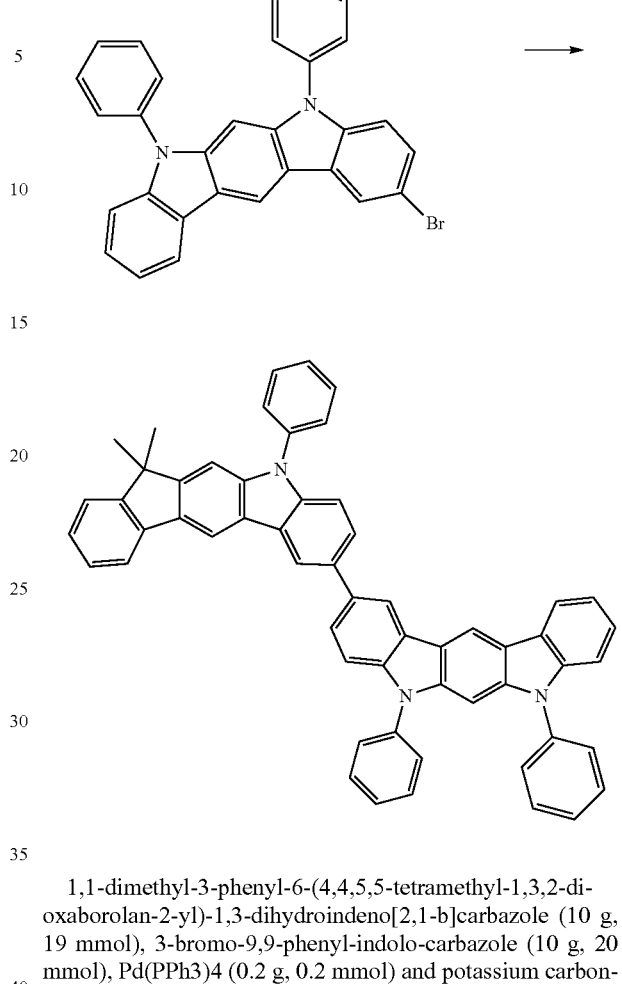

1,1-dimethyl-3-phenyl-6-(4,4,5,5-tetramethyl-1,3,2-dioxaborolan-2-yl)-1,3-dihydroindeno[2,1-b]carbazole (10 g, 19 mmol), 3-bromo-9,9-phenyl-indolo-carbazole (10 g, 20 mmol), Pd(PPh3)4 (0.2 g, 0.2 mmol) and potassium carbonate (5 g, 40 mmol) were suspended in a mixture of toluene (150 mL), ethylalcohol (50 mL) and distilled water (50 mL) and refluxed/stirred for 12 hours. The mixture was extracted by dichloromethane and distilled water, and the organic layer is filled in the silica-gel. After the resultant was distilled under the reduced pressure, the solid was re-crystallized such that the compound PPH11 (10 g, yield: 63%) was obtained.

7. Synthesis of the Compound PPH13

(1) 3'-phenyl-3'H-spiro[fluorene-9,1'-indeno[2,1-b] carbazole]

[Reaction Formula 7a]

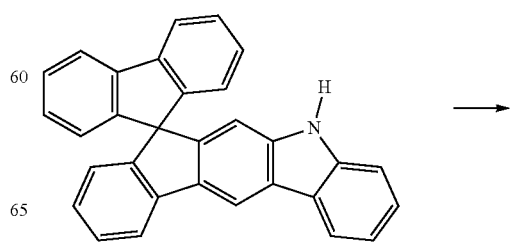

-continued

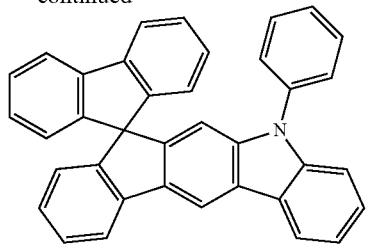

Spiro-bifluorene-indenocarbazole (121 g, 299 mmol), iodobenzene (73 g, 359 mmol), sodium-tert-butoxide (86 g, 897 mmol), Pd2(dba)3 (14 g, 359 mmol) and tri-tert-butylphosphine (15 mL, 30 mmol) were suspended in xylene (1000 mL). The solution was refluxed and stirred for 12 hours. The resultant was extracted by dichloromethane and distilled water, and the organic layer was filled in the silica-gel. After removing the organic solvent, the resultant was columned in the silica-gel such that 3'-phenyl-3'H-spiro[fluorene-9,1'-indeno[2,1-b]carbazole] (100 g, yield: 69%) was obtained.

(2) 6'-bromo-3'-phenyl-3'H-spiro[fluorene-9,1'-indeno[2,1-b]carbazole]

[Reaction Formula 7b]

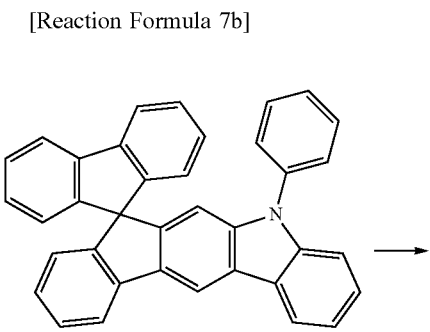

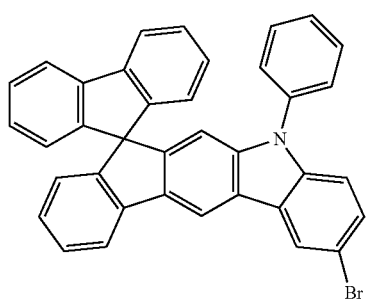

3'-phenyl-3'H-spiro[fluorene-9,1'-indeno[2,1-b]carbazole] (55 g, 114 mmol) and NBS (22 g, 126 mmol) were suspended in dimethylformamide (600 mL) and stirred under the room temperature for 12 hours. After distilled water was added, the mixture was stirred under the room temperature for 6 hours. After filtering under the reduced pressure, the solid was added in methyl alcohol and stirred under the room temperature. The resultant was filtered under the reduced pressure such that 6'-bromo-3'-phenyl-3'H-spiro[fluorene-9,1'-indeno[2,1-b]carbazole] (50 g, yield: 78%) was obtained.

(3) 3'-phenyl-6'-(4,4,5,5-tetramethyl-1,3,2-dioxaborolan-2-yl)-3'H-spiro[fluorene-9,1'-indeno[2,1-b]carbazole]

[Reaction Formula 7c]

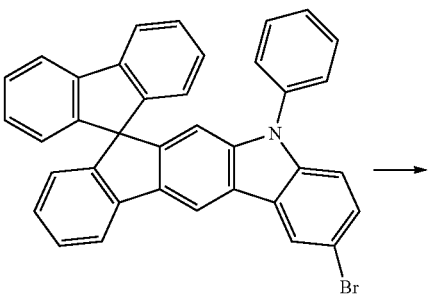

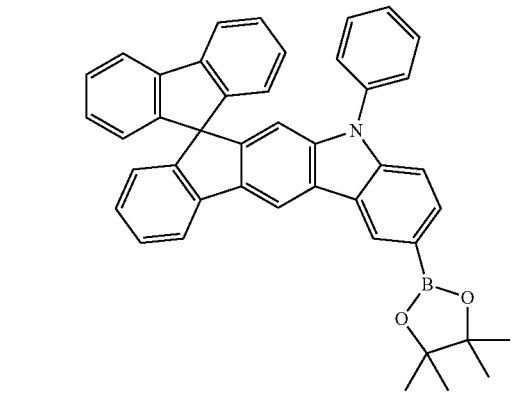

6'-bromo-3'-phenyl-3'H-spiro[fluorene-9,1'-indeno[2,1-b]carbazole] (56 g, 100 mmol), bis(pinacolato)diboron (38 g, 151 mmol), Pd(dppf)Cl2 (4 g, 5 mmol) and potassium acetate (20 g, 201 mmol) were suspended in 1,4-dioxane (600 mL) and refluxed/stirred for 12 hours. The mixture was extracted by dichloromethane and distilled water, and the organic layer is filled in the silica-gel. After removing the organic solvent, the solid was re-crystallized such that 3'-phenyl-6'-(4,4,5,5-tetramethyl-1,3,2-dioxaborolan-2-yl)-3'H-spiro[fluorene-9,1'-indeno[2,1-b] carbazole] (45 g, yield: 74%) was obtained.

(4) The Compound PPH13

[Reaction Formula 7d]

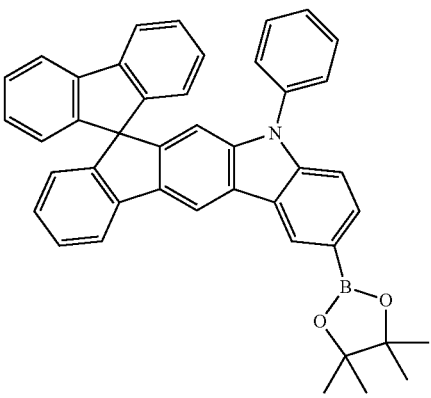

+

-continued

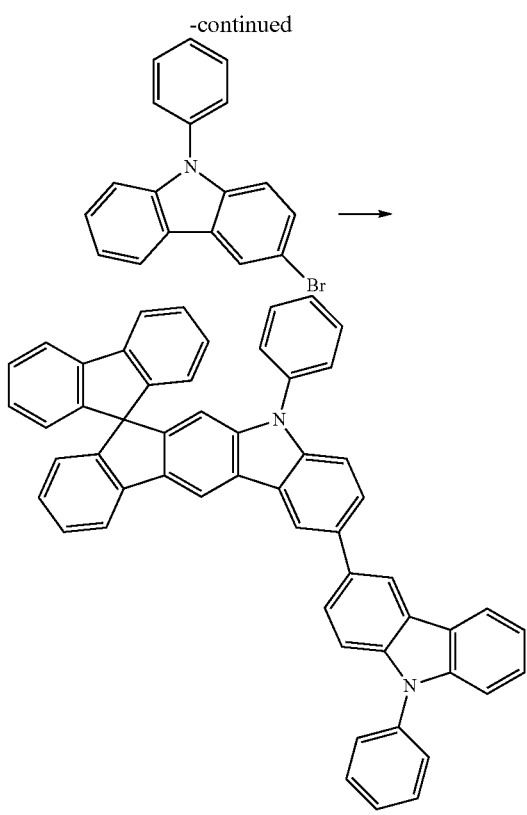

3'-phenyl-6'-(4,4,5,5-tetramethyl-1,3,2-dioxaborolan-2-yl)-3'H-spiro[fluorene-9, 1'-indeno[2,1-b]carbazole] (10 g, 19 mmol), 3-bromo-9-phenylcarbazole derivative (5 g, 16 mmol), Pd(PPh3)4 (0.2 g, 0.2 mmol) and potassium carbonate (5 g, 33 mmol) were suspended in a mixture of toluene (150 mL), ethylalcohol (50 mL) and distilled water (50 mL) and refluxed/stirred for 12 hours. The mixture was extracted by dichloromethane and distilled water, and the organic layer is filled in the silica-gel. After the resultant was distilled under the reduced pressure, the solid was re-crystallized such that the compound PPH13 (6 g, yield: 50%) was obtained.

8. Synthesis of the Compound PPH15
[Reaction Formula 8]

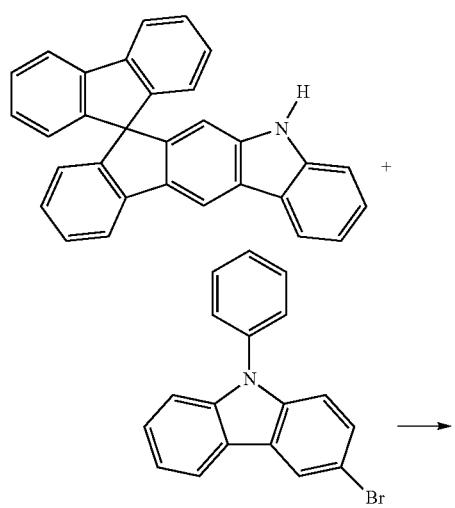

-continued

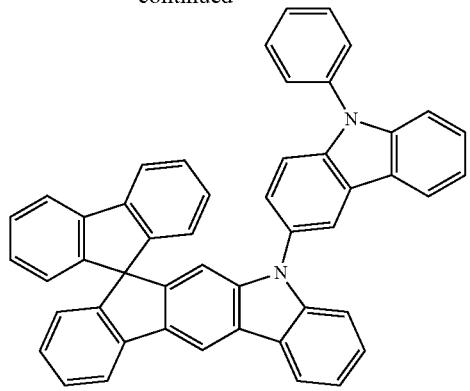

Spiro-bifluorene-indenocarbazole (12 g, 30 mmol), 3-bromo-9-phenylcarbazole (10 g, 30 mmol), sodium-tert-butoxide (6 g, 59 mmol), Pd2(dba)3 (1 g, 1.5 mmol) and tri-tert-butylphosphine (2 mL, 3 mmol) were suspended in xylene (1000 mL). The solution was refluxed and stirred for 12 hours. The resultant was extracted by dichloromethane and distilled water, and the organic layer was filled in the silica-gel. After removing the organic solvent, the resultant was columned in the silica-gel such that the compound PPH15 (12 g, yield: 63%) was obtained.

9. Synthesis of the compound PNH1

(1) 2-(3-bromophenyl)-4,6-diphenyl-1,3,5-triazine

[Reaction Formula 9a]

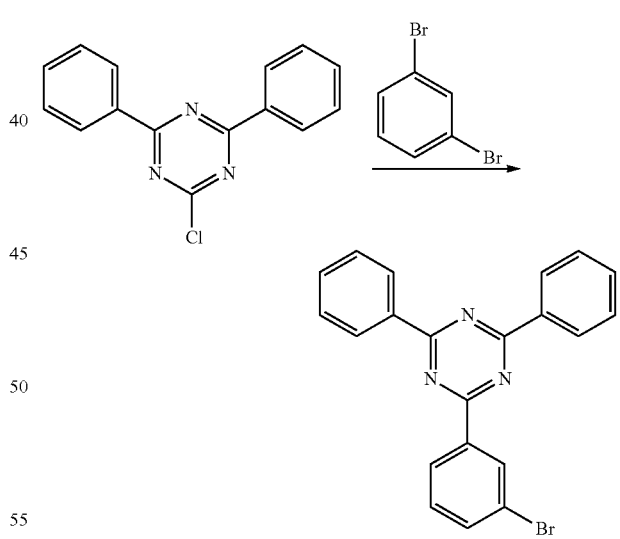

1,3-dibromobenzene was dissolved in THF and cooled into the temperature of −78° C. n-BuLi (60 mL, 2.5M) was slowly dropped into the solution, and 2-chloro-4,6-diphenyl-1,3,5-triazine (40 g, 149.7 mmol), which is dissolved in THF, was slowly dropped. The solution was slowly heated up to the room temperature and stirred for 12 hours. After completion of the reaction, the resultant was re-precipitated by THF/MeOH and MC (methylenechloride)/hexane such that 2-(3-bromophenyl)-4,6-diphenyl-1,3,5-triazine (16 g, yield: 28%) was obtained.

(2) 2,4-diphenyl-6-(3-(4,4,5,5-tetramethyl-1,3,2-dioxaborolan-2-yl)phenyl)-1,3,5-triazine

[Reaction Formula 9b]

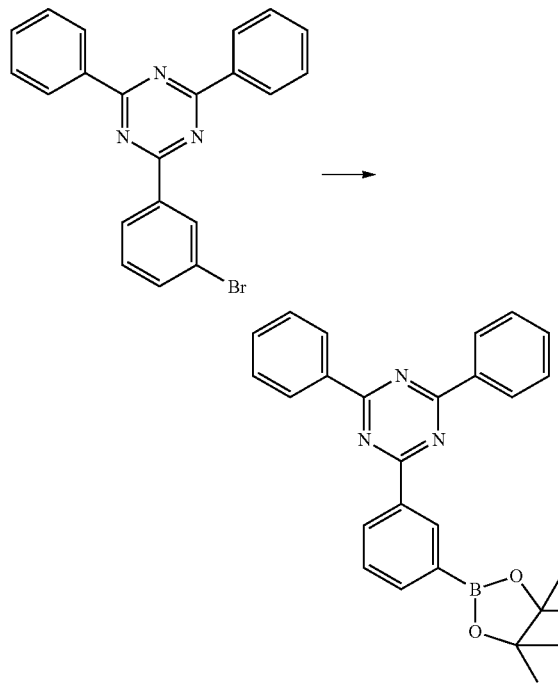

2-(3-bromophenyl)-4,6-diphenyl-1,3,5-triazine (15.8 g, 40.7 mmol), bis(pinacolato)diboron (10.4 g, 40.71 mmol), Pd2(dba)3 (1.12 g, 1.2 mmol), potassium acetate (6.0 g, 61.1 mmol) and tricyclohexylphosphine (0.8 g, 2.8 mmol) were dissolved in 1,4-dioxane and refluxed/stirred for 12 hours. After completion of the reaction, the solvent was removed. After the mixture was dissolved in hot toluene, the resultant was filter in the silica-gel such that 2,4-diphenyl-6-(3-(4,4,5,5-tetramethyl-1,3,2-dioxaborolan-2-yl)phenyl)-1,3,5-triazine (13 g, yield: 73%) was obtained.

(3) 2-(3-(4,6-diphenyl-1,3,5-triazin-2-yl)phenyl)-5H-benzofuro[3,2-c]carbazole

[Reaction Formula 9c]

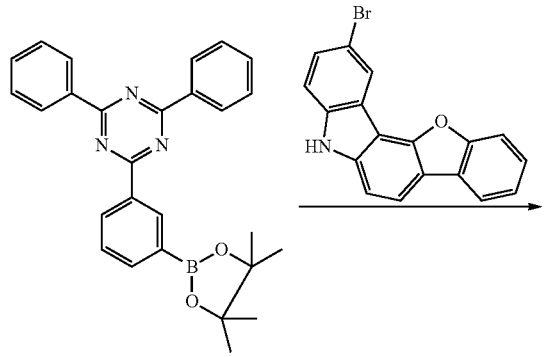

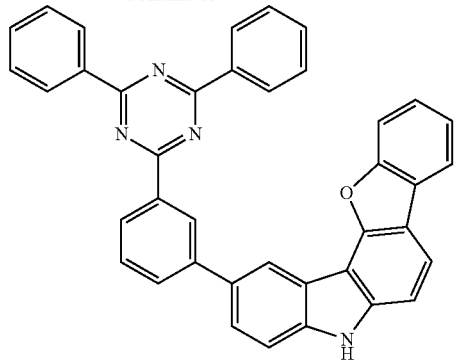

2,4-diphenyl-6-(3-(4,4,5,5-tetramethyl-1,3,2-dioxaborolan-2-yl)phenyl)-1,3,5-triazine1 (3 g, 29.86 mmol), benzofuran-carbazole derivative (13.05 g, 38.82 mmol), Pd(pph3)4 (1.04 g, 0.896 mmol) and K2CO3 (12.4 g, 89.58 mmol) were dissolved in a mixture of ethyl alcohol (150 mL), distilled water (150 mL) and THF (300 mL) and stirred for 12 hours. After the solvent was removed, the resultant was re-precipitated by THF/MeOH such that 2-(3-(4,6-diphenyl-1,3,5-triazin-2-yl)phenyl)-5H-benzofuro[3,2-c]carbazole (11 g, 65%) was obtained.

(4) The Compound PNH1

[Reaction Formula 9d]

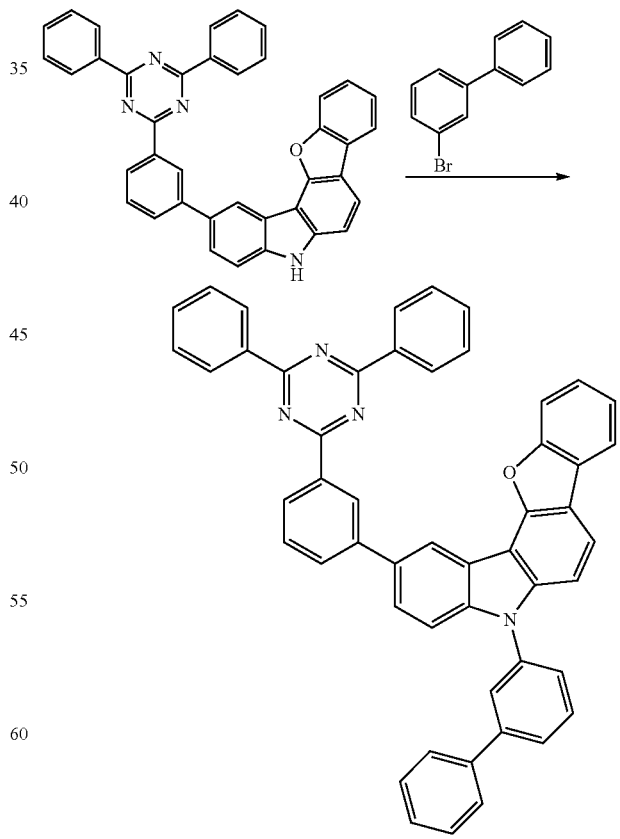

2-(3-(4,6-diphenyl-1,3,5-triazin-2-yl)phenyl)-5H-benzofuro[3,2-c]carbazole (11 g, 19.48 mmol), bromo-biphenyl (5.45 g, 23.38 mmol), Pd2(dba)3 (0.7 g, 0.799 mmol), tert-butylphosphine (0.2 g, 1.169 mmol) and tert-sodiumbutoxide (4.5 g, 46.75 mmol) were dissolved in toluene. The mixture was refluxed/stirred for 12 hours. After completion of the reaction, the resultant was columned in the silica-gel such that the compound PNH1 (3.5 g, yield: 25%) was obtained.

10. Synthesis of the compound PNH3

(1) 4-(2-nitrophenyl)dibenzo[b,d]furan

[Reaction Formula 10a]

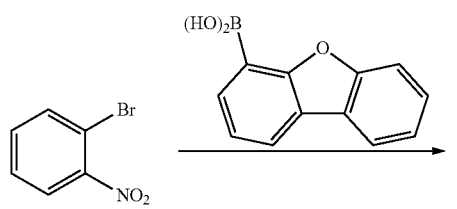

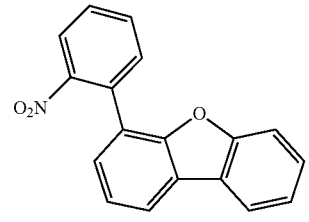

Bromonitrobenzene 20 g (99 mmol), dibenzofuran-1-yl-boronic acid (25.1 g, 118.8 mmol), Pd(pph3)4 (4.58 g, 3.96 mmol) and Na2CO3 (31.5 g, 297 mmol) were dissolved in a mixture of ethyl alcohol (148 mL) and toluene (267 mL). The mixture was refluxed/stirred for 12 hours. After completion of the reaction, the resultant was extracted by distilled water and columned in a silica-gel such that 4-(2-nitrophenyl)dibenzo[b,d]furan (29.3 g, yield: 100%) was obtained.

(2) 5H-benzofuro[3,2-c]carbazole

[Reaction Formula 10b]

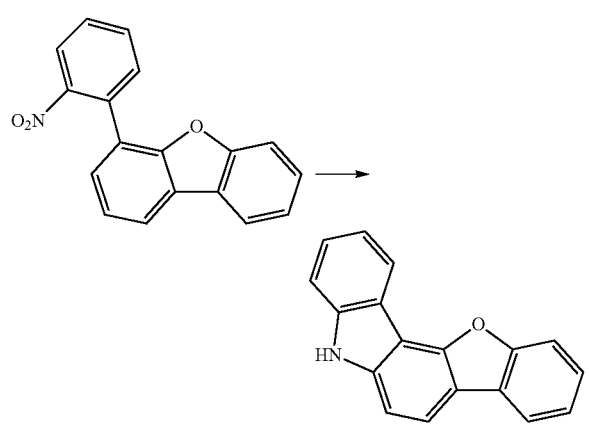

4-(2-nitrophenyl)dibenzo[b,d]furan 29.3 g (101.3 mmol) and triphenylphosphine 66.4 g (253.2 mmol) were dissolved in dichlorobenzene (210 mL). The mixture was refluxed/stirred for 12 hours. After completion of the reaction, dichlorobenzene was removed. The resultant was columned in a silica-gel and washed by methyl alcohol such that 5H-benzofuro[3,2-c]carbazole (17 g, yield: 65%) was obtained.

(3) The Compound PNH3

[Reaction Formula 10c]

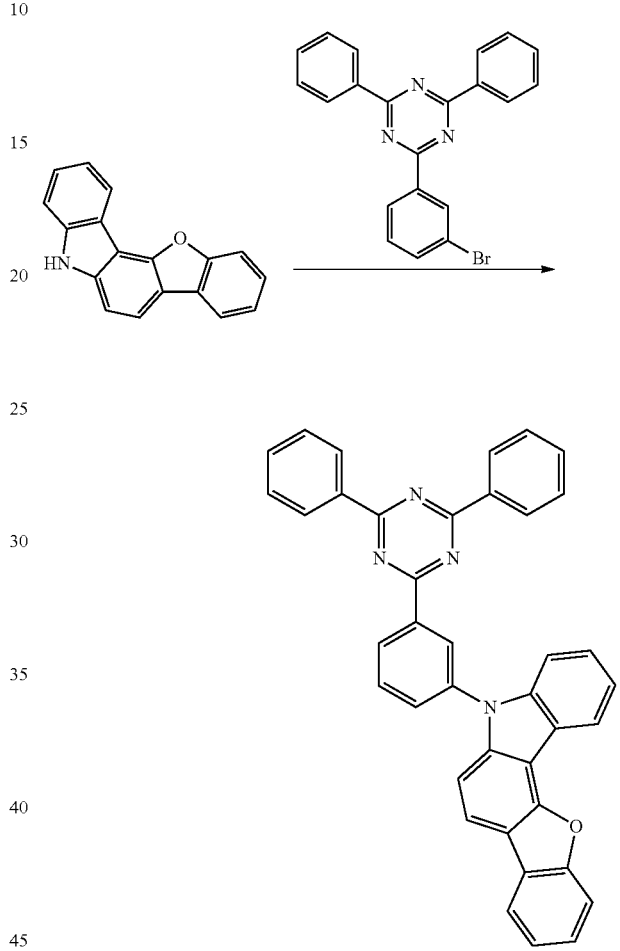

5H-benzofuro[3,2-c]carbazole (5.1 g, 19.83 mmol), triazine derivative (7 g, 18.03 mmol), Pd2(dba)3 (0.66 g, 0.72 mmol), tert-Butyl phosphine (0.2 g, 1.08 mmol) and tert-sodiumbutoxide (3.8 g, 39.7 mmol) were dissolved in toluene (150 mL). The mixture was refluxed/stirred for 12 hours. After toluene was removed, the resultant was columned in a silica-gel such that the compound PNH3 (2 g, yield: 20%) was obtained.

11. Synthesis of the Compound PNH5

[Reaction Formula 11]

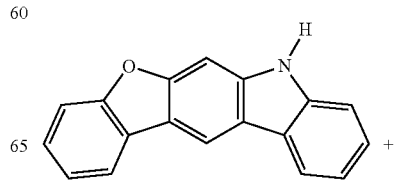

-continued

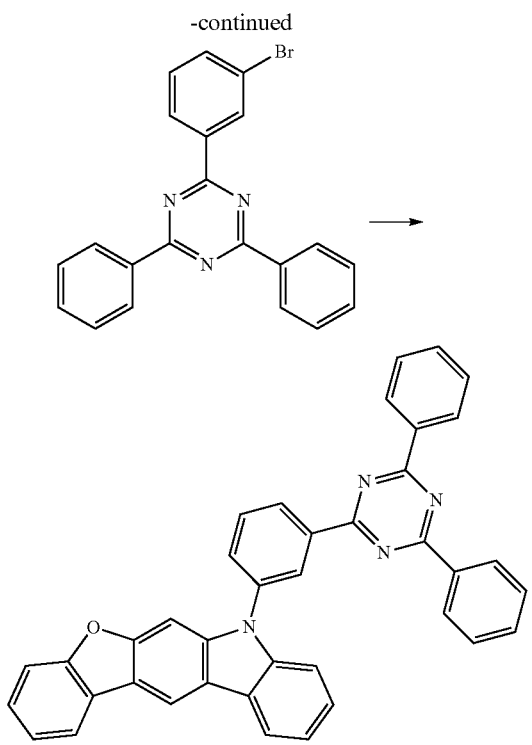

Benzofuro carbazole (15 g, 58 mmol), meta-bromophenyl triazine (23 g, 58 mmol), tert-sodiumbutoxide (11 g, 117 mmol), Pd2(dba)3 (3 g, 3 mmol) and tert-tributylphosphine (3 g, 6 mmol) were suspended in xylene (1000 mL). The solution was refluxed and stirred for 12 hours. The resultant was extracted by dichloromethane and distilled water, and the organic layer was filled in the silica-gel. After removing the organic solvent, the resultant was columned in the silica-gel such that the compound PNH5 (15 g, yield: 46%) was obtained.

12. Synthesis of the Compound PNH7

[Reaction Formula 12]

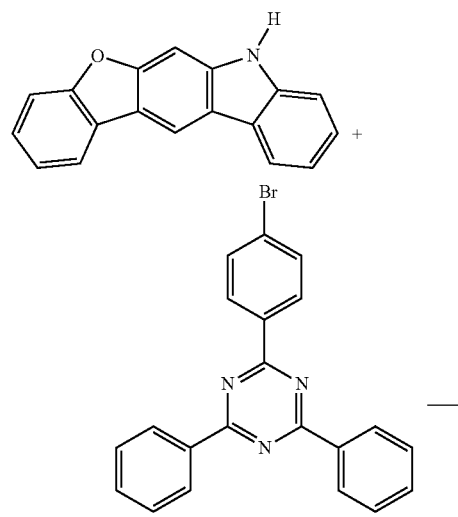

-continued

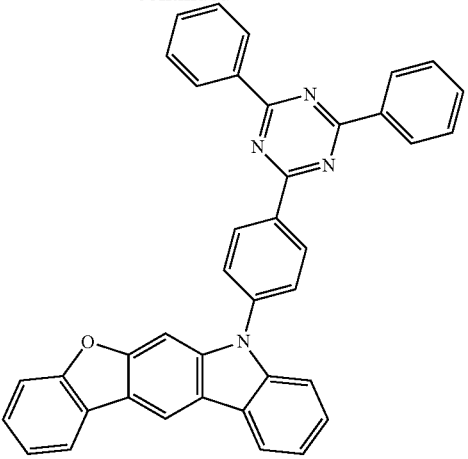

Benzofuro carbazole (15 g, 58 mmol), para-bromophenyl triazine (23 g, 58 mmol), tert-sodiumbutoxide (11 g, 117 mmol), Pd2(dba)3 (3 g, 3 mmol) and tert-tributylphosphine (3 g, 6 mmol) were suspended in xylene (1000 mL). The solution was refluxed and stirred for 12 hours. The resultant was extracted by dichloromethane and distilled water, and the organic layer was filled in the silica-gel. After removing the organic solvent, the resultant was columned in the silica-gel such that the compound PNH7 (17 g, yield: 52%) was obtained.

The related art host materials, each of which has Formulas of HOST1 and HOST2 below, were synthesized. (HOST1: 4-(3-(triphenylen-2-yl)phenyl)dibenzo[b,d]thiophene, HOST2: 3-(4,6-diphenyl-1,3,5-triazin-2-yl)-1-phenyl-1,3-dihydroindolo[2,3-b]carbazole)

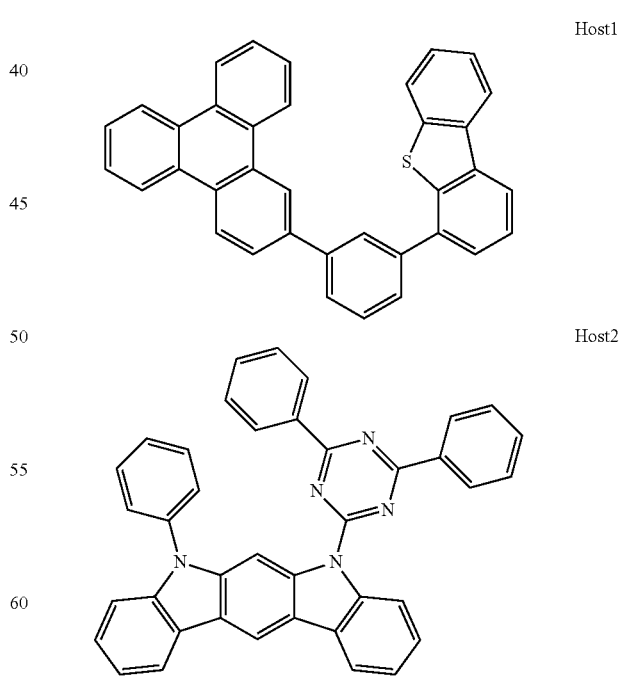

The properties, e.g., LUMO energy level, HOMO energy level and band gap energy, of the organic compound of the present invention (PPH1, PPH3, PPH5, PPH7, PPH9, PPH11, PPH13, PPH15, PNH1, PNH3, PNH5 and PNH7) and the compounds of HOST1 and HOST2 were measured and listed in Table 1.

TABLE 1

| Compounds | Band gap Energy [b] (eV) | LUMO [c] (eV) | HOMO [a] (eV) |
|---|---|---|---|
| Host1 | 3.80 | −2.20 | −6.00 |
| Host2 | 3.26 | −2.23 | −5.49 |
| PPH1 | 3.30 | −2.08 | −5.38 |
| PPH3 | 3.30 | −2.05 | −5.34 |
| PPH5 | 3.28 | −1.78 | −5.06 |
| PPH7 | 3.33 | −2.01 | −5.34 |
| PPH9 | 3.28 | −2.19 | −5.47 |
| PPH11 | 3.20 | −2.04 | −5.24 |
| PPH13 | 3.19 | −1.72 | −4.91 |
| PPH15 | 3.16 | −1.70 | −4.86 |
| PNH1 | 3.34 | −2.34 | −5.68 |
| PNH3 | 3.44 | −2.29 | −5.73 |
| PNH5 | 3.54 | −2.11 | −5.65 |
| PNH7 | 3.12 | −2.51 | −5.63 |

[a] Absorption onset of 0.02 mM solutions in $CH_2Cl_2$.
[b] Estimated from the absorption onset.
[c] LUMO = −[Band gap energy − HOMO level]

As shown in Table 1, the band gap energy of the organic compound of the present invention is smaller than that of the HOST1 compound, while the band gap energy of the organic compound of the present invention is similar to or slightly larger than that of the HOST2 compound. Accordingly, the organic compound of the present invention has sufficient band gap energy for the host in the EML of the organic light emitting diode.

Organic Light Emitting Diode

1. EXAMPLE 1

An organic light emitting diode having a structure of ITO layer (a reflective anode), an HIL, an HTL1, an HTL2, an EBL, an EML, an ETL, an EIL, a cathode and a capping layer (CPL). A substrate, where an ITO layer including a reflection plate is patterned to form the anode (10 mm*40 mm and a thickness of 0.5 mm), is ultrasonically washed (or cleaned) by isopropyl alcohol, acetone and distilled water for 5 minutes and dried in the oven of the temperature of 100° C. After the substrate is treated by $O_2$ plasma for 2 minutes, the substrate is loaded in a deposition chamber. Under the vacuum of about $1*10^{-7}$ Torr, following layers are sequentially deposited using a hating boat.
(a) HIL: (HIL compound (3 wt %) and HTL1 compound (97 wt %), 100 Å),
(b) HTL1: (HTL1 compound, 1200 Å),
(c) HTL2: (HTL2 compound, 250 Å),
(d) EBL: (EBL compound, 150 Å),
(e) EML: (first host (PPH1), second host (HOST2) and G-dopant (D7 compound in above Formula 10, 5 wt % doping), (first host:second host=1:1), 400 Å),
f) ETL: (ETL compound/Liq (wt % ratio=2:1), 300 Å),
(g) EIL (Mg/LiF (wt % ratio=3:1, 30 Å),
(h) cathode (Ag/Mg (wt % ratio=4:1, 140 Å) and
(i) CPL The deposited structure is loaded in the drying box and encapsuled by an UV-cured expoxy and a getter. The organic light emitting diode has an emitting area of 9 mm2. The Formulas of the compound HIL, the compound HTL1, the compound HTL2, the compound EBL, the compound ETL and the compound Liq are shown below.

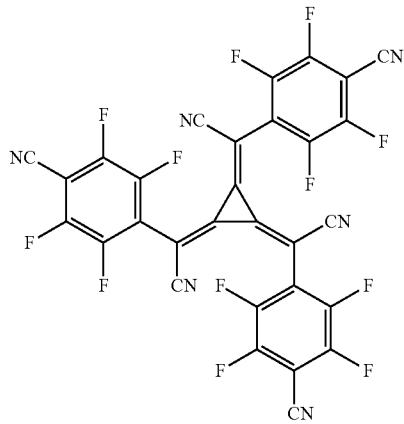

HIL

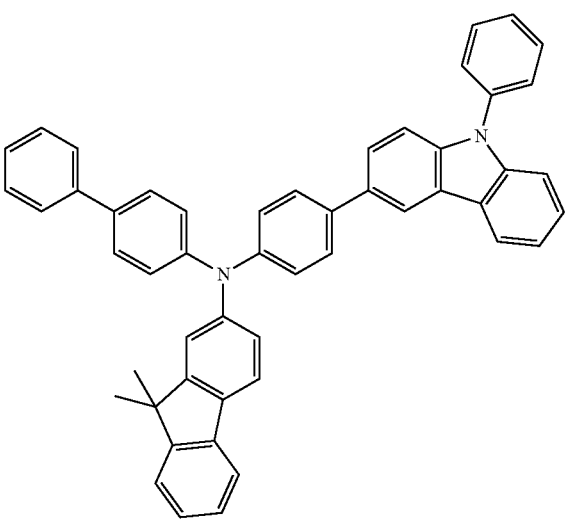

HTL1

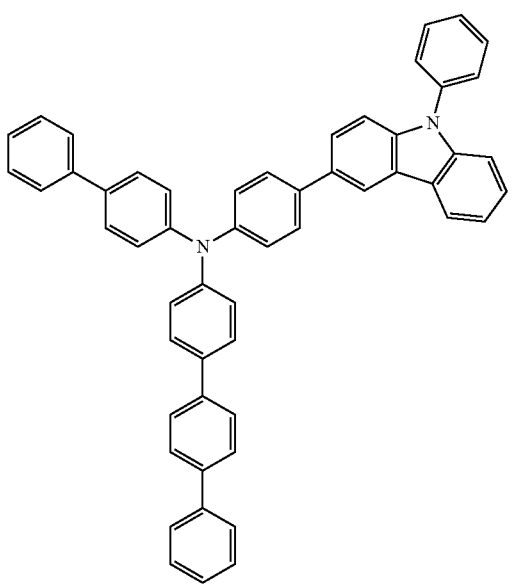

HTL2

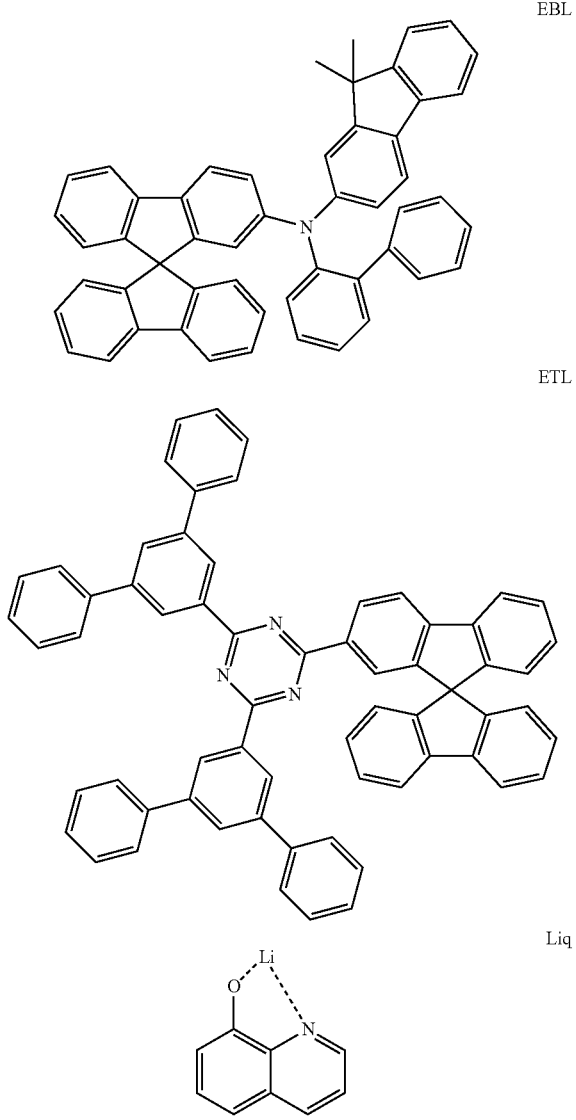

2. EXAMPLES 2 TO 16

Ex2 to Ex16

Instead of the first host and the second host, the compound PPH5 and the compound HOST2 (Ex2), the compound HOST1 and the compound PNH1 (Ex3), the compound HOST1 and the compound PNH3 (Ex4), the compound HOST1 and the compound PNH5 (Ex5), the compound HOST1 and the compound PNH7 (Ex6), the compound PPH1 and the compound PNH1 (Ex7), the compound PPH1 and the compound PNH7 (Ex8), the compound PPH5 and the compound PNH1 (Ex9), the compound PPH5 and the compound PNH7 (Ex10), the compound PPH3 and the compound PNH7 (Ex11), the compound PPH7 and the compound PNH7 (Ex12), the compound PPH9 and the compound PNH7 (Ex13), the compound PPH13 and the compound PNH7 (Ex14), the compound PPH15 and the compound PNH7 (Ex15) and the compound PPH1 and the compound PNH5 (Ex16) are respectively used.

3. COMPARATIVE EXAMPLE 1

Ref1

Instead of the first host and the second host, the compound HOST1 and the compound HOST2 are used.

The EL property of the organic light emitting diode in "Example 1" to "Example 16" and "Comparative Example 1" is measured using the current supply "KEITHLEY" and the photometer "PR 650" under the room temperature and listed in Table 2. The driving voltage, the efficiency (Cd/A) and the CIE color coordinate index of the organic light emitting diodes are measured with a reference luminance of 8000 nit, and the lifetime (T95) from 100% to 95% are measured with 20000 nit reference luminance constant current.

TABLE 2

|      | V    | Cd/A  | CIE(x, y)    | T95 [hr] |
|------|------|-------|--------------|----------|
| Ref1 | 4.75 | 131.4 | 0.196, 0.725 | 190      |
| Ex1  | 4.10 | 135.0 | 0.216, 0.723 | 240      |
| Ex2  | 4.03 | 133.7 | 0.244, 0.709 | 200      |
| Ex3  | 4.49 | 115.2 | 0.270, 0.703 | 280      |
| Ex4  | 4.54 | 119.3 | 0.276, 0.710 | 190      |
| Ex5  | 4.18 | 131.4 | 0.196, 0.725 | 170      |
| Ex6  | 4.09 | 156.4 | 0.217, 0.725 | 250      |
| Ex7  | 4.10 | 138.5 | 0.237, 0.729 | 420      |
| Ex8  | 4.06 | 146.3 | 0.231, 0.724 | 350      |
| Ex9  | 4.05 | 148.2 | 0.226, 0.726 | 480      |
| Ex10 | 4.08 | 145.2 | 0.222, 0.723 | 380      |
| Ex11 | 4.10 | 142.3 | 0.226, 0.727 | 300      |
| Ex12 | 4.15 | 140.5 | 0.221, 0.713 | 330      |
| Ex13 | 4.07 | 144.2 | 0.220, 0.726 | 340      |
| Ex14 | 4.11 | 132.4 | 0.230, 0.715 | 280      |
| Ex15 | 4.27 | 133.0 | 0.241, 0.709 | 290      |
| Ex16 | 4.15 | 137.4 | 0.221, 0.715 | 320      |

As shown in Table 2, in comparison to "Comparative Example 1 (Ref)", the driving voltage of the organic light emitting diode of the present invention (Ex1 to Ex16) is reduced.

For example, when the PPH1 compound as a P-type host, the PPH5 compound as a P-type host or the PNH1 compound as an N-type host is used with the related art host material, i.e., HOST1 compound or HOST2 compound, the emitting efficiency and the lifetime of the organic light emitting diode are further improved.

In addition, when the first organic compound and the second organic compound of the present invention are used for the two-host system (Ex7 to Ex16), there are remarkable advantages in the driving voltage, the efficiency and the lifetime of the organic light emitting diode.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An organic compound, represented by following Formula 3b:

[Formula 3b]

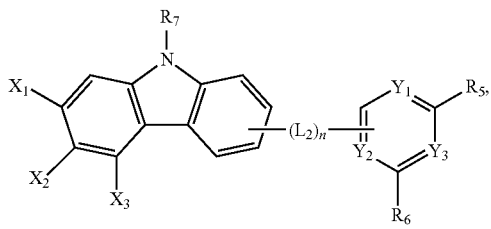

wherein each of $R_5$ to $R_6$ is independently selected from the group consisting of hydrogen, deuterium, tritium, $C_5$ to $C_{30}$ aryl group, substituted $C_5$ to $C_{30}$ heteroaryl group, non-substituted $C_5$ to $C_{30}$ heteroaryl group, substituted $C_6$ to $C_{30}$ arylalkyl group, non-substituted $C_6$ to $C_{30}$ arylalkyl group, substituted $C_6$ to $C_{30}$ hetero-arylalkyl group, non-substituted $C_6$ to $C_{30}$ hetero-arylalkyl group, non-substituted $C_6$ to $C_{30}$ aryloxyl group, substituted $C_6$ to $C_{30}$ hetero-aryloxyl group, and non-substituted $C_6$ to $C_{30}$ hetero-aryloxyl group, wherein $R_7$ is hydrogen, deuterium, tritium, $C_5$ to $C_{30}$ aryl group, substituted $C_6$ to $C_{30}$ arylalkyl group, non-substituted $C_6$ to $C_{30}$ arylalkyl group or non-substituted $C_6$ to $C_{30}$ aryloxyl group, wherein each of $Y_1$ to $Y_3$ is independently N or $CR_8$, and at least one of $Y_1$ to $Y_3$ is N, wherein $R_8$ is selected from the group consisting of hydrogen, deuterium, tritium, $C_5$ to $C_{30}$ aryl group, substituted $C_5$ to $C_{30}$ heteroaryl group, non-substituted $C_5$ to $C_{30}$ heteroaryl group, substituted $C_6$ to $C_{30}$ arylalkyl group, non-substituted $C_6$ to $C_{30}$ arylalkyl group, substituted $C_6$ to $C_{30}$ hetero-arylalkyl group, non-substituted $C_6$ to $C_{30}$ hetero-arylalkyl group, non-substituted $C_6$ to $C_{30}$ aryloxyl group, substituted $C_6$ to $C_{30}$ hetero-aryloxyl group, and non-substituted $C_6$ to $C_{30}$ hetero-aryloxyl group, wherein $X_2$ with one of $X_1$ and $X_3$ forms a $C_4$ to $C_{30}$ homo fused-ring or a $C_4$ to $C_{30}$ hetero fused-ring, and the other one of $X_1$ and $X_3$ is selected from the group consisting of hydrogen, deuterium, tritium, substituted $C_1$ to $C_{20}$ alkyl group, non-substituted $C_1$ to $C_{20}$ alkyl group, substituted $C_1$ to $C_{20}$ alkoxy group, non-substituted $C_1$ to $C_{20}$ alkoxy group, substituted $C_5$ to $C_{30}$ aryl group, non-substituted $C_5$ to $C_{30}$ aryl group, substituted $C_5$ to $C_{30}$ heteroaryl group, and non-substituted $C_5$ to $C_{30}$ heteroaryl group, and wherein $L_2$ is selected from the group consisting of substituted $C_1$ to $C_{30}$ alkylene group, non-substituted $C_1$ to $C_{30}$ alkylene group, substituted $C_3$ to $C_{30}$ cycloalkylene group, non-substituted $C_3$ to $C_{30}$ cyclo-alkylene group, substituted $C_5$ to $C_{30}$ arylene group, non-substituted $C_5$ to $C_{30}$ arylene group, substituted $C_4$ to $C_{30}$ heteroarylene group, substituted $C_6$ to $C_{30}$ arylalkylene group, non-substituted $C_6$ to $C_{30}$ arylalkylene group, substituted $C_6$ to $C_{30}$ hetero-arylalkylene group, non-substituted $C_6$ to $C_{30}$ hetero-arylalkylene group, substituted $C_6$ to $C_{30}$ aryloxylene group, non-substituted $C_6$ to $C_{30}$ aryloxylene group, substituted $C_6$ to $C_{30}$ hetero-aryloxylene group, and non-substituted $C_6$ to $C_{30}$ hetero-aryloxylene group, and n is 0 or 1, with the proviso that when $X_1$ and $X_2$ join together to form a $C_4$ to $C_{30}$ hetero fused-ring, they do not form a benzodioxan group.

2. The organic compound according to claim 1, wherein the organic compound is selected from:

PNH1

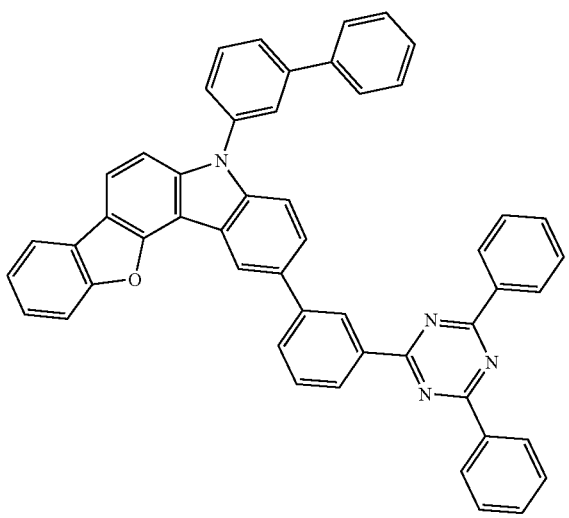

PNH2

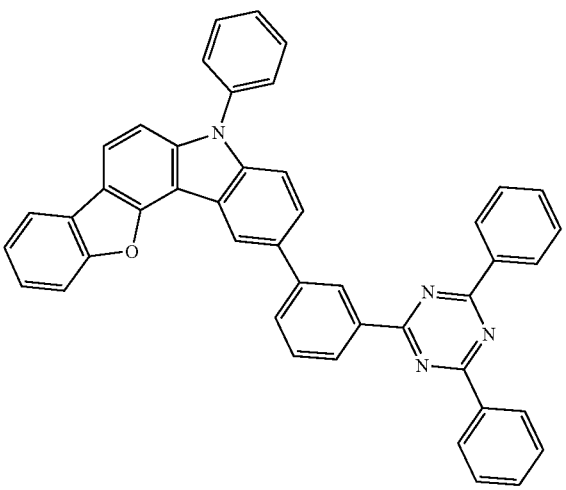

-continued

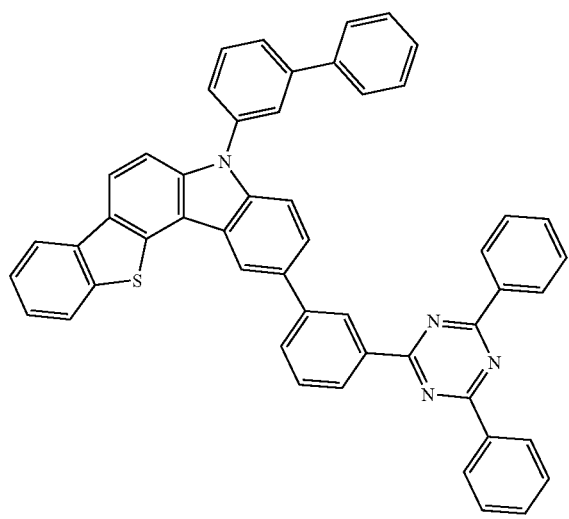

PNH9

PNH10

3. An organic light emitting diode, comprising:
a first electrode;
a second electrode facing the first electrode; and
an organic layer between the first electrode and the second electrode, wherein the organic layer includes the organic compound of claim 1.

4. The organic light emitting diode according to claim 3, wherein the organic layer includes an emitting material layer, a hole auxiliary layer between the first electrode and the emitting material layer and an electron auxiliary layer between the second electrode and the emitting material layer.

5. The organic light emitting diode according to claim 4, wherein the emitting material layer includes the organic compound as a host.

6. The organic light emitting diode according to claim 5, wherein the emitting material layer further includes a dopant represented by following Formulas 4a or 4b:

[Formula 4a]

[Formula 4b]

wherein in Formula 4a, each of $R_{21}$ to $R_{29}$ is independently selected from the group consisting of hydrogen, deuterium, tritium, halogen, substituted $C_1$ to $C_{30}$ alkyl group, non-substituted $C_1$ to $C_{30}$ alkyl group, cyano group, substituted $C_3$ to $C_{30}$ cyclo-alkyl group, non-substituted $C_3$ to $C_{30}$ cyclo-alkyl group, substituted $C_3$ to $C_{30}$ hetero cyclo-alkyl group, non-substituted $C_3$ to $C_{30}$ hetero cyclo-alkyl group, substituted $C_5$ to $C_{30}$ aryl group, non-substituted $C_5$ to $C_{30}$ aryl group, substituted $C_5$ to $C_{30}$ heteroaryl group, non-substituted $C_5$ to $C_{30}$ heteroaryl group, substituted $C_6$ to $C_{30}$ arylalkyl group, non-substituted $C_6$ to $C_{30}$ arylalkyl group, substituted $C_6$ to $C_{30}$ hetero-arylalkyl group, non-substituted $C_6$ to $C_{30}$ hetero-arylalkyl group, substituted $C_6$ to $C_{30}$ aryloxyl group, non-substituted $C_6$ to $C_{30}$ aryloxyl group, substituted $C_6$ to $C_{30}$ hetero-aryloxyl group, and non-substituted $C_6$ to $C_{30}$ hetero-aryloxyl group, wherein $R_{30}$ is selected from the group consisting of hydrogen, deuterium, tritium and substituted $C_1$ to $C_{30}$ alkyl group, and non-substituted $C_1$ to $C_{30}$ alkyl group, and r is an integer of 1 to 4, wherein in Formula 4b, each of $R_{31}$ to $R_{38}$ is independently selected from the group consisting of hydrogen, deuterium, tritium, halogen, substituted $C_1$ to $C_{30}$ alkyl group, non-substituted $C_1$ to $C_{30}$ alkyl group, cyano group, substituted $C_3$ to $C_{30}$ cyclo-alkyl group, non-substituted $C_3$ to $C_{30}$ cyclo-alkyl group, substituted $C_3$ to $C_{30}$ hetero cyclo-alkyl group, non-substituted $C_3$ to $C_{30}$ hetero cyclo-alkyl group, substituted $C_5$ to $C_{30}$ aryl group, non-substituted $C_5$ to $C_{30}$ aryl group, substituted $C_5$ to $C_{30}$ heteroaryl group, non-substituted $C_5$ to $C_{30}$ heteroaryl group, substituted $C_6$ to $C_{30}$ arylalkyl group, non-substituted $C_6$ to $C_{30}$ arylalkyl group, substituted $C_6$ to $C_{30}$ hetero-arylalkyl group, non-substituted $C_6$ to $C_{30}$ hetero-arylalkyl group, substituted $C_6$ to $C_{30}$ aryloxyl group, non-substituted $C_6$ to $C_{30}$ aryloxyl group, substituted $C_6$ to $C_{30}$ hetero-aryloxyl group, and non-substituted $C_6$ to $C_{30}$ hetero-aryloxyl group, or adjacent two of $R_{31}$ to $R_{38}$ form a fused aromatic ring of $C_5$ to $C_{30}$, wherein in Formulas 4a and 4b, n is an integer of 1 to 3, and L is represented by Formula 5:

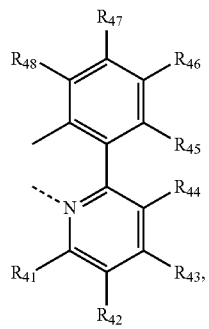

[Formula 5]

wherein each of $R_{41}$ to $R_{48}$ is independently selected from the group consisting of hydrogen, deuterium, tritium, halogen, substituted $C_1$ to $C_{30}$ alkyl group, non-substituted $C_1$ to $C_{30}$ alkyl group, cyano group, substituted $C_3$ to $C_{30}$ cyclo-alkyl group, non-substituted $C_3$ to $C_{30}$ cyclo-alkyl group, substituted $C_3$ to $C_{30}$ hetero cyclo-alkyl group, non-substituted $C_3$ to $C_{30}$ hetero cyclo-alkyl group, substituted $C_5$ to $C_{30}$ aryl group, non-substituted $C_5$ to $C_{30}$ aryl group, substituted $C_5$ to $C_{30}$ heteroaryl group, non-substituted $C_5$ to $C_{30}$ heteroaryl group, substituted $C_6$ to $C_{30}$ arylalkyl group, non-substituted $C_6$ to $C_{30}$ arylalkyl group, substituted $C_6$ to $C_{30}$ hetero-arylalkyl group, non-substituted $C_6$ to $C_{30}$ hetero-arylalkyl group, substituted $C_6$ to $C_{30}$ aryloxyl group, non-substituted $C_6$ to $C_{30}$ aryloxyl group, substituted $C_6$ to $C_{30}$ hetero-aryloxyl group, and non-substituted $C_6$ to $C_{30}$ hetero-aryloxyl group, or adjacent two of $R_{41}$ to $R_{48}$ form a fused aromatic ring of $C_5$ to $C_{30}$.

7. An organic light emitting display device, comprising:

a substrate;

the organic light emitting diode of claim 3: and a thin film transistor between the substrate and the organic light emitting diode and connected to the organic light emitting diode.

8. An organic light emitting diode, comprising:

a first electrode;

a second electrode facing the first electrode; and an organic layer between the first electrode and the second electrode, wherein the organic layer includes an organic compound represented by following Formula 2 as a first host, and an organic compound represented by one of following Formulas 3a or 3b as a second host and, a dopant

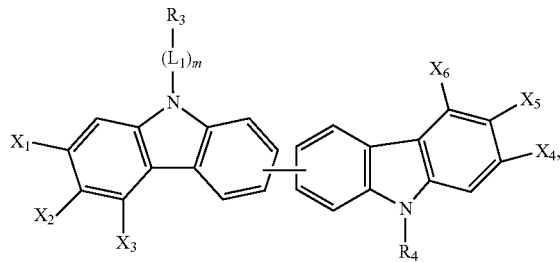

[Formula 2]

wherein each of $R_3$ and $R_4$ is independently selected from the group consisting of hydrogen, deuterium, tritium, $C_5$ to $C_{30}$ aryl group, substituted $C_5$ to $C_{30}$ heteroaryl group, non-substituted $C_5$ to $C_{30}$ heteroaryl group, substituted $C_6$ to $C_{30}$ arylalkyl group, non-substituted $C_6$ to $C_{30}$ arylalkyl group, substituted $C_6$ to $C_{30}$ hetero-arylalkyl group, non-substituted $C_6$ to $C_{30}$ hetero-arylalkyl group, non-substituted $C_6$ to $C_{30}$ aryloxyl group, substituted $C_6$ to $C_{30}$ hetero-aryloxyl group, and non-substituted $C_6$ to $C_{30}$ hetero-aryloxyl group, wherein $X_5$ with one of $X_4$ and $X_6$ forms a $C_4$ to $C_{30}$ homo fused-ring or a $C_4$ to $C_{30}$ hetero fused-ring, or each of $X_4$ to $X_6$ is selected from the group consisting of hydrogen, deuterium, tritium, substituted $C_1$ to $C_{20}$ alkyl group, non-substituted $C_1$ to $C_{20}$ alkyl group, substituted $C_1$ to $C_{20}$ alkoxy group, non-substituted $C_1$ to $C_{20}$ alkoxy group, substituted $C_5$ to $C_{30}$ aryl group, non-substituted $C_5$ to $C_{30}$ aryl group, substituted $C_5$ to $C_{30}$ heteroaryl group, and non-substituted $C_5$ to $C_{30}$ heteroaryl group, wherein $L_1$ is selected from the group consisting of substituted $C_1$ to $C_{30}$ alkylene group, non-substituted $C_1$ to $C_{30}$ alkylene group, substituted $C_3$ to $C_{30}$ cyclo-alkylene group, non-substituted $C_3$ to $C_{30}$ cyclo-alkylene group, substituted $C_5$ to $C_{30}$ arylene group, non-substituted $C_5$ to $C_{30}$ arylene group, substituted $C_4$ to $C_{30}$ heteroarylene group, non-substituted $C_4$ to $C_{30}$ heteroarylene group, substituted $C_6$ to $C_{30}$ arylalkylene group, non-substituted $C_6$ to $C_{30}$ arylalkylene group, substituted $C_6$ to $C_{30}$ hetero-arylalkylene group, non-substituted $C_6$ to $C_{30}$ hetero-arylalkylene group, substituted $C_6$ to $C_{30}$ aryloxylene group, non-substituted $C_6$ to $C_{30}$ aryloxylene group, substituted $C_6$ to $C_{30}$ hetero-aryloxylene group, and non-substituted $C_6$ to $C_{30}$ hetero-aryloxylene group, and m is 0 or 1, and wherein $X_2$ with one of $X_1$ and $X_3$ forms a $C_4$ to $C_{30}$ homo fused-ring or a $C_4$ to $C_{30}$ hetero fused-ring, and the other one of $X_1$ and $X_3$ is selected from the group consisting of hydrogen, deuterium, tritium, substituted $C_1$ to $C_{20}$ alkyl group, non-substituted $C_1$ to $C_{20}$ alkyl group, substituted $C_1$ to $C_{20}$ alkoxy group, non-substituted $C_1$ to $C_{20}$ alkoxy group, substituted $C_5$ to $C_{30}$ aryl group, non-substituted $C_5$ to $C_{30}$ aryl group, substituted $C_5$ to $C_{30}$ heteroaryl group, and non-substituted $C_5$ to $C_{30}$ heteroaryl group,

[Formula 3a]

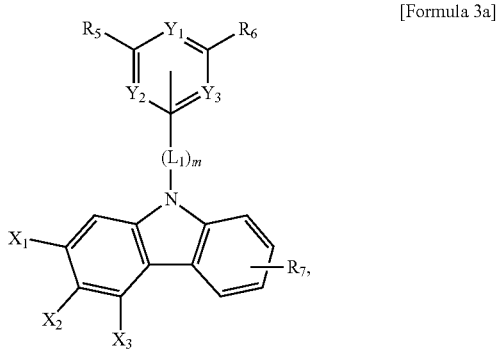

[Formula 3b]

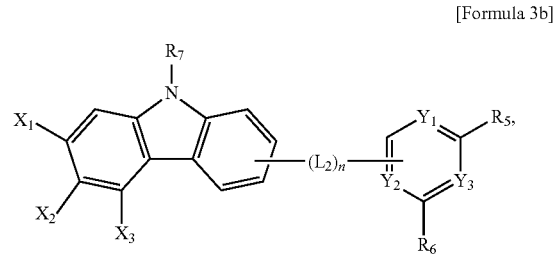

wherein each of $R_5$ to $R_6$ is independently selected from the group consisting of hydrogen, deuterium, tritium, $C_5$ to $C_{30}$ aryl group, substituted $C_5$ to $C_{30}$ heteroaryl group, non-substituted $C_5$ to $C_{30}$ heteroaryl group, substituted $C_6$ to $C_{30}$ arylalkyl group, non-substituted $C_6$ to $C_{30}$ arylalkyl group, substituted $C_6$ to $C_{30}$ hetero-arylalkyl group, non-substituted $C_6$ to $C_{30}$ hetero-arylalkyl group, non-substituted $C_6$ to $C_{30}$ aryloxyl group, substituted $C_6$ to $C_{30}$ hetero-aryloxyl group, and non-substituted $C_6$ to $C_{30}$ hetero-aryloxyl group, wherein $R_7$ is hydrogen, deuterium, tritium, $C_5$ to $C_{30}$ aryl group, substituted $C_6$ to $C_{30}$ arylalkyl group, non-substituted $C_6$ to $C_{30}$ arylalkyl group or non-substituted $C_6$ to $C_{30}$ aryloxyl group, wherein each of $Y_1$ to $Y_3$ is independently N or $CR_8$, and at least one of $Y_1$ to $Y_3$ is N, wherein $R_8$ is selected from the group consisting of hydrogen, deuterium, tritium, $C_5$ to $C_{30}$ aryl group, substituted $C_5$ to $C_{30}$ heteroaryl group, non-substituted $C_5$ to $C_{30}$ heteroaryl group, substituted $C_6$ to $C_{30}$ arylalkyl group, non-substituted $C_6$ to $C_{30}$ arylalkyl group, substituted $C_6$ to $C_{30}$ hetero-arylalkyl group, non-substituted $C_6$ to $C_{30}$ hetero-arylalkyl group, non-substituted $C_6$ to $C_{30}$ aryloxyl group, substituted $C_6$ to $C_{30}$ hetero-aryloxyl group, and non-substituted $C_6$ to $C_{30}$ hetero-aryloxyl group, wherein $L_1$ is selected from the group consisting of substituted $C_1$ to $C_{30}$ alkylene group, non-substituted $C_1$ to $C_{30}$ alkylene group, substituted $C_3$ to $C_{30}$ cyclo-alkylene group, non-substituted $C_3$ to $C_{30}$ cyclo-alkylene group, substituted $C_5$ to $C_{30}$ arylene group, non-substituted $C_5$ to $C_{30}$ arylene group, substituted $C_4$ to $C_{30}$ heteroarylene group, non-substituted $C_4$ to $C_{30}$ heteroarylene group, substituted $C_6$ to $C_{30}$ arylalkylene group, non-substituted $C_6$ to $C_{30}$ arylalkylene group, substituted $C_6$ to $C_{30}$ hetero-arylalkylene group, non-substituted $C_6$ to $C_{30}$ hetero-arylalkylene group, substituted $C_6$ to $C_{30}$ aryloxylene group, non-substituted $C_6$ to $C_{30}$ aryloxylene group, substituted $C_6$ to $C_{30}$ hetero-aryloxylene group, and non-substituted $C_6$ to $C_{30}$ hetero-aryloxylene group, and m is 0 or 1, and wherein $X_2$ with one of $X_1$ and $X_3$ forms a $C_4$ to $C_{30}$ homo fused-ring or a $C_4$ to $C_{30}$ hetero fused-ring, and the other one of $X_1$ and $X_3$ is selected from the group consisting of hydrogen, deuterium, tritium, substituted $C_1$ to $C_{20}$ alkyl group, non-substituted $C_1$ to $C_{20}$ alkyl group, substituted $C_1$ to $C_{20}$ alkoxy group, non-substituted $C_1$ to $C_{20}$ alkoxy group, substituted $C_5$ to $C_{30}$ aryl group, non-substituted $C_5$ to $C_{30}$ aryl group, substituted $C_5$ to $C_{30}$ heteroaryl group, and non-substituted $C_5$ to $C_{30}$ heteroaryl group, and wherein each of $R_5$ to $R_7$ is independently selected from the group consisting of hydrogen, deuterium, tritium, $C_5$ to $C_{30}$ aryl group, substituted $C_5$ to $C_{30}$ heteroaryl group, non-substituted $C_5$ to $C_{30}$ heteroaryl group, substituted $C_6$ to $C_{30}$ arylalkyl group, non-substituted $C_6$ to $C_{30}$ arylalkyl group, substituted $C_6$ to $C_{30}$ hetero-arylalkyl group, non-substituted $C_6$ to $C_{30}$ hetero-arylalkyl group, non-substituted $C_6$ to $C_{30}$ aryloxyl group, substituted $C_6$ to $C_{30}$ hetero-aryloxyl group, and non-substituted $C_6$ to $C_{30}$ hetero-aryloxyl group, wherein each of $Y_1$ to $Y_3$ is independently N or $CR_8$, and at least one of $Y_1$ to $Y_3$ is N, wherein $R_8$ is selected from the group consisting of hydrogen, deuterium, tritium, $C_5$ to $C_{30}$ aryl group, substituted $C_5$ to $C_{30}$ heteroaryl group, non-substituted $C_5$ to $C_{30}$ heteroaryl group, substituted $C_6$ to $C_{30}$ arylalkyl group, non-substituted $C_6$ to $C_{30}$ arylalkyl group, substituted $C_6$ to $C_{30}$ hetero-arylalkyl group, non-substituted $C_6$ to $C_{30}$ hetero-arylalkyl group, non-substituted $C_6$ to $C_{30}$ aryloxyl group, substituted $C_6$ to $C_{30}$ hetero-aryloxyl group, and non-substituted $C_6$ to $C_{30}$ hetero-aryloxyl group, wherein $X_2$ with one of $X_1$ and $X_3$ forms a $C_4$ to $C_{30}$ homo fused-ring or a $C_4$ to $C_{30}$ hetero fused-ring, and the other one of $X_1$ and $X_3$ is selected from the group consisting of hydrogen, deuterium, tritium, substituted $C_1$ to $C_{20}$ alkyl group, non-substituted $C_1$ to $C_{20}$ alkyl group, substituted $C_1$ to $C_{20}$ alkoxy group, non-substituted $C_1$ to $C_{20}$ alkoxy group, substituted $C_5$ to $C_{30}$ aryl group, non-substituted $C_5$ to $C_{30}$ aryl group, substituted $C_5$ to $C_{30}$ heteroaryl group, and non-substituted $C_5$ to $C_{30}$ heteroaryl group, and wherein $L_2$ is selected from the group consisting of substituted $C_1$ to $C_{30}$ alkylene group, non-substituted $C_1$ to $C_{30}$ alkylene group, substituted $C_3$ to $C_{30}$ cyclo-alkylene group, non-substituted $C_3$ to $C_{30}$ cyclo-alkylene group, substituted $C_5$ to $C_{30}$ arylene group, non-substituted $C_5$ to $C_{30}$ arylene group, substituted $C_4$ to $C_{30}$ heteroarylene group, substituted $C_6$ to $C_{30}$ arylalkylene group, non-substituted $C_6$ to $C_{30}$ arylalkylene group, substituted $C_6$ to $C_{30}$ hetero-arylalkylene group, non-substituted $C_6$ to $C_{30}$ hetero-arylalkylene group, substituted $C_6$ to $C_{30}$ aryloxylene group, non-substituted $C_6$ to $C_{30}$ aryloxylene group, substituted $C_6$ to $C_{30}$ hetero-aryloxylene group, and non-substituted $C_6$ to $C_{30}$ hetero-aryloxylene group, and n is 0 or 1, with the proviso in Formula 3b that when $X_1$ and $X_2$ join together to form a $C_4$ to $C_{30}$ hetero fused-ring, they do not form a benzodioxan group.

9. The organic light emitting diode according to claim 8, wherein the first dopant and the second dopant have the same weight %.

10. An organic light emitting display device, comprising:
a substrate;
the organic light emitting diode of claim 8: and
a thin film transistor between the substrate and the organic light emitting diode and connected to the organic light emitting diode.

11. The organic light emitting diode according to claim 8, wherein the second host includes the organic compound represented by Formula 3b.

12. The organic light emitting diode according to claim 11, wherein the second host is selected from:

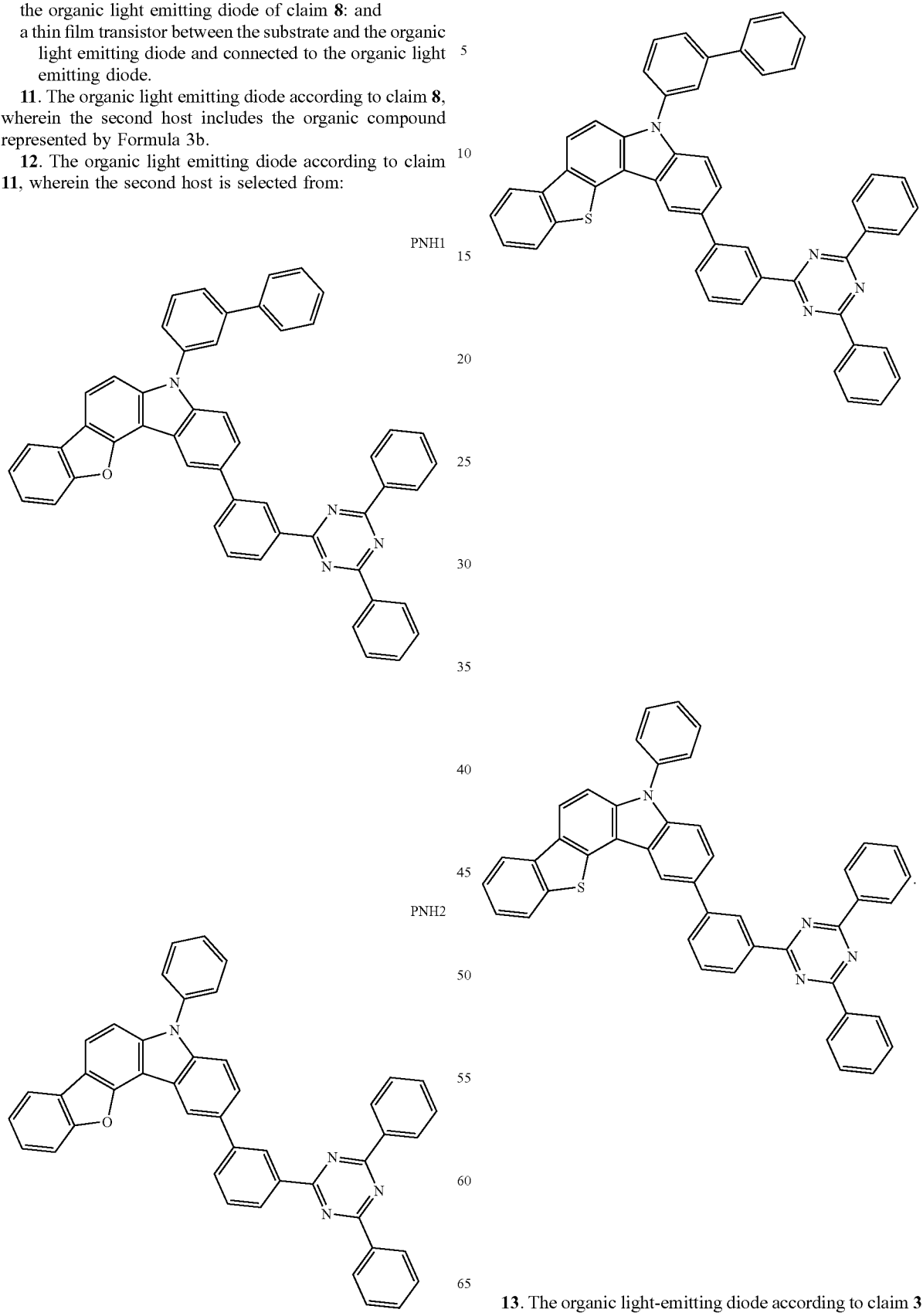

13. The organic light-emitting diode according to claim 3, wherein the organic compound is selected from:

PNH1
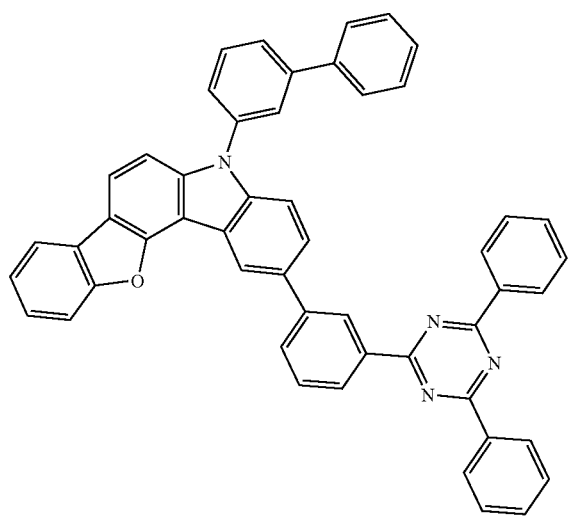
PNH9
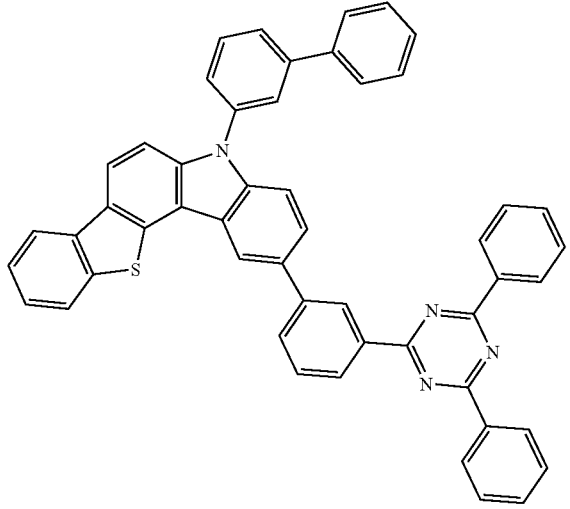
PNH2
PNH10
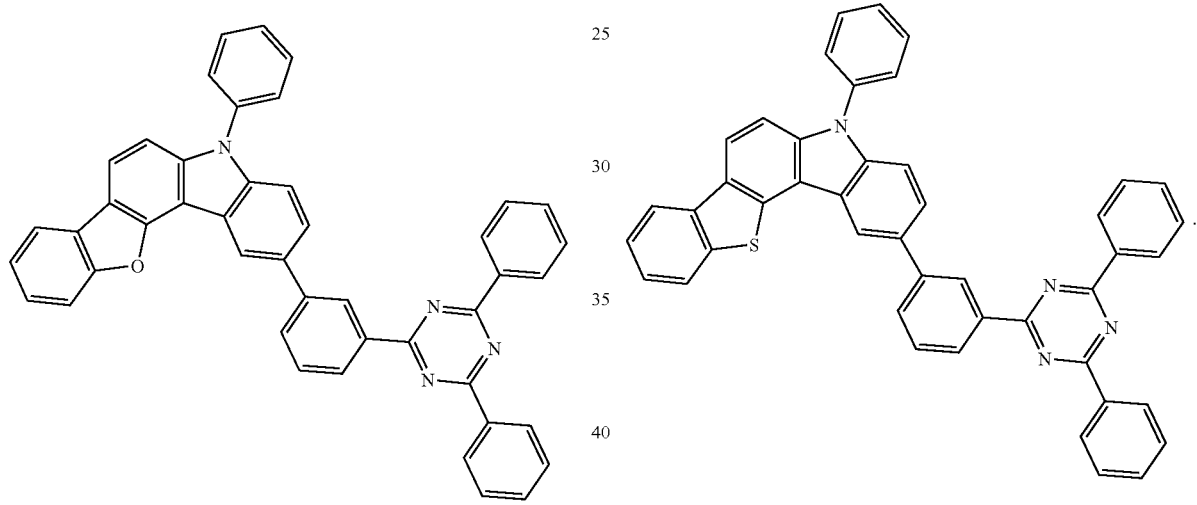
* * * * *